US012642795B2

(12) United States Patent
Kumar et al.

(10) Patent No.: US 12,642,795 B2
(45) Date of Patent: Jun. 2, 2026

(54) MRGPRX2 ANTAGONIST FOR THE TREATMENT OF PSEUDO ALLERGIC REACTIONS

(71) Applicant: The University of Hong Kong, Hong Kong (CN)

(72) Inventors: Mukesh Kumar, Hong Kong (CN); Kailash Singh, Hong Kong (CN); Billy Kwok Chong Chow, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 384 days.

(21) Appl. No.: 17/334,872

(22) Filed: May 31, 2021

(65) Prior Publication Data

US 2022/0401435 A1 Dec. 22, 2022

(51) Int. Cl.

| | |
|---|---|
| ***A61K 31/473*** | (2006.01) |
| ***A61K 45/06*** | (2006.01) |
| ***A61P 37/08*** | (2006.01) |
| ***C07D 217/24*** | (2006.01) |

(52) U.S. Cl.

CPC ............ *A61K 31/473* (2013.01); *A61K 45/06* (2013.01); *A61P 37/08* (2018.01); *C07D 217/24* (2013.01)

(58) Field of Classification Search

CPC .... A61K 31/473; A61K 45/06; A61K 31/235; A61K 31/24; A61P 37/08; A61P 29/00; C07D 217/24; C07D 221/14; C07C 69/94; C07C 275/42; C07C 2603/28

See application file for complete search history.

(56) References Cited

U.S. PATENT DOCUMENTS

| | | | |
|---|---|---|---|
| 5,605,894 | A | 2/1997 | Blank |
| 5,681,852 | A | 10/1997 | Bissett |

OTHER PUBLICATIONS

Kramer et al., Identification of Black Carbon Derived Structures in a Volcanic Ash Soil Humic Acid by Fourier Transform Ion Cyclotron Resonance Mass Spectrometry, Environ. Sci. Technol., 2004, 38, pp. 3387-3395 (Year: 2004).*

(Continued)

*Primary Examiner* — Renee Claytor
*Assistant Examiner* — Andrew P Lee
(74) *Attorney, Agent, or Firm* — Pabst Patent Group LLP

(57) ABSTRACT

Compounds that have antiallergic and/or anti-inflammatory properties and methods of making thereof are disclosed. These compounds can block MMRGPRX2 and prevent or reduce mast cells activation. Pharmaceutical formulations in a unit dosage form suitable for the delivery of the compounds to a subject in need thereof are disclosed. The pharmaceutical formulations may include one or more active agents in addition to the compounds, such as one or more additional antiallergic and/or anti-inflammatory agents. The pharmaceutical formulation can be administered by oral administration, parenteral administration, inhalation, mucosal administration, or a combination thereof. Methods for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject are also disclosed.

24 Claims, 18 Drawing Sheets

(56) References Cited

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, p. 101-113. (Year: 1989).*
Wang et al., Agents that induce pseudo-allergic reaction, Drug Discoveries & Therapeutics, 2011, 5(5), pp. 211-219 (Year: 2011).*
Alley, et al., "Feasibility of drug screening with panels of human tumor cell lines using a microculture tetrazolium assay", Cancer Research, 48(3): 589-601 (1988).
Aridor, et al., "Exocytosis in mast cells by basic secretagogues: evidence for direct activation of GTP-binding proteins", The Journal of Cell Biology, 111(3): 909-917 (1990).
Arima, et al., "Prostaglandin D_ and T(H)2 inflammation in the pathogenesis of bronchial asthma", The Korean journal of Internal Medicine, 26(1):8 (2011).
Assanasen, "Antiallergic anti-inflammatory effects of H1-antihistamines in humans", Clin. Allergy Immunol., 17:101-139 (2002).
Atanaskovic-Markovic, et al., "Diagnosis and management of drug-induced anaphylaxis in children: An EAACI position paper", Pediatric Allergy and Immunology, 30(3):269-276 (2019).
Babina, "The pseudo-allergic/neurogenic route of mast cell activation via MRGPRX2: discovery, functional programs, regulation, relevance to disease, and relation with allergic stimulation", Itch, 5(2): e32, 12 pages (2020).
Ben-Shoshan, et al., "Anaphylaxis: past, present and future", Allergy, 66(1):1-14 (2011).
Berman, et al., "The Protein Data Bank", Nucleic Acids Res., 28(1):235-242 (2000).
Biovia, "Comprehensive Modeling & Simulation for the Life Sciences", Discovery studio modeling environment, 2017, Release.
Bueb, et al., "Activation of G-Like Proteins, a Receptor-Independent Effect of Kinins in Mast Cells", Mol. Pharmacol., 38(6):816-822 (1990).
Bulfone-Paus, et al., "Positive and Negative Signals in Mast Cell Activation", Trends in Immunology, 38(9):657-667 (2017).
Callahan, et al., "Osthole, a Natural Plant Derivative Inhibits MRGPRX2 Induced Mast Cell Responses", Frontiers in Immunology, 11:703, 17 pages (2020).
Boero, et al., "Pillars of Trust: An Experimental Study on Reputation and Its Effects", Sociological Research Online, 14(5): 49-67 (2009).
Che, et al., "Structure of the Nanobody-Stabilized Active State of the Kappa Opioid Receptor", Cell, 172(1-2):55-67. e15 (2018).
Daina, et al., "SwissADME: a free web tool to evaluate pharmacokinetics, druglikeness and medicinal chemistry friendliness of small molecules", Scientific reports, 7(1): 1-13 (2017).
Dallakyan, et al., "Small-molecule library screening by docking with PyRx", Chemical biology, 1263:243-250 (2015).
Demoly, et al., "Predictive capacity of histamine release for the diagnosis of drug allergy", Allergy, 54(5): 500-506 (1999).
Ding, et al., "Assessing the similarity of ligand binding conformations with the Contact Mode Score", Computational Biology and Chemistry, 64:403-413 (2016).
Ding, et al., "Quercetin inhibits Mrgprx2-induced pseudo-allergic reaction via PLCγ-IP3R related Ca2+ fluctuations", International Immunopharmacology, 66: 185-197 (2019).
Dong, et al., "A Diverse Family of GPCRs Expressed in Specific Subsets of Nociceptive Sensory Neurons", Cell, 106(5): 619-632 (2001).
Ferguson, "Evolving concepts in G protein-coupled receptor endocytosis: the role in receptor desensitization and signaling", Pharmacological Reviews, 53(1):1-24 (2001).
Gell, "Clinical Aspects of Immunology", Clinical Aspects of Immunology, 1963:317-337 (1963).
Hanwell, et al., "Avogadro: an advanced semantic chemical editor, visualization, and analysis platform", Journal of Cheminformatics, 4(17), 17 pages (2012).
He, et al., "Mast cells and basophils are essential for allergies: mechanisms of allergic inflammation and a proposed procedure for diagnosis", Acta Pharmacologica Sinica, 34(10):1270-1283 (2013).
Hughes, et al., "Principles of early drug discovery", British Journal of Pharmacology, 162(6):1239-1249 (2011).
Jimenez-Rodriguez, et al., "Anaphylaxis in the 21st century: phenotypes, endotypes, and biomarkers", Journal of Asthma and Allergy, 11:121-142 (2018).
Kroeze, et al., "PRESTO-Tango as an open-source resource for interrogation of the druggable human GPCRome", Nature Structural & Molecular Biology, 22(5):362-369 (2015).
Krystel-Whittemore, et al., "Mast Cell: A Multi-Functional Master Cell", Frontiers in Immunology, 6:620, 12 pages (2016).
Kühn, et al., "Mas-related G protein-coupled receptor X2 and its activators in dermatologic allergies", Journal of Allergy and Clinical Immunology, 147(2):456-469 (2020).
Kumar, et al., "Protective Effect of Genistein against Compound 48/80 Induced Anaphylactoid Shock via Inhibiting MAS Related G Protein-Coupled Receptor X2 (MRGPRX2)", Molecules, 25(5):1028, 16 pages (2020).
Lansu, et al., "In silico design of novel probes for the atypical opioid receptor MRGPRX2", Nature Chemical Biology, 13(5):529-536 (2017).
Li, et al., "A murine model of peanut anaphylaxis: T- and B-cell responses to a major peanut allergen mimic human response", Journal of Allergy and Clinical Immunology, 106(1): 150-158 (2000).
Liang, et al., "Fast-dissolving intraoral drug delivery systems", Expert Opinion in Therapeutic Patents, 11(6):981-986 (2001).
Lipinski, et al., "Experimental and computational approaches to estimate solubility and permeability in drug discovery and development settings", Advanced Drug Delivery Reviews, 23(1-3):3-25 (1997).
Lipinski, "Drug-like properties and the causes of poor solubility and poor permeability", Journal of Pharmacological and Toxicological Methods, 44(1):235-249 (2000).
Mashiach, et al., "FireDock: a web server for fast interaction refinement in molecular docking", Nucleic Acids Research, 36(suppl_2): W229-W232 (2008).
McNeil, et al., "Identification of a mast-cell-specific receptor crucial for pseudoallergic drug reactions", Nature, 519(7542): 237-241 (2015).
Motakis, et al., "Redefinition of the human mast cell transcriptome by deep-CAGE sequencing", Blood, 123(17): e58-e67 (2014).
Mousli, et al., "Interaction of substance P, compound 4880 and mastoparan with the a-subunit C-terminus of G protein", Immunology Letters, 25(4): 355-357 (1990).
Navinés-Ferrer, et al., "MRGPRX2-mediated mast cell response to drugs used in perioperative procedures and anaesthesia", Scientific Reports, 8(1):1-11 (2018).
Occhiuto, et al., "Store-Operated Calcium Entry via STIM1 Contributes to MRGPRX2 Induced Mast Cell Functions", Frontiers in Immunology, 10:3143, 15 pages (2020).
Ogasawara, et al., "Novel MRGPRX2 antagonists inhibit IgE-independent activation of human umbilical cord blood-derived mast cells", Journal of Leukocyte Biology, 106(5): 1069-1077 (2019).
Porebski, et al., "Mas-Related G Protein-Coupled Receptor-X2 (MRGPRX2) in Drug Hypersensitivity Reactions" Frontiers in Immunology, 9:3027, 9 pages (2018).
Prisant, et al., "Structure validation by Calpha geometry: phi, psi and Cbeta deviation", Proteins, 50(3): 437-450 (2003).
Rådinger, et al., "Generation, Isolation, and Maintenance of Human Mast Cells and Mast Cell Lines", Current Protocols in Immunology, 90(1): 7.37. 1-7.37. 12 (2010).
Rajan, "The Gell-Coombs classification of hypersensitivity reactions: a reinterpretation", Trends in Immunology, 24(7): 376-379 (2003).
Read, et al., "Compound 48-80. Structure-activity relations and poly-THIQ, a new, more potent analog", Journal of Medicinal Chemistry, 16(11): 1292-1295 (1973).

(56) References Cited

OTHER PUBLICATIONS

Reddy, et al., "A single amino acid in MRGPRX2 necessary for binding and activation by pruritogens", Journal of Allergy and Clinical Immunology, 140(6): p. 1726-1728 (2017).
Release, Maestro-Desmond Interoperability Tools, Schrodinger, New York, NY, 2017.
Schrodinger, "The pyMOL Molecular Graphics System", Scientific Research, 1.3r1: 1-3 (2010).
Shin, et al., "Inhibitory action of water soluble fraction of Terminalia chebula on systemic and local anaphylaxis", Journal of Ethnopharmacology, 74(2):133-140 (2001).
Singh, et al., "Structure-Activity Relationship Studies of N- and C-Terminally Modified Secretin Analogs for the Human Secretin Receptor", Plos One, 11(3): e0149359 (2016).
Slater, et al., "Studies on Succinate-Tetrazolium Reductase Systems. III. Points of Coupling of Four Different Tetrazolium Salts", Biochimica et Biophysica Acta, 77: 383-393 (1963).
Solensky, et al., "Drug allergy: an updated practice parameter", Annals of Allergy, Asthma & Immunology, 105(54): 259-273 (2010).
Subramanian, et al., "Roles of Mas-related G protein-coupled receptor X2 on mast cell-mediated host defense, pseudoallergic drug reactions, and chronic inflammatory diseases", Journal of Allergy and Clinical Immunology, 138(3):700-710 (2016).
Subramanian, et al., "Mas-related gene X2 (MrgX2) is a novel G protein-coupled receptor for the antimicrobial peptide LL-37 in human mast cells: resistance to receptor phosphorylation, desensitization, and internalization", Journal of Biological Chemistry, 286(52):44739-44749 (2011).
Sunseri, et al., "Pharmit: interactive exploration of chemical space", Nucleic Acids Research, 44(5 W1): W442-W448 (2016).
Turčić, et al., "Dermatologic medication in pregnancy", Acta Dermatovenerologica Croatica, 17(1):40-47 (2009).
Trott, et al., "AutoDock Vina: improving the speed and accuracy of docking with a new scoring function, efficient optimization, and multithreading", Journal of Computational Chemistry, 31(2):455-461 (2010).
Webb, et al., "Comparative Protein Structure Modeling Using MODELLER", Current Protocols in Bioinformatics, 54(1):5.6. 1-5. 6. 37 (2016).
Yoon, et al., "Inhibitory effect of chaga mushroom extract on compound 48/80-induced anaphylactic shock and IgE production in mice", International Immunopharmacology, 15(4):666-670 (2013).
Yuan, et al., "MRGPRX2 mediates immediate-type pseudo-allergic reactions induced by iodine-containing iohexol", Biomedicine & Pharmacotherapy, 137:111323 (2021).
Fan, et al., "Comparison of the Optical and Electrochemical Properties of Bi(perylene diimide)s Linked through Ortho and Bay Positions", ACS Omega, 2:377-385 (2017).
Yan, et al., "Synthesis and aggregation-induced fluorescence emission properties of boron-containing derivatives that respond to viscous alcohols", New J. Chem., 38:6088 (2014).
Yin, et al., "A series of bowl-shaped PDI dimers designed for organic photovoltaic cells through engineering N-annulated bridge towards potential alternatives of PDI bridged dimer acceptors", Dyes and Pigments, 148:394-404 (2018).

* cited by examiner

GE0117

GE0118

GE0119

GE1109

GE1110

GE1111

MRGPRX2 ANTAGONIST FOR THE TREATMENT OF PSEUDO ALLERGIC REACTIONS

FIELD OF THE INVENTION

This invention is generally in the field of synthetic compounds and their use as antiallergic agents.

BACKGROUND OF THE INVENTION

Allergic diseases are prevalent all over the world and common in all age groups. For instance, in the United States, allergies are the 6th leading cause of chronic illness, which affects over 50 million Americans with a cost of $18 billion/year. In Hong Kong, allergic diseases have been reported as fast-growing diseases with a high pediatric population burden. Pseudo allergic reaction is an allergic reaction characterized by similar systemic and local symptoms as anaphylaxis. However, pseudo allergic reaction shares a different mechanisms of MCs activation to that of Immunoglobulin E (IgE). Pseudo allergic reactions are also known as non-IgE mediated hypersensitivity reactions which often elicited by the allergens or first dose of medication and cause local and systemic hypersensitivity reactions. Pseudo allergic reactions do not elicit antigen-specific immune responses but do evoke histamine release, activation of the complement system, atypical synthesis of eicosanoids, and cytokine release. The signs and symptoms of pseudo allergic reactions are practically identical to IgE-mediated symptoms such as skin flushing, headache, edema, hypotension, angioedema, urticaria, bronchospasm and gastrointestinal signs. The pseudo allergic reactions are attributed to two-thirds of hypersensitivity reactions; however, the lack of systematic studies of the causes and mechanisms are major challenges for the diagnosis and treatment of these reactions.

Mast cells (MCs) are tissue-resident innate immune cells, present predominately and strategically at exterior environment barriers, such as the skin and the respiratory tract. MCs are known for their densely packed secretory granules, which contain several pre-synthesized mediators, such as proteases and histamine. MCs granules also release de novo synthesized mediators such as prostaglandins (PG)s, chemokines, and cytokines. MCs can rapidly release these mediators on activation via allergens, infectious agents, toxins, and drugs. MCs activation mechanism is cross-linking of high-affinity Immunoglobulin E (IgE) receptors (FcεRI); however, MCs can activate by non-IgE pathway such as GPCR, particularly, antibodies against IgE receptor. Mas-related G protein-coupled receptor (GPCR) X2 (MRGPRX2) has been identified as a GPCR responsible for non-IgE-mediated allergic and inflammatory diseases. Several endogenous peptides, allergens, infectious agents, toxins and FDA-approved drugs such as fluoroquinolone antibiotics, neuromuscular blockers, Icatibant, opioids, diagnostic agents have been reported to cause allergy via MRGPRX2 activation.

There are no selective drugs available for the treatment of such allergic reaction, only symptomatic treatment options available, which include allergen avoidance, or emergency treatment with antihistaminic and corticosteroid and monoclonal antibodies against IgE receptors. For example, currently available drugs such as epinephrine and antihistaminic are strictly symptomatic solutions. Also, several cases of allergies are refractive to currently available treatments and fail to treat acute to severe cases of allergies. For example, MRGPRX2 can be activated by several ligands, including antibiotics, antimicrobial peptides, neuropeptides, ant venom peptides, and anesthetics. Also, several endogenous ligands such as the cathelicidins LL-37, and neuropeptide substance P, can activate MRGPRX2 in response to infection and tissue injury. These ligands can activate MCs via MRGPRX2, which induce and amplify inflammation and play a role in mediating the pathophysiology of chronic diseases such as systemic urticaria, asthma and rosacea. Moreover, exogenous stimuli such as C48/80, ant-venom peptides, and drugs (fluoroquinolone antibiotics neuromuscular blockers) has been reported to activate MCs-MRGPRX2 and cause pseudo allergic reactions and inflammation.

Few MRGPRX2 antagonists have recently been reported, such as peptide antagonist QWF, two small compounds, and DNA aptamer. However, they have both pharmacological and pharmaceutical limitations. For instance, QWF and DNA aptamer has the limitation of plasma degradation and low bioavailability; they degrade rapidly in the blood plasma. The two small compounds reported by Ogasawara, et al on the *Journal of Leukocyte Biology* in 2019 show only in-vitro antagonistic activity but failed to show ex vivo and in vivo antagonistic activity. There is no treatment strategy to treat the root cause of allergic reactions (mast cell degranulation).

There remains a need to develop antiallergic compounds that can prevent or treat non-IgE mediated pseudo allergic reactions, allergic diseases, and/or inflammatory diseases.

Therefore, it is the object of the present invention to provide antiallergic compounds.

It is a further object of the present invention to provide methods of making the antiallergic compounds.

It is a further object of the present invention to provide methods of using the antiallergic compounds.

SUMMARY OF THE INVENTION

Synthetic compounds as antiallergic agents and their methods of making and using are described.

Generally, the compounds can have two cyclic ring moieties, where each of the two cyclic ring moieties contains a fused ring structure. In some forms, the compound can have the structure of Formula I:

Formula I

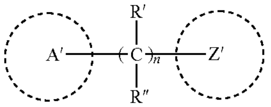

(a) where n is an integer from 0 to 6, from 0 to 5, from 0 to 4, from 0 to 3, from 0 to 2, or 0 or 1; (b) where $R_1$ and $R_2$ are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; (c) where A' and Z' are independently a substituted or unsubstituted polyaryl or a substituted or unsubstituted polyheteroaryl; and (d) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, wherein the compound has the structure of

Formula Ia

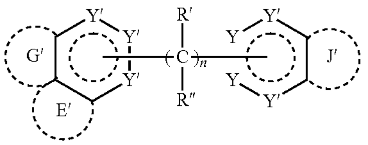

(a) where E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(b) where J' is a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(c) where each occurrence of Y' is independently $CR_1$, O, S, or $NR_2$, and at least one Y' is O, S, or $NR_2$, where $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (d) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, n is 0.

In some forms of Formula I, A' can have the structure of

Formula II

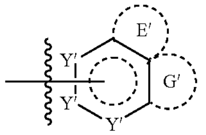

(a) where E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; (b) where each occurrence of Y' is independently $CR_1$, O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (c) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol. In some forms of Formula I, A' can have the structure of Formula IVa

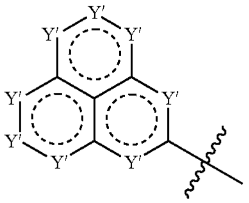

Formula IVb

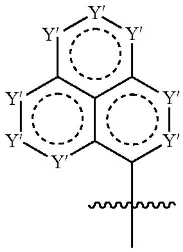

(a) where each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, A' can have the structure of

Formula Va

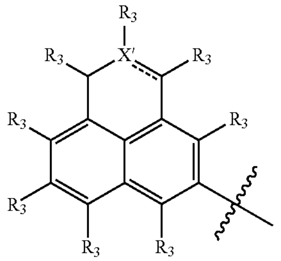

Formula Vb

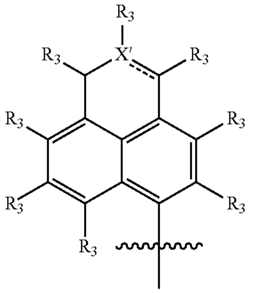

(a) where X' is C, N, O, or S; (b) where each occurrence of $R_3$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (c) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formulae Va and Vb, (a) where X' is C or N; (b) where each occurrence of $R_3$ is independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen; and (c) where the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

In some forms of Formulae Va and Vb, (a) where X' is C or N; (b) where each occurrence of $R_3$ is independently a hydrogen, a substituted or unsubstituted alkyl, a substituted or unsubstituted aryl, an amino, an oxo, a halogen, a hydroxyl, a heterocyclic group

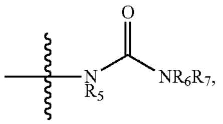

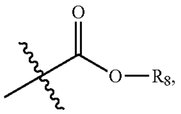

or

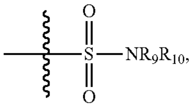

and $R_5$-$R_{10}$ are independently a hydrogen, a substituted or unsubstituted alkyl, a substituted or unsubstituted aryl, an amino, or a halogen; and (c) where the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

In some forms of Formulae Va and Vb, (a) where X' is C or N; (b) where each occurrence of $R_3$ is independently a hydrogen, a substituted or unsubstituted alkyl, an oxo, a hydroxyl, or a carboxyl; and (c) where the substituent are independently a substituted or unsubstituted alkyl, a substituted or unsubstituted heterocyclyl, a substituted or unsubstituted stituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

In some forms of Formula I, Z' can have the structure of

Formula VI

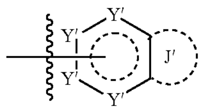

(a) where each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; (b) where J' is a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; and (c) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, Z' can have the structure of

Formula VIII

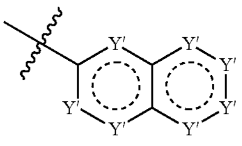

(a) where each occurrence of Y' is independently $CR_1$, O, S, or $NR_2$, and at least one Y' is O, S, or $NR_2$, where $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, Z' can have the structure of

Formula IX

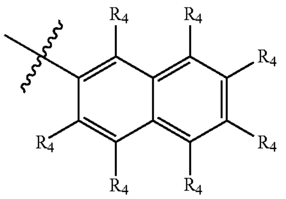

(a) where each occurrence of $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula IX, (a) where each occurrence of $R_4$ is independently a hydrogen, a substituted or unsubstituted alkyl, a substituted or unsubstituted aryl, an amino, an oxo, a halogen, a hydroxyl, a heterocyclic group,

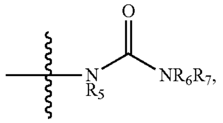

or

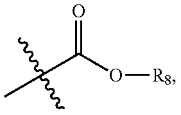

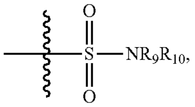

and $R_5$-$R_{10}$ are independently a hydrogen, a substituted or unsubstituted alkyl, a substituted or unsubstituted aryl, an amino, or a halogen; and (b) where the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

In some forms of Formula IX, (a) where each occurrence of $R_4$ is independently a hydrogen,

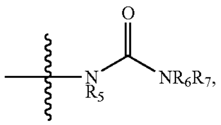

or

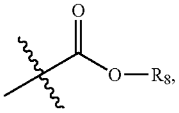

and $R_5$-$R_8$ are independently a hydrogen or a substituted or unsubstituted alkyl; and (b) where the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

In some forms, the compounds have the structure of

GE0117

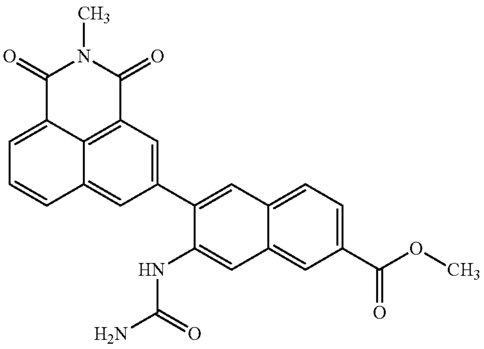

-continued

GE0118

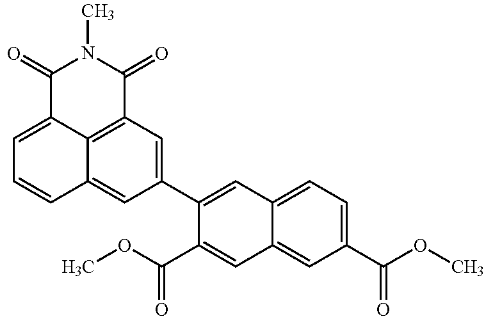

GE0119

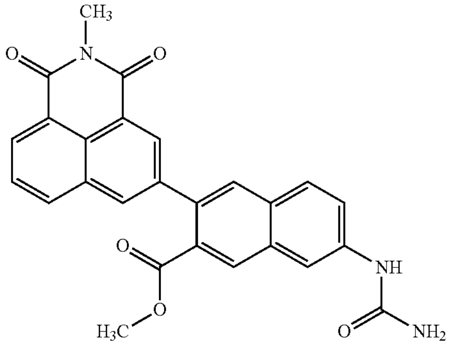

GE1109

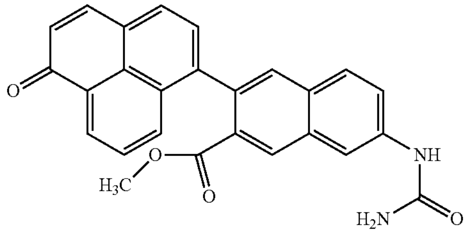

GE1109

GE1110

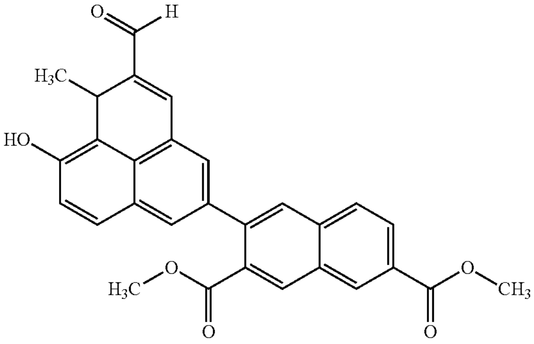

GE1110

-continued

GE1111

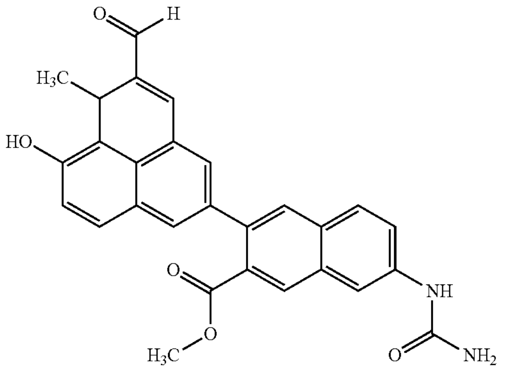

GE1111

Pharmaceutical compositions and pharmaceutical formulations in a unit dosage form suitable for the delivery of the compounds and their preparation are disclosed. Generally, the pharmaceutical composition or formulation contains one or more of the compounds and a suitable pharmaceutically acceptable excipient. The compounds in the pharmaceutical compositions or formulations are in an effective amount for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject in need thereof. In some forms, the pharmaceutical composition or formulation can further contain one or more active agents in addition to the compounds, such as one or more additional antiallergic agents or one or more additional anti-inflammatory agents, or a combination thereof.

The methods of making the compounds disclosed herein can include (i) mixing a reactant mixture and a catalyst to form a reaction mixture, wherein the reactant mixture comprises a first reactant, a second reactant, and a solvent; and (ii) heating the reaction mixture at a suitable temperature for a period of time sufficient to form a product containing the compounds, where step (i) can be performed prior to or simultaneously with step (ii).

In some forms of the method, the first reactant can have the structure of

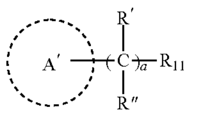

Formula XIII (a) where a is an integer from 0 to 6, from 0 to 5, from 0 to 4, from 0 to 3, from 0 to 2, or 0 or 1; (b) where R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; (c) where A' is a substituted or unsubstituted polyaryl or a substituted or unsubstituted polyheteroaryl; (d) where $R_{11}$ is a halogen or has the structure of

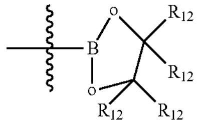

Formula XIV where each occurrence of $R_{12}$ is independently a hydrogen or a substituted or unsubstituted alkyl; and (e) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of the method, the second reactant can have the structure of

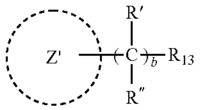

Formula XIX (a) where b is an integer from 0 to 6, from 0 to 5, from 0 to 4, from 0 to 3, from 0 to 2, or 0 or 1; (b) where R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; (c) where Z' is a substituted or unsubstituted polyaryl or a substituted or unsubstituted polyheteroaryl; (d) where $R_{13}$ is trifluoromethanesulfonate ("OTf") or has the structure of Formula XIV; and (e) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of the method, the solvent used in step (i) can be water, dioxane, dimethoxyethane, 2-methyltetrahydrofuran, cyclopentyl methyl ether, tetrahydrofuran, tert-butyl methyl ether, or dichloromethane, or a combination thereof. In some forms of the method, the catalyst can be $PdCl_2(dppf)$, $PdCl_2(dppf)DCM$ Complex, Tetrakis, $PdCl_2(PPh_3)_2$, XPhos Pd G3, and $Pd(OAc)_2/PPh_3$, and a combination thereof.

In some forms of the method, in step (ii), the reaction mixture can be heated at a temperature in a range from 50° C. to 150° C., from 60° C. to 150° C., from 70° C. to 150° C., from 80° C. to 150° C., from 50° C. to 140° C., from 50° C. to 120° C., from 70° C. to 120° C., from 80° C. to 120° C., such as about 100° C., for a time period of at least 1 hour, at least 2 hours, at least 3 hours, at least 4 hours, at least 5 hours, at least 6 hours, at least 8 hours, at least 10 hours, up to 20 hours, up to 18 hours, up to 16 hours, in a range from 1 hour to 18 hours, from 2 hours to 16 hours, or from 2 hours to 15 hours, to form the product containing the compounds.

In some forms, the method further includes mixing the first reactant, the second reactant, and the solvent to form the reactant mixture prior to step (i), purging the reactant mixture with an inert gas prior to step (ii), stirring the reaction mixture during step (ii), and/or purifying the product containing the compound.

The methods of using the compounds for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject in need thereof can include administering to the subject the pharmaceutical formulation containing one or more compounds. The administration step can occur one or more times. The subject is typically a mammal, such as a human. In some forms of the method, the pharmaceutical formulation can be administered by oral administration, parenteral administration, inhalation, mucosal administration, topical or a combination thereof.

In some forms of the method, following a single administration or more than one administration of the pharmaceutical formulation to the subject, an effective amount of the compounds to prevent or reduce inflammation, prevent or reduce anaphylaxis symptoms, prevent or reduce tissue damage, and/or prevent or reduce MCs degranulation in the subject is administered to the subject.

In some forms, the method further includes administering to the subject a second active agent, optionally more than one second active agent, prior to, during, and/or subsequent to step (i). The second active agent can be an antiallergic agent or an anti-inflammatory agent, or a combination thereof.

Methods for treating mast cells in a subject in need thereof are also disclosed. The method can include (i) administering to the subject the pharmaceutical formulation containing one or more compounds, where step (i) occurs one or more times.

In some forms of the method, following a single administration or more than one administration of the pharmaceutical formulation to the subject, an effective amount of the compounds to inhibit MCs degranulation, inhibit MRGPRX2 activation, reduce calcium cation ("$Ca^{2+}$") flux in the MCs, and/or reduce release of inflammatory chemokine and/or cytokine, compared with cells in a control not treated with the compounds, tested under the same conditions, is administered to the subject.

BRIEF DESCRIPTION OF THE DRAWINGS

FIG. 10A shows the quantification of % increase in paw thickness after 15 min of C48/80 injection (30 μg/ml). FIG. 10B shows the quantification of Evans blue leakage into the paw after 15 min of C48/80 injection (30 μg/ml). The data are presented as the mean±SEM from 6-8 mice/group, $^{###}$p<0.001 as compared to saline and *P<0.05, P<0.01, *P<0.001 as compared to C48/80.

FIG. 12A shows the effect on changes in body temperature after intraperitoneal injection of 8 mg/kg of C48/80. FIG. 12B shows the effect on systemic anaphylaxis symptoms scores after intraperitoneal injection of 8 mg/kg of C48/80. The data are presented as the mean±SEM from 6-8 mice/group $^{####}$P<0.001 as compared to vehicle control, and **P<0.01, as compared to C48/80 control.

DETAILED DESCRIPTION OF THE INVENTION

I. Definitions

Figure 1A:
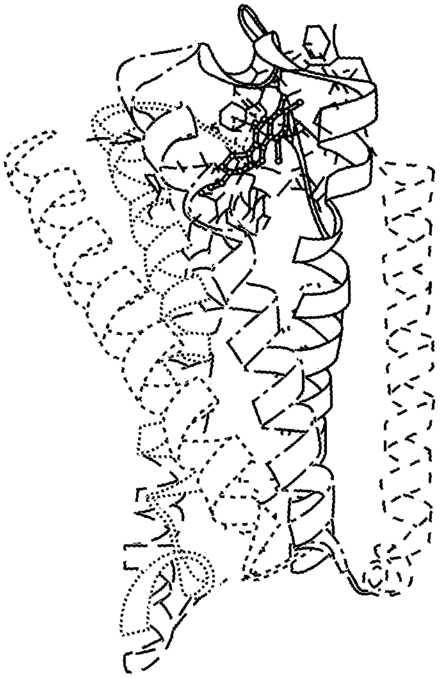
FIG. 1A is a 3D illustration showing genistein at the binding site of the N-terminal amino acid residues of MRGPRX2.

It is to be understood that the disclosed compounds, compositions, and methods are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, an amino acid. Such a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, and an amino acid can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with the permitted valence of the substituted atom and the substituent and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched chain alkyl, and cycloalkyl (alicyclic). In some forms, a straight-chain or branched chain alkyl has 30 or fewer carbon atoms in its backbone (e.g., $C_1$-$C_{30}$ for straight chains, $C_3$-$C_{30}$ for branched chains), 20 or fewer, 15 or fewer, or 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Likewise, a cycloalkyl is a non-aromatic carbon-based ring composed of at least three carbon atoms, such as a nonaromatic monocyclic or nonaromatic polycyclic ring containing 3-30 carbon atoms, 3-20 carbon atoms, or 3-10 carbon atoms in their ring structure, and have 5, 6 or 7 carbons in the ring structure. Cycloalkyls containing a polycyclic ring system can have two or more non aromatic rings in which two or more carbons are common to two adjoining rings (i.e., "fused cycloalkyl rings"). Examples of cycloalkyl groups include, but are not limited to, cyclopropyl, cyclobutyl, cyclopentyl, cyclohexyl, cycloheptyl, cyclooctanyl, etc.

The term "alkyl" as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents can be any substituents described above, e.g., halogen (such as fluorine, chlorine, bromine, or iodine), hydroxyl, carbonyl (such as a carboxyl, alkoxycarbonyl, formyl, or an acyl), thiocarbonyl (such as a thioester, a thioacetate, or a thioformate), aryl, alkoxyl, aralkyl, phosphonium, phosphanyl, phosphonyl, phosphoryl, phosphate, phosphonate, a phosphinate, amino, amido, amidine, imine, cyano, nitro, azido, oxo, sulfhydryl, thiol, alkylthio, silyl, sulfinyl, sulfate, sulfonate, sulfamoyl, sulfonamido, sulfonyl, heterocyclyl, an aromatic or heteroaromatic moiety. —NRR', wherein R and R' are independently hydrogen, alkyl, or aryl, and wherein the nitrogen atom is optionally quaternized; —SR, wherein R is a phosphonyl, a sulfinyl, a silyl a hydrogen, an alkyl, or an aryl; —CN; $—NO_2$; —COOH; carboxylate; —COR, —COOR, or $—CON(R)_2$, wherein R is hydrogen, alkyl, or aryl; imino, silyl, ether, haloalkyl (such as $—CF_3$, $—CH_2—CF_3$, $—CCl_3$); —CN; $—NCOCOCH_2CH_2$; —NCOCOCHCH; and —NCS; and combinations thereof. The term "alkyl" also includes "heteroalkyl".

It will be understood by those skilled in the art that the moieties substituted on the hydrocarbon chain can themselves be substituted, if appropriate. For instance, the substituents of a substituted alkyl may include halogen, hydroxy, nitro, thiols, amino, aralkyl, azido, imino, amido, phosphonium, phosphanyl, phosphoryl (including phosphonate and phosphinate), oxo, sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

"Heteroalkyl," as used herein, refers to straight or branched chain, or cyclic carbon-containing alkyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkyl group" is a cycloalkyl group as defined above where at least one of the carbon atoms of the ring is substituted with a heteroatom such as, but not limited to, nitrogen, oxygen, sulfur, or phosphorus.

The term "alkenyl" as used herein is a hydrocarbon group of from 2 to 24 carbon atoms and structural formula containing at least one carbon-carbon double bond. Alkenyl groups include straight-chain alkenyl groups, branched-chain alkenyl, and cycloalkenyl. A cycloalkenyl is a non-aromatic carbon-based ring composed of at least three carbon atoms and at least one carbon-carbon double bond, such as a nonaromatic monocyclic or nonaromatic polycyclic ring containing 3-30 carbon atoms and at least one carbon-carbon double bond, 3-20 carbon atoms and at least one carbon-carbon double bond, or 3-10 carbon atoms and at least one carbon-carbon double bond in their ring structure, and have 5, 6 or 7 carbons and at least one carbon-carbon double bond in the ring structure. Cycloalkenyls containing a polycyclic ring system can have two or more non-aromatic rings in which two or more carbons are common to two adjoining rings (i.e., "fused cycloalkenyl rings") and contain at least one carbon-carbon double bond. Asymmetric structures such as (AB)C═C(C'D) are intended to include both the E and Z isomers. This may be presumed in structural formulae herein wherein an asymmetric alkene is present, or it may be explicitly indicated by the bond symbol C. The term "alkenyl" as used throughout the specification, examples, and claims is intended to include both "unsubstituted alkenyls" and "substituted alkenyls," the latter of which refers to alkenyl moieties having one or more substituents replacing a hydrogen on one or more carbons of the hydrocarbon backbone. The term "alkenyl" also includes "heteroalkenyl".

The term "substituted alkenyl" refers to alkenyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, oxo, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkenyl," as used herein, refers to straight or branched chain, or cyclic carbon-containing alkenyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkenyl group" is a cycloalkenyl group where at least one of the carbon atoms of the ring is substituted with a heteroatom such as, but not limited to, nitrogen, oxygen, sulphur, or phosphorus.

The term "alkynyl group" as used herein is a hydrocarbon group of 2 to 24 carbon atoms and a structural formula containing at least one carbon-carbon triple bond. Alkynyl groups include straight-chain alkynyl groups, branched-chain alkynyl, and cycloalkynyl. A cycloalkynyl is a non-aromatic carbon-based ring composed of at least three carbon atoms and at least one carbon-carbon triple bond, such as a nonaromatic monocyclic or nonaromatic polycyclic ring containing 3-30 carbon atoms and at least one carbon-carbon triple bond, 3-20 carbon atoms and at least one carbon-carbon triple bond, or 3-10 carbon atoms and at least one carbon-carbon triple bond in their ring structure, and have 5, 6 or 7 carbons and at least one carbon-carbon triple bond in the ring structure. Cycloalkynyls containing a polycyclic ring system can have two or more non-aromatic rings in which two or more carbons are common to two adjoining rings (i.e., "fused cycloalkynyl rings") and contain at least one carbon-carbon triple bond. Asymmetric structures such as (AB)C≡C(C"D) are intended to include both the E and Z isomers. This may be presumed in structural formulae herein wherein an asymmetric alkyne is present, or it may be explicitly indicated by the bond symbol C. The term "alkynyl" as used throughout the specification, examples, and claims is intended to include both "unsubstituted alkynyls" and "substituted alkynyls," the latter of which refers to alkynyl moieties having one or more substituents replacing a hydrogen on one or more carbons of the hydrocarbon backbone. The term "alkynyl" also includes "heteroalkynyl".

The term "substituted alkynyl" refers to alkynyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkynyl," as used herein, refers to straight or branched chain, or cyclic carbon-containing alkynyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkynyl group" is a cycloalkynyl group where at least one of the carbon atoms of the ring is substituted with a heteroatom such as, but not limited to, nitrogen, oxygen, sulphur, or phosphorus.

The term "aryl" as used herein is any $C_5$-$C_{26}$ carbon-based aromatic group, heteroaromatic, fused aromatic, or fused heteroaromatic. For example, "aryl," as used herein can include 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused aromatic rings"), wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents. Such substituents can be any substituents described above, e.g., halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), —CN, aryl, heteroaryl, and combinations thereof.

"Heterocycle" and "heterocyclyl" are used interchangeably and refer to a cyclic radical attached via a ring carbon or nitrogen atom of a non-aromatic monocyclic or polycyclic ring containing 3-30 ring atoms, 3-20 ring atoms, 3-10 ring atoms, or 5-6 ring atoms, where each ring contains carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Heterocycles can be a heterocycloalkyl, a heterocycloalkenyl, a heterocycloalkynyl, etc, such as piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{30}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for “substituted heteroaryl”.

The term “substituted heteroaryl” refers to a heteroaryl group in which one or more hydrogen atoms on one or more heteroaromatic rings are substituted with one or more substituents. Such substituents can be any substituents described above, e.g., halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF3, $—CH_2—CF_3$, $—CCl_3$), —CN, aryl, heteroaryl, and combinations thereof.

The term “polyaryl” refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. For example, a “polyaryl” can be polycyclic ring systems having two or more cyclic rings in which two or more carbons are common to two adjoining rings (i.e., “fused aromatic rings”), wherein two or more of the rings are aromatic. When two or more heteroaryls are involved, the chemical moiety can be referred to as a “polyheteroaryl.”

The term “substituted polyaryl” refers to a polyaryl in which one or more of the aryls, heteroaryls are substituted, with one or more substituents. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a “substituted polyheteroaryl.”

The term “cyclic ring” refers to a substituted or unsubstituted monocyclic ring or a substituted or unsubstituted polycyclic ring (such as those formed from single or fused ring systems), such as a substituted or unsubstituted cycloalkyl, a substituted or unsubstituted cycloalkenyl, a substituted or unsubstituted cycloalkynyl, a substituted or unsubstituted heterocyclyl, a substituted or unsubstituted aryl, a substituted or unsubstituted polyaryl, a substituted or unsubstituted heteroaryl, and a substituted or unsubstituted polyheteroaryl, that have from three to 30 carbon atoms, as geometric constraints permit. The substituted cycloalkyls, cycloalkenyls, cycloalkynyls, and heterocyclyls are substituted as defined above for the alkyls, alkenyls, alkynyls, heterocyclyls, aryls, heteroaryl, polyaryls, and polyheteroaryls, respectively.

The term “aralkyl” as used herein is an aryl group or a heteroaryl group having an alkyl, alkynyl, or alkenyl group as defined above attached to the aromatic group, such as an aryl, a heteroaryl, a polyaryl, or a polyheteroaryl. An example of an aralkyl group is a benzyl group.

The terms “alkoxyl” or “alkoxy,” “aroxy” or “aryloxy,” generally describe compounds represented by the formula $—OR^v$, wherein $R^v$ includes, but is not limited to, a substituted or unsubstituted alkyl, a substituted or unsubstituted alkenyl, a substituted or unsubstituted alkynyl, a substituted or unsubstituted cycloalkyl, a substituted or unsubstituted heterocyclyl, a substituted or unsubstituted cycloalkenyl, a substituted or unsubstituted heterocycloalkenyl, a substituted or unsubstituted aryl, a substituted or unsubstituted heteroaryl, a substituted or unsubstituted polyaryl, a substituted or unsubstituted polyheteroaryl, a substituted or unsubstituted arylalkyl, a substituted or unsubstituted heteroalkyl, a substituted or unsubstituted alkylaryl, a substituted or unsubstituted alkylheteroaryl, a substituted or unsubstituted aralkyl, a substituted or unsubstituted carbonyl, a phosphonium, a phosphanyl, a phosphonyl, a sulfinyl, a silyl, a thiol, an amido, and an amino. Exemplary alkoxyl groups include methoxy, ethoxy, propyloxy, tert-butoxy and the like. A “lower alkoxy” group is an alkoxy group containing from one to six carbon atoms. An “ether” is two functional groups covalently linked by oxygen as defined below. Accordingly, the substituent of an alkyl that renders that alkyl an ether is or resembles an alkoxyl, such as can be represented by one of —O-alkyl, —O-alkenyl, —O-alkynyl, —O-aryl, —O-heteroaryl, —O-polyaryl, —O-polyheteroaryl, —O-heterocyclyl, etc.

The term “substituted alkoxy” refers to an alkoxy group having one or more substituents replacing one or more hydrogen atoms on one or more carbons of the alkoxy backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, oxo, sulfate, sulfonate, sulfamoyl, sulfonamido, sulfonyl, heterocyclyl, alkylaryl, haloalkyl, —CN, aryl, heteroaryl, and combinations thereof.

The term “ether” as used herein is represented by the formula $A^2OA^1$, where $A^2$ and $A^1$ can be, independently, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl, a substituted or unsubstituted polyaryl, a substituted or unsubstituted polyheteroaryl, a phosphonium, a phosphanyl, a phosphonyl, a sulfinyl, a silyl, a thiol, a substituted or unsubstituted carbonyl, an alkoxy, an amido, or an amino, described above.

The term “polyether” as used herein is represented by the formula:

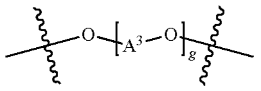

where $A^3$, $A^2$, and $A^1$ can be, independently, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl, a substituted or unsubstituted polyaryl, a substituted or unsubstituted polyheteroaryl, a phosphonium, a phosphanyl, a substituted or unsubstituted carbonyl, an alkoxy, an amido, or an amino, described above; g can be a positive integer from 1 to 30.

The term "phenoxy" is art-recognized and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "amino" as used herein includes the group

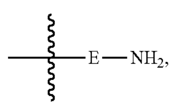

(primary amino)

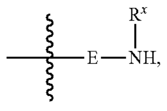

(secondary amino)

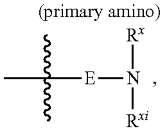

(tertiary amino)

and

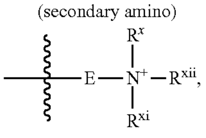

(quaternary amino)

wherein, E is absent, or E is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl, wherein independently of E, $R^x$, $R^{xi}$, and $R^{xii}$ each independently represent a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—R'''; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. The term "quaternary amino" also includes the groups where the nitrogen, $R^x$, $R^{xi}$, and $R^{xii}$ with the $N^+$ to which they are attached complete a heterocyclyl or heteroaryl having from 3 to 14 atoms in the ring structure.

The terms "amide" or "amido" are used interchangeably, refer to both "unsubstituted amido" and "substituted amido" and are represented by the general formula:

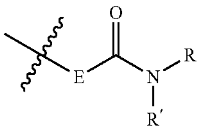

or

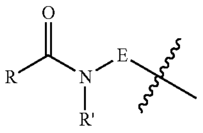

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted aryl, substituted or unsubstituted heteroaryl, a substituted or unsubstituted polyaryl, a substituted or unsubstituted polyheteroaryl, or a substituted or unsubstituted heterocyclyl, wherein independently of E, R and R' each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—R''', or R and R' taken together with the N atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. In some forms, when E is oxygen, a carbamate is formed.

"Carbonyl," as used herein, is art-recognized and includes such moieties as can be represented by the general formula:

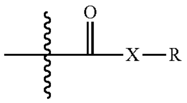

or

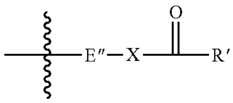

wherein X is a bond, or represents an oxygen or a sulfur, and R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or $—(CH_2)_m—R''$, or a pharmaceutical acceptable salt; E" is absent, or E" is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl; R' represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or $—(CH_2)_m—R''$; R" represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. Where X is oxygen and R is defines as above, the moiety is also referred to as a carboxyl group. When X is oxygen and R is hydrogen, the formula represents a "carboxylic acid". Where X is oxygen and R' is hydrogen, the formula represents a "formate". Where X is oxygen and R or R' is not hydrogen, the formula represents an "ester". In general, where the oxygen atom of the above formula is replaced by a sulfur atom, the formula represents a "thiocarbonyl" group. Where X is sulfur and R or R' is not hydrogen, the formula represents a "thioester". Where X is sulfur and R is hydrogen, the formula represents a "thiocarboxylic acid". Where X is sulfur and R' is hydrogen, the formula represents a "thioformate". Where X is a bond and R is not hydrogen, the above formula represents a "ketone". Where X is a bond and R is hydrogen, the above formula represents an "aldehyde".

The term "substituted carbonyl" refers to a carbonyl, as defined above, wherein one or more hydrogen atoms in R, R' or a group to which the moiety

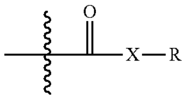

or

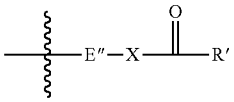

, is attached, are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for carbonyl and is defined more specifically by the formula $—R^{iv}COOH$, wherein $R^{iv}$ is a substituted or unsubstituted alkyl, a substituted or unsubstituted alkenyl, a substituted or unsubstituted alkynyl, a substituted or unsubstituted heterocyclyl, a substituted or unsubstituted alkylaryl, a substituted or unsubstituted arylalkyl, a substituted or unsubstituted aryl, a substituted or unsubstituted polyaryl, a substituted or unsubstituted polyheteroaryl, or a substituted or unsubstituted heteroaryl.

The term "substituted carboxyl" refers to a carboxyl, as defined above, wherein one or more hydrogen atoms in $R^{iv}$ are substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "phosphanyl" is represented by the formula

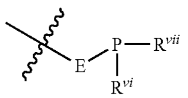

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted cycloalkyl, a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, $R^{vi}$ and $R^{vii}$ each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or $-(CH_2)_m-R'''$, or $R^{vi}$ and $R^{vii}$ taken together with the P atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "phosphonium" is represented by the formula

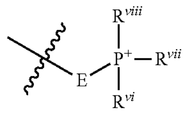

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted cycloalkyl, a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, $R^{vi}$, $R^{vii}$, and $R^{viii}$ each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or $-(CH_2)_m-R'''$, or $R^{vi}$, $R^{vii}$, and $R^{viii}$ taken together with the $P^+$ atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "phosphonyl" is represented by the formula

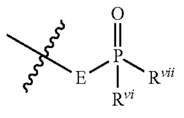

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, oxygen, alkoxy, aroxy, or substituted alkoxy or substituted aroxy, wherein, independently of E, $R^{vi}$ and $R^{vii}$ are independently a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or $-(CH_2)_m-R'''$, or $R^{vi}$ and $R^{vii}$ taken together with the P atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "substituted phosphonyl" represents a phosphonyl in which E, $R^{vi}$ and $R^{vii}$ are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "sulfinyl" is represented by the formula

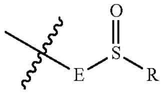

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted heterocyclyl, a substituted or unsubstituted polyaryl, a substituted or unsubstituted polyheteroaryl, wherein independently of E, R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a silyl, a thiol, an amido, an amino, or $—(CH_2)_m—R'''$, or E and R taken together with the S atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "sulfonyl" is represented by the formula

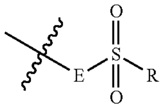

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted heterocyclyl, a substituted or unsubstituted polyaryl, a substituted or unsubstituted polyheteroaryl, wherein independently of E, R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or $—(CH_2)_m—R'''$, or E and R taken together with the S atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "substituted sulfonyl" represents a sulfonyl in which E, R, or both, are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, a substituted or unsubstituted polyaryl, a substituted or unsubstituted polyheteroaryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amino, substituted or unsubstituted cycloalkyl, substituted or unsubstituted heterocyclyl, substituted or unsubstituted aralkyl, substituted or unsubstituted alkylaryl, substituted or unsubstituted arylalkyl, substituted or unsubstituted aryl, substituted or unsubstituted heteroaryl, a substituted or unsubstituted polyaryl, a substituted or unsubstituted polyheteroaryl, $-(CH_2)_m-R'''$, R''' represents a hydroxy group, substituted or unsubstituted carbonyl group, an aryl, a cycloalkyl ring, a cycloalkenyl ring, a heterocycle, an amido, an amino, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

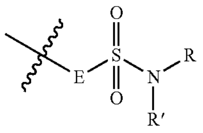

wherein E is absent, or E is substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted cycloalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, R and R' each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or $-(CH_2)_m-R'''$, or R and R' taken together with the N atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "silyl group" as used herein is represented by the formula —SiRR'R", where R, R', and R" can be, independently, a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl (e.g. a substituted or unsubstituted alkylaryl, a substituted or unsubstituted arylalkyl, etc.), a substituted or unsubstituted polyaryl, a substituted or unsubstituted polyheteroaryl, a substituted or unsubstituted carbonyl, a phosphonium, a phosphanyl, a phosphonyl, a sulfinyl, a thiol, an amido, an amino, an alkoxy, or an oxo, described above.

The terms "thiol" are used interchangeably and are represented by —SR, where R can be a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl (e.g. a substituted or unsubstituted alkylaryl, a substituted or unsubstituted arylalkyl, etc.), a substituted or unsubstituted polyaryl, a substituted or unsubstituted polyheteroaryl, a substituted or unsubstituted carbonyl, a phosphonium, a phosphanyl, an amido, an amino, an alkoxy, an oxo, a phosphonyl, a sulfinyl, or a silyl, described above.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to $-S-C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "hydroxyl" and "hydroxy" are used interchangeably and are represented by —OH.

The term "oxo" refers to =O bonded to a carbon atom.

The terms "cyano" and "nitrile" are used interchangeably to refer to —CN.

The term "nitro" refers to $—NO_2$.

The term "phosphate" refers to $—O—PO_3$.

The term "azide" or "azido" are used interchangeably to refer to $—N_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within the second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "substituted."

II. Compositions

Synthetic compounds (also referred to herein as "compounds") having antiallergic properties have been developed. These compounds have broad antiallergic properties and should be suitable for use in the prevention and/or treatment of multiple types of allergic reactions, allergic diseases, and/or inflammatory diseases, and/or amelioration of the symptom(s) of multiple types of allergic reactions, allergic diseases, and/or inflammatory diseases. In particular, these compounds are antagonists that have antagonistic activities against Mas-related G protein-coupled receptor (GPCR) X2 (MRGPRX2) and are suitable for use in the prevention and/or treatment of non-IgE mediated pseudo allergic reactions, allergic diseases, and/or inflammatory diseases.

Generally, the compounds contain two cyclic ring moieties, where each of the two cyclic ring moieties contains a fused ring structure that is optionally substituted with one or more functional groups. These compounds can bind MRGPRX2, block this receptor, and thus prevent the MCs activation. Without being bound to any theories, the overall structure of these compounds allows them to interact with multiple amino acids, such as at least 7 amino acids, at least 8 amino acids, at least 9 amino acids, or at least 10 amino acids, in the binding pocket of MRGPRX2 located in the N-terminal region and thus bind within the binding pocket with high affinity, such as a binding affinity of less than −9 kcal/mol, less than −10 kcal/mol, less than −10.5 kcal/mol, less than −11 kcal/mol, or less than −11.5 kcal/mol, in a range from −9 kcal/mol to −12.1 kcal/mol, from −10 kcal/mol to −12.1 kcal/mol, or from −10.5 kcal/mol to −12.1 kcal/mol, such as based on the docking methods described in the Examples.

Typically, the compounds meet at least two criteria of Lipinski's Rule of 5 for evaluating oral drugs, i.e. have a molecular weight of ≤500 Dalton, a Log Po/w≤5, H bond donor ≤5, and H bond acceptor ≤10. In some forms, the compounds meet all the criteria of Lipinski's Rule of 5.

Pharmaceutical compositions and formulations containing the compounds are also disclosed.

A. Compounds

1. Compound Structures

The compounds can have the structures of Formula I:

Formula I

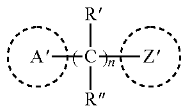

where n can be an integer from 0 to 6, from 0 to 5, from 0 to 4, from 0 to 3, from 0 to 2, or 0 or 1; where R' and R" can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where A' and Z' can be independently a substituted or unsubstituted polyaryl or a substituted or unsubstituted polyheteroaryl.

When R', R", A' and/or Z' are substituted functional groups, the substituents can be a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms of Formula I, wherein the compound has the structure of

Formula Ia

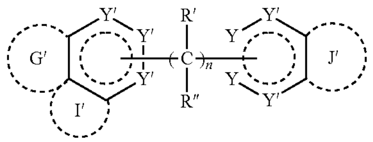

(a) where E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(b) where J' is a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(c) where each occurrence of Y' is independently $CR_1$, O, S, or $NR_2$, and at least one Y' is O, S, or $NR_2$, where $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (d) where the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

In some forms of Formula I, n is 0.

In some forms of Formula I, A' can have the structure of Formula II:

Formula II

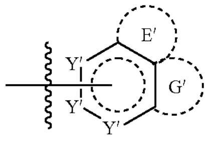

where E' and G' can be independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; where each occurrence of Y' is independently $CR_1$, O, S, or $NR_2$, where $R_1$ and $R_2$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and where the substituents can be any of the substituents described above for Formula I.

In some forms of Formula II, $R_1$ and $R_2$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula II, $R_1$ and $R_2$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula II, when E', G', $R_1$, and/or $R_2$ are substituted functional groups, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formula I, A' can have the structure of Formula III:

Formula III

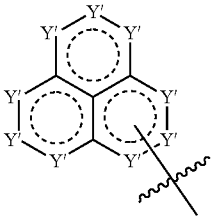

where Y' can be as defined above for Formula II and where at least one Y' is O, S, or $NR_2$ and $R_2$ is as defined above for Formula II.

In some forms of Formula I, A' can have the structure of Formula IVa or Formula IVb:

Formula IVa

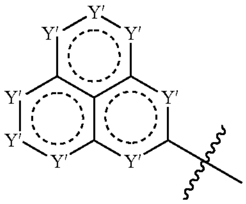

-continued

Formula IVb

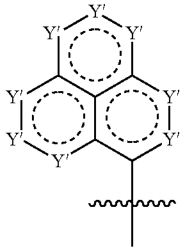

where Y' can be as defined above for Formula II and where at least one Y' is O, S, or $NR_2$ and $R_2$ is as defined above for Formula II.

In some forms of Formula I, A' can have the structure of Formula Va or Vb;

Formula Va

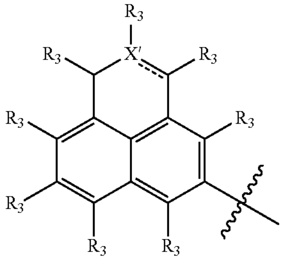

Formula Vb

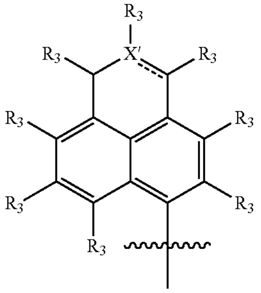

where X' can be C, N, O, or S, where each occurrence of $R_3$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and where the substituents can be any of the substituents described above for Formula I.

In some forms of Formula Va or Formula Vb, X' can be C or N and each occurrence of $R_3$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula Va or Formula Vb, X' can be C or N and each occurrence of $R_3$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula Va or Formula Vb, when $R_3$ is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formula I, Z' can have the structure of Formula VI:

Formula VI

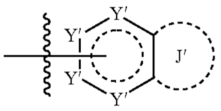

where Y' can be as defined above for Formula II and J' can be a substituted or unsubstituted heterocyclyl, a substituted or unsubstituted aryl, a substituted or unsubstituted heteroaryl, a substituted or unsubstituted polyaryl, or a substituted or unsubstituted polyheteroaryl.

In some forms of Formula VI, each occurrence of Y' can be $CR_1$ or $NR_2$, and $R_1$ and $R_2$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula VI, each occurrence of Y' can be $CR_1$ or $NR_2$, and $R_1$ and $R_2$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula VI, when J', $R_1$, and/or $R_2$ are substituted functional groups, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formula I, Z' can have the structure of Formula VII:

Formula VII

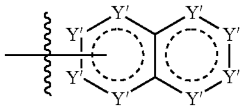

where Y' can be as defined above for Formula II and Formula VI.

In some forms of Formula I, Z' can have the structure of Formula VIII:

Formula VIII

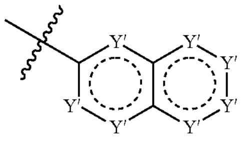

where Y' can be as defined above for Formula II and Formula VI.

In some forms of Formula I, Z' can have the structure of Formula IX:

Formula IX

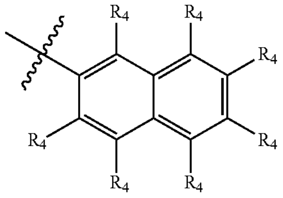

where each occurrence of $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and where the substituents can be any of the substituents described above for Formula I.

In some forms of Formula IX, each occurrence of $R_4$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula IX, each occurrence of $R_4$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula IX, when $R_4$ is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms, the compound can contain an A' of any one of Formulae II, III, IVa, IVb, Va, and Vb and a Z' of any one of Formulae VI, VII, VIII, and IX.

In some forms, the compound can have the structure of Formula Xa or Formula Xb:

Formula Xa

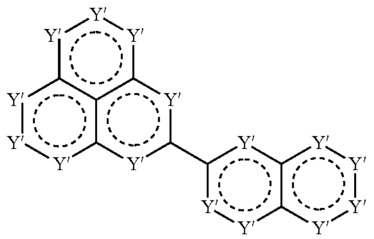

Formula Xb

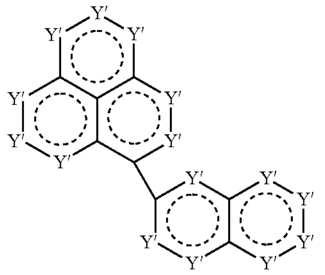

where Y' can be as defined above for Formula II and Formula VI.

In some forms, the compounds can have the structure of Formula XIa or Formula XIb:

Formula XIa

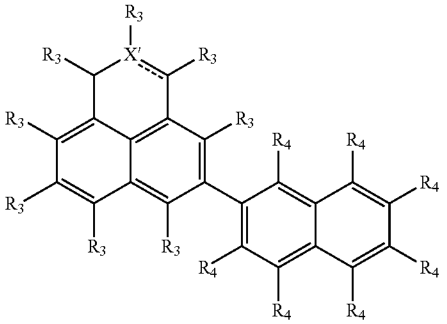

-continued

Formula XIb

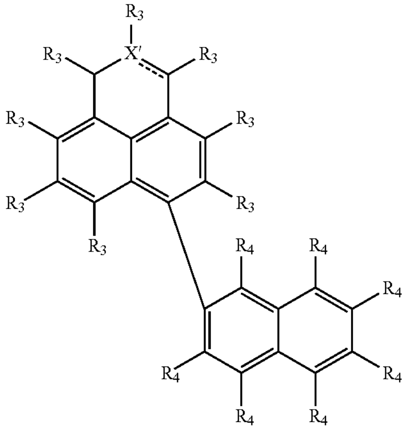

where X' can be C, N, O, or S, where each occurrence of $R_3$ and $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and where the substituents can be any of the substituents described above for Formula I.

In some forms of Formula XIa and Formula XIb, X' can be C or N and each occurrence of $R_3$ and $R_4$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XIa and Formula XIb, X' can be C or N and each occurrence of $R_3$ and $R_4$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XIa and Formula XIb, when $R_3$ and/or $R_4$ are/is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms, the compounds can have the structure of Formula XIIa or Formula XIIb:

Formula XIIa

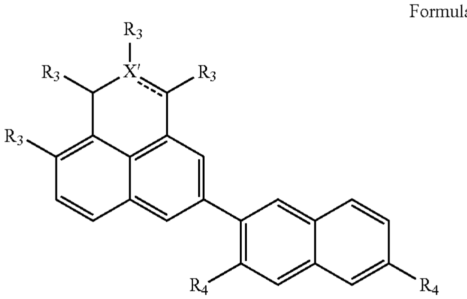

Formula XIIb

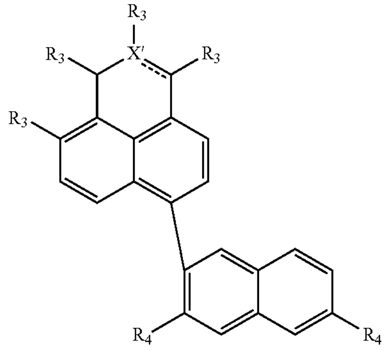

where X' can be C, N, O, or S, where each occurrence of $R_3$ and $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and where the substituents can be any of the substituents described above for Formula I.

In some forms of Formula XIIa and Formula XIIb, X' can be C or N and each occurrence of $R_3$ and $R_4$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XIIa and Formula XIIb, X' can be C or N and each occurrence of $R_3$ and $R_4$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XIIa and Formula XIIb, when $R_3$ and/or $R_4$ are/is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formulae XIa, XIb, XIIa, and XIIb, X' can be C or N, each occurrence of $R_3$ and $R_4$ can be independently a hydrogen, a substituted or unsubstituted alkyl, a substituted or unsubstituted aryl, an amino, an oxo, a halogen, a hydroxyl, a heterocyclic group,

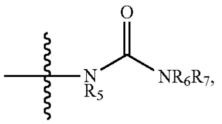

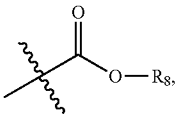

or

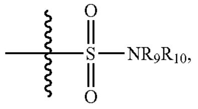

and $R_5$-$R_{10}$ can be independently a hydrogen, a substituted or unsubstituted alkyl, a substituted or unsubstituted aryl, an amino, or a halogen.

In some forms of Formulae XIa, XIb, XIIa, and XIIb, X' can be C or N, each occurrence of $R_3$ and $R_4$ can be independently a hydrogen, a substituted or unsubstituted alkyl, an oxo, a hydroxyl

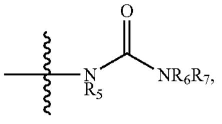

or

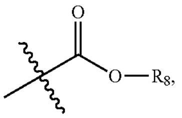

and $R_5$-$R_8$ can be independently a hydrogen or a substituted or unsubstituted alkyl.

In some forms of Formulae XIa, XIb, XIIa, and XIIb, X' can be C or N, each occurrence of $R_3$ can be independently a hydrogen, a substituted or unsubstituted alkyl, an oxo, a hydroxyl, or a carboxyl, each occurrence of $R_4$ can be independently a hydrogen,

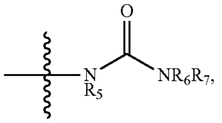

or

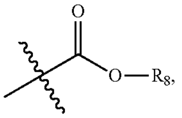

and $R_5$-$R_8$ can be independently a hydrogen or a substituted or unsubstituted alkyl.

For any of Formulae I, II, III, IVa, IVb, Va, Vb, VI, VII, VIII, IX, Xa, Xb, XIa, XIb, XIIa, and XIIb, the alkyl can be a linear alkyl, a branched alkyl, or a cyclic alkyl (either monocyclic or polycyclic). Exemplary alkyl includes a linear $C_1$-$C_{30}$ alkyl, a branched $C_4$-$C_{30}$ alkyl, a cyclic $C_3$-$C_{30}$ alkyl, a linear $C_1$-$C_{20}$ alkyl, a branched $C_4$-$C_{20}$ alkyl, a cyclic $C_3$-$C_{20}$ alkyl, a linear $C_1$-$C_{10}$ alkyl, a branched $C_4$-$C_{10}$ alkyl, a cyclic $C_3$-$C_{10}$ alkyl, a linear $C_1$-$C_6$ alkyl, a branched $C_4$-$C_6$ alkyl, a cyclic $C_3$-$C_6$ alkyl, a linear $C_1$-$C_4$ alkyl, cyclic $C_3$-$C_4$ alkyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ alkyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkyl group.

For any of Formulae I, II, III, IVa, IVb, Va, Vb, VI, VII, VIII, IX, Xa, Xb, XIa, XIb, XIIa, and XIIb, the alkenyl can be a linear alkenyl, a branched alkenyl, or a cyclic alkenyl (either monocyclic or polycyclic). Exemplary alkenyl includes a linear $C_1$-$C_{30}$ alkenyl, a branched $C_4$-$C_{30}$ alkenyl, a cyclic $C_3$-$C_{30}$ alkenyl, a linear $C_1$-$C_{20}$ alkenyl, a branched $C_4$-$C_{20}$ alkenyl, a cyclic $C_3$-$C_{20}$ alkenyl, a linear $C_1$-$C_{10}$ alkenyl, a branched $C_4$-$C_{10}$ alkenyl, a cyclic $C_3$-$C_{10}$ alkenyl, a linear $C_1$-$C_6$ alkenyl, a branched $C_4$-$C_6$ alkenyl, a cyclic $C_3$-$C_6$ alkenyl, a linear $C_1$-$C_4$ alkenyl, cyclic $C_3$-$C_4$ alkenyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ alkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group.

For any of Formulae I, II, III, IVa, IVb, Va, Vb, VI, VII, VIII, IX, Xa, Xb, XIa, XIb, XIIa, and XIIb, the alkynyl can be a linear alkynyl, a branched alkynyl, or a cyclic alkynyl (either monocyclic or polycyclic). Exemplary alkynyl includes a linear $C_1$-$C_{30}$ alkynyl, a branched $C_4$-$C_{30}$ alkynyl, a cyclic $C_3$-$C_{30}$ alkynyl, a linear $C_1$-$C_{20}$ alkynyl, a branched $C_4$-$C_{20}$ alkynyl, a cyclic $C_3$-$C_{20}$ alkynyl, a linear $C_1$-$C_{10}$ alkynyl, a branched $C_4$-$C_{10}$ alkynyl, a cyclic $C_3$-$C_{10}$ alkynyl, a linear $C_1$-$C_6$ alkynyl, a branched $C_4$-$C_6$ alkynyl, a cyclic $C_3$-$C_6$ alkynyl, a linear $C_1$-$C_4$ alkynyl, cyclic $C_3$-$C_4$ alkynyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ alkynyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkynyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkynyl group.

It is understood that any of the exemplary alkyl, alkenyl, and alkynyl groups can be heteroalkyl, heteroalkenyl, and heteroalkynyl, respectively. For example, the alkyl can be a linear $C_2$-$C_{30}$ heteroalkyl, a branched $C_4$-$C_{30}$ heteroalkyl, a cyclic $C_3$-$C_{30}$ heteroalkyl (i.e. a heterocycloalkyl), a linear $C_1$-$C_{20}$ heteroalkyl, a branched $C_4$-$C_{20}$ heteroalkyl, a cyclic $C_3$-$C_{20}$ heteroalkyl, a linear $C_1$-$C_{10}$ heteroalkyl, a branched $C_4$-$C_{10}$ heteroalkyl, a cyclic $C_3$-$C_{10}$ heteroalkyl, a linear $C_1$-$C_6$ heteroalkyl, a branched $C_4$-$C_6$ heteroalkyl, a cyclic $C_3$-$C_6$ heteroalkyl, a linear $C_1$-$C_4$ heteroalkyl, cyclic $C_3$-$C_4$ heteroalkyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ heteroalkyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group.

For any of Formulae I, II, III, IVa, IVb, Va, Vb, VI, VII, VIII, IX, Xa, Xb, XIa, XIb, XIIa, and XIIb, the alkenyl can be a linear $C_2$-$C_{30}$ heteroalkenyl, a branched $C_4$-$C_{30}$ heteroalkenyl, a cyclic $C_3$-$C_{30}$ heteroalkenyl (i.e., a heterocycloalkenyl), a linear $C_1$-$C_{20}$ heteroalkenyl, a branched $C_4$-$C_{20}$ heteroalkenyl, a cyclic $C_3$-$C_{20}$ heteroalkenyl, a linear $C_1$-$C_{10}$ heteroalkenyl, a branched $C_4$-$C_{10}$ heteroalkenyl, a cyclic $C_3$-$C_{10}$ heteroalkenyl, a linear $C_1$-$C_6$ heteroalkenyl, a branched $C_4$-$C_6$ heteroalkenyl, a cyclic $C_3$-$C_6$ heteroalkenyl, a linear $C_1$-$C_4$ heteroalkenyl, cyclic $C_3$-$C_4$ heteroalkenyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ heteroalkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group.

For any of Formulae I, II, III, IVa, IVb, Va, Vb, VI, VII, VIII, IX, Xa, Xb, XIa, XIb, XIIa, and XIIb, the alkynyl can be a linear $C_2$-$C_{30}$ heteroalkynyl, a branched $C_4$-$C_{30}$ heteroalkynyl, a cyclic $C_3$-$C_{30}$ heteroalkynyl (i.e., a heterocycloalkynyl), a linear $C_1$-$C_{20}$ heteroalkynyl, a branched $C_4$-$C_{20}$ heteroalkynyl, a cyclic $C_3$-$C_{20}$ heteroalkynyl, a linear $C_1$-$C_{10}$ heteroalkynyl, a branched $C_4$-$C_{10}$ heteroalkynyl, a cyclic $C_3$-$C_{10}$ heteroalkynyl, a linear $C_1$-$C_6$ heteroalkynyl, a branched $C_4$-$C_6$ heteroalkynyl, a cyclic $C_3$-$C_6$ heteroalkynyl, a linear $C_1$-$C_4$ heteroalkynyl, cyclic $C_3$-$C_4$ heteroalkynyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ heteroalkynyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkynyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkynyl group.

For any of Formulae I, II, III, IVa, IVb, Va, Vb, VI, VII, VIII, IX, Xa, Xb, XIa, XIb, XIIa, and XIIb, the aryl group can be a $C_5$-$C_{30}$ aryl, a $C_5$-$C_{20}$ aryl, a $C_5$-$C_{12}$ aryl, a $C_5$-$C_{11}$ aryl, a $C_5$-$C_9$ aryl, a $C_6$-$C_{20}$ aryl, a $C_6$-$C_{12}$ aryl, a $C_6$-$C_{11}$ aryl, or a $C_6$-$C_9$ aryl. It is understood that the aryl can be a heteroaryl, such as a $C_5$-$C_{30}$ heteroaryl, a $C_5$-$C_{20}$ heteroaryl, a $C_5$-$C_{12}$ heteroaryl, a $C_5$-$C_{11}$ heteroaryl, a $C_5$-$C_9$ heteroaryl, a $C_6$-$C_{30}$ heteroaryl, a $C_6$-$C_{20}$ heteroaryl, a $C_6$-$C_{12}$ heteroaryl, a $C_6$-$C_{11}$ heteroaryl, or a $C_6$-$C_9$ heteroaryl. The polyaryl group can be a $C_{10}$-$C_{30}$ polyaryl, a $C_{10}$-$C_{20}$ polyaryl, a $C_{10}$-$C_{12}$ polyaryl, a $C_{10}$-$C_{11}$ polyaryl, or a $C_{12}$-$C_{20}$ polyaryl. It is understood that the aryl can be a polyheteroaryl, such as a $C_{10}$-$C_{30}$ polyheteroaryl, a $C_{10}$-$C_{20}$ polyheteroaryl, a $C_{10}$-$C_{12}$ polyheteroaryl, a $C_{10}$-$C_{11}$ polyheteroaryl, or a $C_{12}$-$C_{20}$ polyheteroaryl.

The compounds may contain one or more chiral centers or may otherwise be capable of existing as multiple stereoisomers. These may be pure (single) stereoisomers or mixtures of stereoisomers, such as enantiomers, diastereomers, and enantiomerically or diastereomerically enriched mixtures. The compounds may be capable of existing as geometric isomers. Accordingly, it is to be understood that the present invention includes pure geometric isomers or mixtures of geometric isomers.

2. Exemplary Compounds

Exemplary compounds are presented below.

GE0117

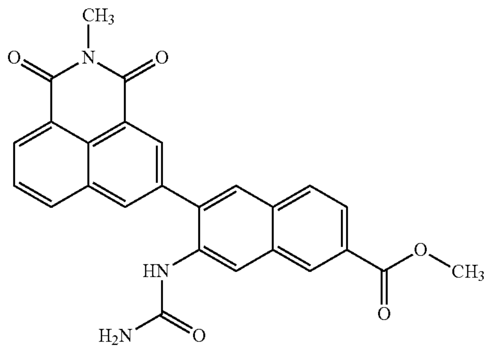

GE0118

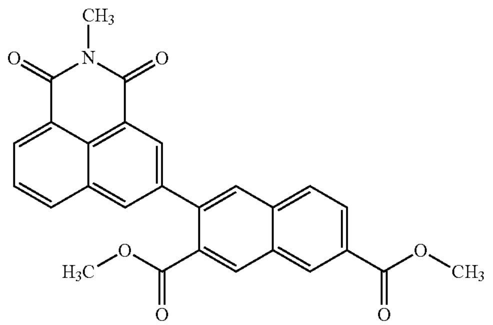

-continued

GE0119

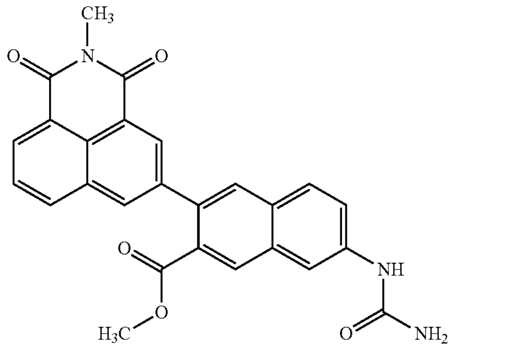

GE1109

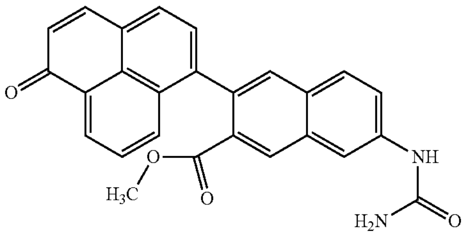

GE1110

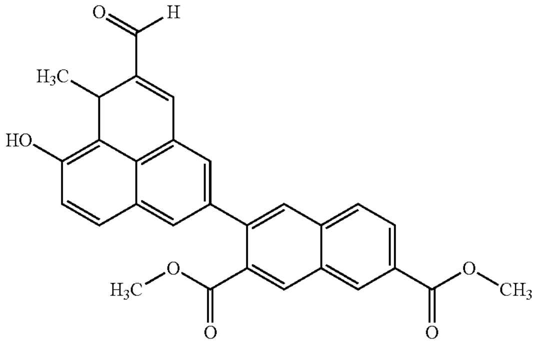

GE1111

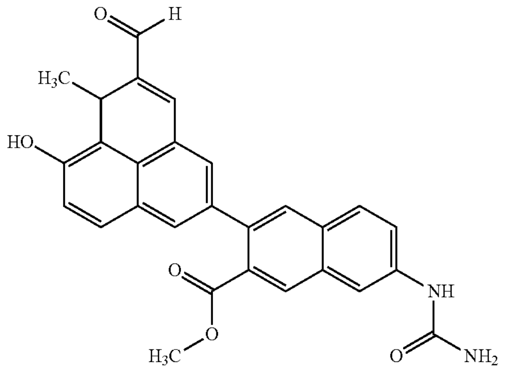

3. Pharmaceutically Acceptable Salts

The compounds may be neutral or may be one or more pharmaceutically acceptable salts, crystalline forms, non crystalline forms, hydrates, or solvates, or a combination thereof. References to the compounds may refer to the neutral molecule, and/or those additional forms thereof collectively and individually from the context. Pharmaceutically acceptable salts of the compounds include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

B. Pharmaceutical Compositions

Pharmaceutical compositions and pharmaceutical formulations in unit dosage form (also referred herein as "pharmaceutical formulations") suitable for the delivery of the compounds thereof and their preparation are disclosed. Generally, the pharmaceutical composition or formulation contains the compounds and/or the pharmaceutically acceptable salts of the compounds described herein and a pharmaceutically acceptable excipient. The term "pharmaceutically acceptable excipient" is used herein to describe any ingredient in the formulation other than the compounds described herein. The pharmaceutical compositions or formulations can include an effective amount of one or more compounds of any of the formulae described herein and/or their pharmaceutically acceptable salts, including any one or any combination of compounds of the formulae described herein and/or their pharmaceutically acceptable salts, for preventing or treating a pseudo allergic reaction, a pseudo allergic disease, or a pseudo inflammatory disease, or treating or ameliorating one or more symptoms associated with a pseudo allergic reaction, a pseudo allergic disease, or a pseudo inflammatory disease in a subject in need thereof. It is to be understood that combinations and/or mixtures of the compounds and/or their pharmaceutically acceptable salts may be included in the composition or formulation.

In some forms, the pharmaceutical composition or formulation can further contain one or more active agents in addition to the compounds, such as one or more additional antiallergic agents.

Any one of more of the compounds provided herein can be expressly included or expressly excluded from the pharmaceutical compositions, dosage units, and/or methods of use or treatment disclosed herein.

1. Oral Formulations

The compounds and/or their pharmaceutically acceptable salts can be administered orally. Oral administration may involve swallowing so that the compound enters the gastrointestinal tract, or buccal or sublingual administration may be employed by which the compound enters the bloodstream directly from the mouth.

Formulations suitable for oral administration include solid formulations such as tablets, capsules containing particulates, liquids, powders, lozenges (including liquid-filled lozenges), chews, multi- and nano-particulates, gels, solid solutions, liposomes, films, ovules, sprays and liquid formulations.

Liquid formulations include suspensions, solutions, syrups and elixirs. Such formulations may be employed as fillers in soft or hard capsules and typically contain a carrier, for example, water, ethanol, polyethylene glycol, propylene glycol, methylcellulose or a suitable oil, and one or more emulsifying agents and/or suspending agents. Liquid formulations may also be prepared by the reconstitution of a solid, for example, from a sachet.

The compounds and/or their pharmaceutically acceptable salts may also be used in fast dissolving, fast-disintegrating dosage forms such as those described in *Expert Opinion in Therapeutic Patents,* 11 (6), 981-986, by Liang and Chen (2001).

For tablet or capsule dosage forms, depending on dose, the compounds and/or their pharmaceutically acceptable salts may make up from 1 weight % to 80 weight % of the dosage form, more typically from 5 weight % to 60 weight % of the dosage form. In addition to the compounds described herein, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will contain from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (as, for example, the monohydrate, spray-dried monohydrate or anhydrous form), mannitol, xylitol, dextrose, sucrose, sorbitol, microcrystalline cellulose, starch and dibasic calcium phosphate dihydrate.

Tablets or capsules may also optionally contain surface active agents, such as sodium lauryl sulfate and polysorbate 80, and glidants such as silicon dioxide and talc. When present, surface active agents may contain from 0.2 weight % to 5 weight % of the tablet, and glidants may contain from 0.2 weight % to 1 weight % of the tablet.

Tablets or capsules also generally contain lubricants such as magnesium stearate, calcium stearate, zinc stearate, sodium stearyl fumarate, and mixtures of magnesium stearate with sodium lauryl sulphate. Lubricants generally contain from 0.25 weight % to 10 weight %, preferably from 0.5 weight % to 3 weight % of the tablet.

Other possible ingredients include glidants (e.g. Talc or colloidal anhydrous silica at about 0.1 weight % to about 3 weight %), antioxidants, colorants, flavouring agents, preservatives and taste-masking agents.

Exemplary tablets contain up to about 80% of one or more of the compounds described herein, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet or capsule blends may be compressed directly or by roller to form tablets. Tablet or capsule blends or portions of blends may alternatively be wet-, dry-, or melt-granulated, melt congealed, or extruded before tableting. The final formulation may contain one or more layers and may be coated or uncoated; it may even be encapsulated.

Solid formulations for oral administration may be formulated to be immediate and/or modified release. Modified release formulations include delayed, sustained, pulsed, controlled, targeted and programmed release formulations.

2. Parenteral Formulations

The compounds and/or their pharmaceutically acceptable salts can also be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intramuscular, and subcutaneous delivery. Suitable means for parenteral administration include needle (including microneedle) injectors, needle-free injectors, and infusion techniques.

Parenteral formulations are typically aqueous solutions which may contain excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of the compounds used in the preparation of a parenteral formulation may be increased by the use of appropriate formulation techniques, such as the incorporation of solubility-enhancing agents.

Formulations for parenteral administration may be formulated to be immediate and/or modified release. Modified release formulations include delayed, sustained, pulsed, controlled, targeted and programmed release formulations. Thus, the compounds may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

3. Pulmonary and Mucosal Formulations

The compounds and/or their pharmaceutically acceptable salts can be formulated for pulmonary or mucosal administration. The administration can include delivery of the composition to the lungs, nasal, oral (sublingual, buccal), vaginal, or rectal mucosa.

For example, the compounds can also be administered intranasally or by oral inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as water, ethanol-water mixture, 1,1,1,2-tetrafluoroethane or 1,1,1,2,3,3,3-heptafluoropropane. For intranasal or oral inhalation use, the powder may contain a bioadhesive agent, for example, chitosan or cyclodextrin. The term aerosol as used herein refers to any preparation of a fine mist of particles, which can be in solution or a suspension, whether or not it is produced using a propellant. Aerosols can be produced using standard techniques, such as ultrasonication or high-pressure treatment.

The pressurized container, pump, spray, atomizer, or nebulizer contains a solution or suspension of one or more of the compounds including, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, a drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compounds described herein, a suitable powder base such as lactose or starch and a performance modifier such as 1-leucine, mannitol, or magnesium stearate. The lactose may be anhydrous or in the form of a monohydrate, preferably the latter. Other suitable excipients include dextran, glucose, maltose, sorbitol, xylitol, fructose, sucrose, and trehalose.

A suitable solution formulation for use in an atomizer using electrohydrodynamics to produce a fine mist may contain from 1 μg to 20 mg of one or more of the compounds per actuation and the actuation volume may vary from 1 μl to 100 μl. A typical formulation may contain one or more of the compounds described herein, propylene glycol, sterile water, ethanol and sodium chloride. Alternative solvents that may be used instead of propylene glycol include glycerol and polyethylene glycol.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, PGLA. Modified release formulations include delayed, sustained, pulsed, controlled, targeted, and programmed release formulations.

In the case of dry powder inhalers and aerosols, the dosage unit is determined by means of a valve which delivers a metered amount. Units in accordance with the compounds are typically arranged to administer a metered dose or "puff". The overall daily dose will be administered in a single dose or, more usually, as divided doses throughout the day.

In some forms, the compounds and/or their pharmaceutically acceptable salts can be formulated for pulmonary delivery, such as intranasal administration or oral inhalation. Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into an aqueous solution, e.g., water or isotonic saline, buffered or un-buffered, or as an aqueous suspension, for intranasal administration as drops or as a spray. Such aqueous solutions or suspensions may be isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. One skilled in the art can readily determine a suitable saline content and pH for an innocuous aqueous solution for nasal and/or upper respiratory administration.

In some forms, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In some forms, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In some forms, the pharmaceutical compositions may contain minor amounts of polymers, surfactants, or other excipients well known to those of the art. In this context, "minor amounts" means no excipients are present that might affect or mediate uptake of the compounds by cells and that the excipients that are present in amount that do not adversely affect uptake of compounds by cells.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

4. Topical Formulations

The compounds and/or their pharmaceutically acceptable salts can be administered directly to the external surface of the skin or the mucous membranes (including the surface membranes of the nose, lungs and mouth), such that the compounds and/or their pharmaceutically acceptable salts cross the external surface of the skin or mucous membrane and enters the underlying tissues.

Formulations for topical administration generally contain a dermatologically acceptable carrier that is suitable for application to the skin, has good aesthetic properties, is compatible with the active agents and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurized aerosol containers using conventional propellants. These carriers can also be delivered in the form of a mousse or a transdermal patch. Other suitable topical carriers include anhydrous liquid solvents such as oils, alcohols, and silicones (e.g., mineral oil, ethanol isopropanol, dimethicone, cyclomethicone, and the like); aqueous-based single phase liquid solvents (e.g., hydro-alcoholic solvent systems, such as a mixture of ethanol and/or isopropanol and water); and thickened versions of these anhydrous and aqueous-based single phase solvents (e.g. where the viscosity of the solvent has been increased to form a solid or semi-solid by the addition of appropriate gums, resins, waxes, polymers, salts, and the like). Examples of topical carrier systems useful in the present formulations are described in the following four references all of which are incorporated herein by reference in their entirety: "Sun Products Formulary" Cosmetics & Toiletries, vol. 105, pp. 122-139 (December 1990); "Sun Products Formulary," Cosmetics & Toiletries, vol. 102, pp. 117-136 (March 1987); U.S. Pat. No. 5,605,894 to Blank et al., and U.S. Pat. No. 5,681,852 to Bissett.

Formulations for topical administration may be formulated to be immediate and/or modified release. Modified release formulations include delayed, sustained, pulsed, controlled, targeted and programmed release formulations. Thus, the compounds may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

5. Additional Active Agent(s)

In some forms, the pharmaceutical composition or pharmaceutical formulation can include one or more additional active agents, such as one or more additional antiallergic and/or anti-inflammatory agents. Antiallergic and anti-inflammatory agents that can be included in the pharmaceutical compositions or formulations are known, for example, see the WebMD, "Allergy Medications" and "Anti-inflammatory Drugs," website https://www.webmd.com/allergies/allergy-medications, and https://www.webmd.com/arthritis/anti-inflammatory-drugs; Barnes, *Nature,* 402(6760): 31-38 (1999); Rainsford, *Inflammation in the pathogenesis of chronic diseases* 3:27 (2007); Chinose, *Antiallergic drugs.* In D. Spina, C. Page, W. Metzger, & B. O'Connor (Eds.), Drugs for the Treatment of Respiratory Diseases, 119-123, Cambridge: Cambridge University Press; and Assanasen, *Clin. Allergy Immunol.,* 17:101-139 (2002).

Exemplary antiallergic and anti-inflammatory drugs that can be included in the pharmaceutical composition or pharmaceutical formulation include, but are not limited to, epinephrine, antihistamines, corticosteroids, non-steroid agents, and antibodies, such as (S)-carbinoxamine maleate, 2',4,4',6'-tetrahydroxychalcone, 2',4,4',6'-tetrahydroxychalcone(1-), 6'-O-acetylpaeoniflorin, 7-epiclusianone, trans-rhaponticin, acroptilin, alcaftadine, amlexanox, aspirin-triggered resolvin D1, astemizole, azatadine, azatadine maleate, azelastine, azelastine hydrochloride, bepotastine, bepotastine besylate, Breo Ellipta, brompheniramine, brompheniramine maleate, capsiate, carbinoxamine, carbinoxamine maleate, cetirizine, chlorphenamine, cinnarizine, clemastine, clemastine fumarate, cortisol, cyproheptadine, cyproheptadine hydrochloride, davidigenin, desloratadine, dexbrompheniramine, dexbrompheniramine maleate, dichotomoside D, diphenhydramine, diphenhydramine hydrochloride, diphenhydramine salicylate, dithiadene, doxylamine, emedastine, emedastine difumarate, epinastine, fexofenadine, fluticasone, fluticasone furoate, fluticasone propionate, fucodiphloroethol G, ginsenoside C—K, hydrangenol, jaceosidin, methapyrilene, methapyrilene hydrochloride, mometasone, mometasone furoate, myricitrin, nedocromil, petasin, prednisolone sodium phosphate, promethazine, promethazine hydrochloride, rhinacanthin D, rhodiocyanoside A, rottlerin, sappanchalcone, secoxyloganin, tixocortol pivalate, torososide B, tranilast, triamcinolone, triamcinolone acetonide, Δ9-tetrahydrocannabinolic acid, β-lapachone, β-myrcene, (−)-antofine, (−)-cubebin, (−)-larreatricin, (−)-syringaresinol O,O'-bis(β-D-glucoside), (+)-α-viniferin, (+)-conocarpan, (+)-schisandrin B, (+)-subersic acid, (10E,12Z,15Z)-9-hydroxy-10,12,15-octadecatrienoic acid methyl ester, (13R,14S)-dihydroxy-(4Z,7Z,9E,11E,16Z,19Z)-docosahexaenoic acid, (18R)-resolvin E3, (18S)-resolvin E1, (18S)-resolvin E2, (1R,5R,6S,7R,8S,10R)-8-hydroxy-4-oxopseudoguai-2(3),11(13)-dien-12,6-olide, (1R,5R,6S,7S,8S,10R,11S)-6-hydroxy-4-oxopseudoguai-2(3)-en-12,8-olide, (1S,2R,5R,6S,7R,8S,10R)-6-acetoxy-2-methoxy-4-oxopseudoguai-11(13)-en-12,8-olide, (1S,2R,5R,6S,7S,8S,10R)-6-hydroxy-2-ethoxy-4-oxopseudoguai-11(13)-en-12,8-olide, (1S,2R,5R,6S,7S,8S,10R)-6-hydroxy-2-methoxy-4-oxopseudoguai-11(13)-en-12,8-olide, (1S,2S,5R,6S,7R,8S,10R)-6-acetoxy-2-methoxy-4-oxopseudoguai-11(13)-en-12,8-olide, (1S,5R,6S,7S,8S,10R,11R)-6-hydroxy-4-oxopseudoguai-12,8-olide, (1S,5S,7R,8S,10R)-14-acetoxy-4-oxopseudoguai-11(13)-en-12,8-olide, (2S,3S)-2,3-dihydro-3-hydroxymethyl-2-(4-hydroxyphenyl)-5-(E)-propenylbenzofuran, (4Z,7Z,10S,11E,13Z,15E,17S,19Z)-10,17-dihydroxydocosahexaenoic acid, (4Z,7Z,10Z,12E,14R,16Z,19Z)-14,22-dihydroxydocosahexaenoic acid, (4Z,7Z,10Z,12E,14S,16Z,19Z)-14,22-dihydroxydocosahexaenoic acid, (4Z,7Z,10Z,13Z,15E,19Z)-17-oxodocosahexaenoic acid, (5Z)-5-(quinoxalin-6-ylmethylidene)-1,3-thiazolidine-2,4-dione, (5Z,11Z,14Z)-icosatrienoic acid, (7R,14S)-dihydroxy-(4Z,8E,10E,12Z,16Z,19Z)-docosahexaenoic acid, (7R,14S)-dihydroxy-(8E,10E,12Z,16Z,19Z)-docosapentaenoic acid, (E)-2,3,5,4'-tetrahydroxystilbene-2-O-β-D-glucoside, (E,E)-germacrone, (R)-lisofylline, (RS)-mallotophilippen E, (S)-colchicine, 1,3,7,9-tetramethyluric acid, 1-O-3,4-dimethoxy-5-hydroxyphenyl-(6-O-3,5-dimethoxygalloyl)-β-D-glucopyranoside, 1-O-3,4-dimethoxy-5-hydroxyphenyl-(6-O-vanilloyl)-β-D-glucopyranoside, 10-PAHSA, 10-PAHSA(1-), 11(R)-HEPE, 11(R)-HEPE(1-), 11-PAHSA, 11-PAHSA(1-), 12-PAHSA, 12-PAHSA(1-), 13,14(S)-dihydroxy-(7Z,9E,11E,16Z,19Z)-docosapentaenoic acid, 13-PAHSA, 13-PAHSA(1-), 14(S),21-dihydroxy-(7Z,10Z,12E,16Z,19Z)-docosapentaenoic acid, 15(R)-HEPE, 15(R)-HEPE(1-), 16(S)-HETE, 16,23,29-trihydroxy-3-oxo-olean-12-en-28-oic acid, 17-defurano-17-oxosalannin, 18(R)-HEPE, 18(R)-HEPE(1-), 18(S)-HEPE, 19α-hydroxyasiatic acid, 2α,3α,23-trihydroxyolean-12-en-28-oic acid, 2α,3β-dihydroxyolean-13(18)-en-28-oic acid, 2α-acetoxy-4α,6α-dihydroxy-1β,5αH-guai-9(10),11(13)-dien-12,8alpha-olide, 2',4,4',6'-tetrahydroxychalcone, 2',4,4',6'-tetrahydroxychalcone(1-), 2'-hydroxychalcone, 2'-hydroxydaidzein, 2'-hydroxydaidzein(1-), 2'-hydroxyformononetin, 2,4-dihydroxy-6-methylbenzaldehyde, 2-(β-D-glucopyranosyloxy)benzoic acid, 2-(2,4-dihydroxyphenyl)-5-(E)-propenylbenzofuran, 2-(2-hydroxy-4-methoxyphenyl)-5-(3-hydroxypropyl)benzofuran, 2-(4-hydroxyphenyl)-5-(E)-propenylbenzofuran, 2-acetamidophenol, 22-hydroxyprotectin D1, 3β,6β,23-trihydroxyolean-12-en-28-oic acid, 3β,6β,23-trihydroxyolean-12-en-28-oic acid 28-O-β-D-glucopyranoside, 3,4'-dimethylkaempferol, 3-O-[2,3-di-O-acetyl-α-L-arabinopyranosyl]-hederagenin 28-O-α-L-rhamnopyranosyl-(1→4)-β-D-glucopyranosyl-(1→6)-β-D-glucopyranoside, 3-O-[3,4-di-O-acetyl-α-L-arabinopyranosyl]hederagenin 28-O-α-L-rhamnopyranosyl-(1→4)-β-D-glucopyranosyl-(1→6)-β-D-glucopyranoside, 3-deacetylsalannin, 4β,10α-dihydroxy-5αH-guai-1(2),11(13)-dien-12,8α-olide, 4',6,7-trihydroxyisoflavone, 4'-hydroxychalcone, 4-epiisoinuviscolide, 4-hydroxycordoin, 4-terpineol, 5-(3-hydroxypropyl)-2-(2-methoxy-4-hydroxyphenyl)benzofuran, 5-PAHSA, 5-PAHSA(1-), 6'-O-acetylpaeoniflorin, 6,7-dihydroxy-4-methylcoumarin, 7α-hydroxydehydroepiandrosterone, 7-deacetylgedunin, 7-epiclusianone, 7-oxo-10α-cucurbitadienol, 7-PAHSA, 7-PAHSA(1-), 8-epihelenalin, 8-epiinuviscolide, 8-oxoresolvin D1, 8-PAHSA, 8-PAHSA(1-), 9-PAHSA, 9-PAHSA(1-), 9E,11E-octadecadienoic acid, all-trans-retinoic acid, Aloe C-glucosylchromone, epi-maslinic acid, meso-3,3'-didemethoxynectandrin B, meso-zeaxanthin, N-arachidonoylserotonin, rac-lisofylline, rel-2α,3α,23-trihydroxy-19-oxo-18,19-seco-urs-11,13(18)-dien-28-oic acid, rel-2α,3β,23-trihydroxy-19-oxo-18,19-seco-12,17-dien-28-norursane, trans-rhaponticin, absinthin, acteoside, afzelin, agnuside, antrocapmphin A, aromaticin, ascidiathiazone A, ascidiathiazone B, aspirin-triggered protectin D1, aspirin-triggered resolvin D1, aspirin-triggered resolvin D2, aspirin-triggered resolvin D3, aspirin-triggered resolvin D4, aspirin-triggered resolvin D5, aspirin-triggered resolvin D6, astilbin, astragaloside IV, azadiradione, baicalein, bauhinoxepin F, bauhinoxepin I, BAY 60-6583, beraprost, beraprost sodium, betamethasone phosphate, betulin, betulinic acid, bixin, bowdichione, brazilein, brazilin, bufalin, burrodin, butrin, cafestol, camostat, camostat mesylate, cannabigerol, capsiate, carlinoside, carnosic acid, carpesiolin, castanospermine, cauloside D, cenicriviroc, CGP-42112A, CGS-21680, chrysin, chrysophanol, clarinoside, cleomiscosin A, columbianadin, conferol A, conferol B, confertin, CORM 3, coumestrol, crassumolide A, cryogenine, cryptolepine, cudraflavone B, cudratricusxanthone A, curcumin, cyclo(L-His-L-Pro), cyclomontanin A, cyclomontanin C, cyclomontanin D, decane-1,2-diol, decanoic acid, dehydrodiconiferyl alcohol, demethoxycurcumin, demethylzeylasteral, diallyl trisulfide, diinsinin, diinsininol, dioscin, (−)-β-caryophyllene, (2S)-2-(4-{[(1R,2S)-2-hydroxycyclopentyl]methyl}phenyl)propanoic acid, (E)-3-tosylacrylonitrile, (S)-ketorolac, 4-(methylamino)antipyrine, 4-aminoantipyrine, O-methylsalicylic acid, [5-fluoro-1-(4-isopropylbenzylidene)-2-methylinden-3-yl]acetic acid, aceclofenac, acemetacin, acetosyringone, acetylsalicylic acid, adapalene, alclofenac, alminoprofen, almotriptan, almotriptan malate, amfenac, amfenac sodium hydrate, aminophenazone, amlexanox, amodiaquine, ampiroxicam, antipyrine, apazone, apigenin 7-O-β-D-glucoside, apigenin 7-O-β-D-glucoside(1-), apocynin, apremilast, arasertaconazole, baicalin, balsalazide, balsalazide disodium, bendazac, benoxaprofen, benzydamine, biphenyl-4-ylacetic acid, bromfenac, bromfenac sodium salt, bromfenac sodium salt sesquihydrate, bufexamac, bumadizone, bumadizone calcium, bumadizone calcium hemihydrate, carprofen, cimicoxib, clofazimine, clonixin, clonixin lysine salt, corilagin, crisaborole, deracoxib, dexibuprofen, dexketoprofen, diclofenac, difenpiramide, diflunisal, dithiosalicylic acid, droxicam, eletriptan, eletriptan hydrobromide, enprofylline, etodolac, etoricoxib, fenbufen, fendosal, fenoprofen, fenoprofen calcium, firocoxib, flufenamate, flufenamic acid, flunixin, flunixin meglumine, flunoxaprofen, flurbiprofen, garenoxacin, glafenine, ibufenac, and ibuprofen, and a combination thereof.

6. Effective Amount

Effective amount of the compounds contained in the pharmaceutical composition or pharmaceutical formulation depend on many factors, including the indication being treated, the route of administration, co-administration of other therapeutic compositions, and the overall condition of the patient. Exemplary effective amount of the compounds contained in the pharmaceutical formulation (in unit dosage form) can be from 0.01 mg to 1500 mg, from 0.1 mg to 1500 mg, from 1 mg to 1500 mg, from 10 mg to 1500 mg, from 20 mg to 1500 mg, from 0.01 mg to 1000 mg, from 0.1 mg to 1000 mg, from 1 mg to 1000 mg, from 10 mg to 1000 mg, from 20 mg to 1000 mg, from 0.01 mg to 700 mg, from 0.1 mg to 700 mg, from 1 mg to 700 mg, from 10 mg to 700 mg, from 20 mg to 700 mg, from 50 mg to 700 mg, from 0.01 mg to 500 mg, from 0.1 mg to 500 mg, from 1 mg to 500 mg, from 10 mg to 500 mg, from 20 mg to 500 mg, from 50 mg to 500 mg, from 0.01 mg to 100 mg, or from 0.1 mg to 100 mg.

In some forms, the total concentration of the one or more compounds in the pharmaceutical formulation is in a range from about 0.05 wt % to about 20 wt %, from about 0.1 wt % to about 20 wt %, from about 0.1 wt % to about 15 wt %, from about 0.2 wt % to about 20 wt %, from about 0.1 wt % to about 10 wt %, from about 0.5 wt % to about 20 wt %, from about 0.5 wt % to about 15 wt %, from about 0.5 wt % to about 10 wt %, from about 0.5 wt % to about 5 wt %, from about 0.1 wt % to about 5 wt %, or from about 0.1 wt % to about 1 wt %. The term 'total concentration of the one or more compounds in the pharmaceutical formulation" refers to the total weight of the one or more compounds relative to the weight of the pharmaceutical formulation.

III. Methods of Making

Methods of making the compounds are disclosed. Generally, the method includes (i) mixing a reactant mixture and a catalyst to form a reaction mixture, where the reactant mixture comprises a first reactant, a second reactant, and a solvent; and (ii) heating the reaction mixture at a suitable temperature for a period of time sufficient to form a product containing the compound of any one of Formulae I-XIIb. Step (i) can be performed prior to or simultaneously with step (ii). In some forms, the reactant mixture further includes a base, such as sodium carbonate, potassium carbonate, caesium carbonate, tri-potassium phosphate, sodium bicarbonate, or potassium hydroxide, or a combination thereof.

In some forms, the first reactant can have the structure of Formula XIII:

Formula XIII

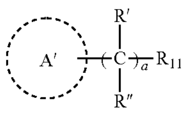

where a can be an integer from 0 to 6, from 0 to 5, from 0 to 4, from 0 to 3, from 0 to 2, or 0 or 1; where R' and R" can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where A' can be a substituted or unsubstituted polyaryl or a substituted or unsubstituted polyheteroaryl; and where Rn can be a leaving group.

In some forms of Formula XIII, a is 0.

In some forms of Formula XIII, $R_{11}$ can be a halogen, such as fluorine, bromine, chlorine, or iodine, dinitrogen, di-alkyl ether, per-fluoroalkylsulfonates, tosylates, mesylates, sulfonates, alcohols, nitrate, phosphate, inorganic esters, thioehter, amino, carboxylate, phenoxides, hydroxide, alkoxyl, amido, hydride, arenide, alkanide, or have the structure of Formula XIV:

Formula XIV

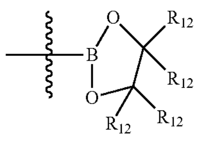

where each occurrence of $R_{12}$ can be independently a hydrogen or a substituted or unsubstituted alkyl, such as a substituted or unsubstituted $C_1$-$C_{15}$ alkyl, a substituted or unsubstituted $C_1$-$C_{12}$ alkyl, a substituted or unsubstituted $C_1$-$C_{10}$ alkyl, a substituted or unsubstituted $C_1$-$C_8$ alkyl, a substituted or unsubstituted $C_1$-$C_6$ alkyl, a substituted or unsubstituted $C_1$-$C_5$ alkyl, a substituted or unsubstituted $C_1$-$C_4$ alkyl, a substituted or unsubstituted $C_1$-$C_3$ alkyl, or a substituted or unsubstituted $C_1$-$C_2$ alkyl, such as a methyl or ethyl.

In some forms of Formula XIII, $R_{11}$ can be a halogen, such as bromine. In some forms of Formula XIII, $R_{11}$ can have the structure of Formula XIV.

When R', R", A' and/or $R_{12}$ are substituted functional groups, the substituents can be a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms, the first reactant can have the structure of Formula XV:

Formula XV

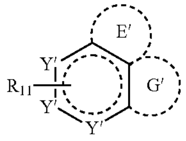

where E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; where each occurrence of Y' is independently $CR_1$, O, S, or $NR_2$, where $R_1$ and $R_2$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where $R_{11}$ can be as defined above for Formula XIII, and where the substituents can be any of the substituents described above for Formula I.

In some forms of Formula XV, $R_1$ and $R_2$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XV, $R_1$, and $R_2$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XV, when E', G', $R_1$, and/or $R_2$ are substituted functional groups, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms, the first reactant can have the structure of Formula XVI:

Formula XVI

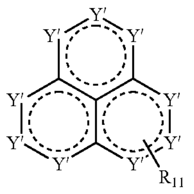

where Y' and $R_{11}$ can be as defined above for Formula XIII and where at least one Y' is O, S, or $NR_2$ and $R_2$ is as defined above for Formula XV.

In some forms, the first reactant can have the structure of Formula XVIIa or Formula XVIIb:

Formula XVIIa

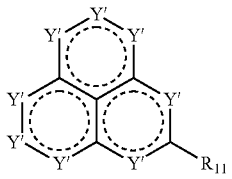

-continued

Formula XVIIb

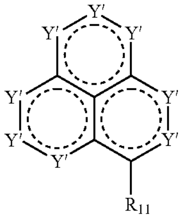

where Y' and $R_{11}$ can be as defined above for Formula XIII and where at least one Y' is O, S, or $NR_2$ and $R_2$ is as defined above for Formula XV.

In some forms, the first reactant can have the structure of Formula XVIIIa or Formula XVIIIb:

Formula XVIIIa

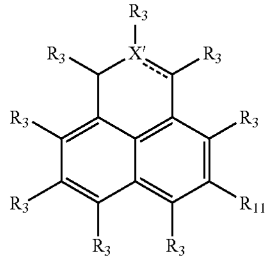

Formula XVIIIb

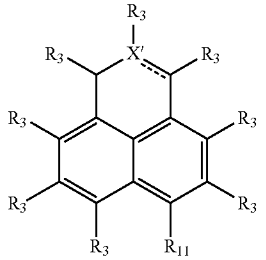

where X' can be C, N, O, or S, where each occurrence of $R_3$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where Rn can be as defined in Formula XIII; and where the substituents can be any of the substituents described above for Formula I.

In some forms of Formula XVIIIa and Formula XVIIIb, X' can be C or N and each occurrence of $R_3$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XVIIIa and Formula XVIIIb, X' can be C or N and each occurrence of $R_3$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XVIIIa and Formula XVIIIb, when $R_3$ is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formulae XVIIIa and XVIIIb, X' can be C or N, each occurrence of $R_3$ can be independently a hydrogen, a substituted or unsubstituted alkyl, a substituted or unsubstituted aryl, an amino, an oxo, a halogen, a hydroxyl, a heterocyclic group

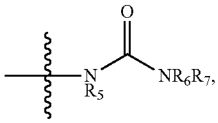,

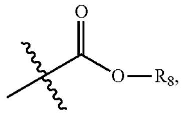, or

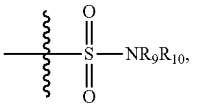, and $R_5$-$R_{10}$ can be independently a hydrogen, a substituted or unsubstituted alkyl, a substituted or unsubstituted aryl, an amino, or a halogen.

In some forms of Formulae XVIIIa and XVIIIb, X' can be C or N, each occurrence of $R_3$ can be independently a hydrogen, a substituted or unsubstituted alkyl, an oxo, a hydroxyl

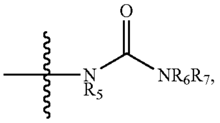, or

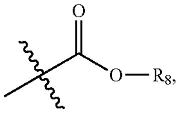, and $R_5$-$R_8$ can be independently a hydrogen or a substituted or unsubstituted alkyl.

In some forms of Formulae XVIIIa and XVIIIb, X' can be C or N, each occurrence of $R_3$ can be independently a hydrogen, a substituted or unsubstituted alkyl, an oxo, a hydroxyl, or a carboxyl.

In some forms, the second reactant can have the structure of Formula XIX:

Formula XIX

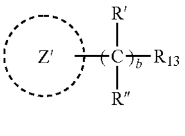

where b can be an integer from 0 to 6, from 0 to 5, from 0 to 4, from 0 to 3, from 0 to 2, or 0 or 1; where R' and R" can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where Z' can be a substituted or unsubstituted polyaryl or a substituted or unsubstituted polyheteroaryl; and where $R_{13}$ can be a leaving group.

In some forms of Formula XIX, b is 0.

In some forms of Formula XIX, $R_{13}$ can be any leaving groups for Rn described above, such as tri-fluoro methane sulfonate ("OTf"), p-toluene sulfonate, methane sulfonate, or a group that has the structure of Formula XIV as defined above.

In some forms, the second reactant can have the structure of Formula XX:

Formula XX

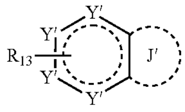

where Y' can be as defined above for Formula XV, $R_{13}$ can be OTf or have the structure of Formula XIV as defined above, and J' can be a substituted or unsubstituted heterocyclyl, a substituted or unsubstituted aryl, a substituted or unsubstituted heteroaryl, a substituted or unsubstituted polyaryl, or a substituted or unsubstituted polyheteroaryl.

In some forms of Formula XX, each occurrence of Y' can be $CR_1$ or $NR_2$, and $R_1$ and $R_2$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XX, each occurrence of Y' can be $CR_1$ or $NR_2$, and $R_1$ and $R_2$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XX, when J', $R_1$, and/or $R_2$ are substituted functional groups, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms, the second reactant can have the structure of Formula XXI:

Formula XXI

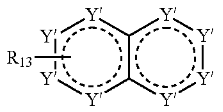

where Y' can be as defined above for Formula XV and Formula XX and $R_{13}$ can be as defined above for Formula XIX.

In some forms, the second reactant can have the structure of Formula XXII:

Formula XXII

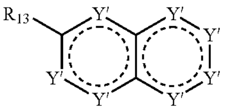

where Y' can be as defined above for Formula XV and Formula XX and $R_{13}$ can be as defined above for Formula XIX.

In some forms, the second reactant can have the structure of Formula XXIII:

Formula XXIII

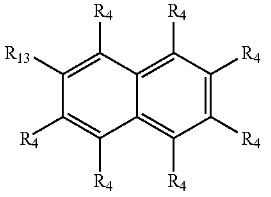

where each occurrence of $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; where $R_{13}$ can be as defined above for Formula XIX; and where the substituents can be any of the substituents described above for Formula I.

In some forms of Formula XXIII, each occurrence of $R_4$ can be independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen.

In some forms of Formula XXIII, each occurrence of $R_4$ can be independently a hydrogen, a substituted or unsubstituted alkyl, a substituted or unsubstituted aryl, a substituted or unsubstituted carbonyl, an amido, an amino, a sulfonyl, an oxo, a hydroxyl, or a halogen.

In some forms of Formula XXIII, when $R_4$ is a substituted functional group, the substituents can be a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo, or a combination thereof.

In some forms of Formula XXIII, each occurrence of $R_4$ can be independently a hydrogen, a substituted or unsubstituted alkyl, a substituted or unsubstituted aryl, an amino, an oxo, a halogen, a hydroxyl, a heterocyclic group,

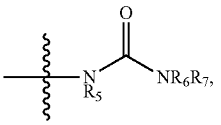 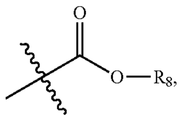 or

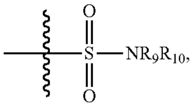

and $R_5$-$R_{10}$ can be independently a hydrogen, a substituted or unsubstituted alkyl, a substituted or unsubstituted aryl, an amino, or a halogen.

In some forms of Formula XXIII, each occurrence of $R_4$ can be independently a hydrogen, a substituted or unsubstituted alkyl, an oxo, a hydroxyl,

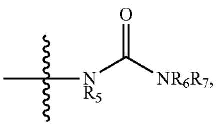 or 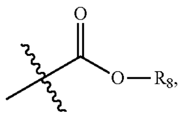

and $R_5$-$R_8$ can be independently a hydrogen or a substituted or unsubstituted alkyl.

In some forms of Formula XXIII, each occurrence of $R_4$ can be independently hydrogen,

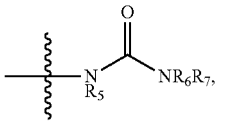 or 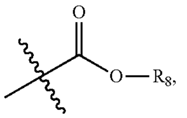

and $R_5$-$R_8$ can be independently a hydrogen or a substituted or unsubstituted alkyl.

In some forms, the reactant mixture can contain a first reactant having the structure of any one of Formulae XIII, XV, XVI, XVIIa, XVIIb, XVIIIa, and XVIIIb, and a second reactant having the structure of any one of Formulae XIX, XX, XXI, XXII, and XXIII.

Suitable solvents for forming the reactant mixture depend on the solubility of the first and second reactants. Typically, the solvent suitable for forming the reactant mixture can dissolve the first and second reactants. Examples of suitable solvents for forming the reactant mixture include, but are not limited to, water, dioxane, dimethoxyethane, 2-methyltetrahydrofuran, cyclopentyl methyl ether, tetrahydrofuran, tert-butyl methyl ether, and dichloromethane, and a mixture thereof. In some forms, the solvent suitable for forming the reactant mixture can be a mixed solvent, such as a mixture of two or more solvents described above, e.g., a mixture of water and dioxane. When the solvent suitable for forming the reactant mixture contains a mixed solvent, each component in the mixed solvent can have a suitable volume ratio. For example, when the solvent suitable for forming the reactant mixture contains a first component, such as water, and a second component, such as dioxane, the volume ratio of water to dioxane can be in a range from 10:1 to 1:10, from 5:1 to 1:5, from 4:1 to 1:4, from 3:1 to 1:3, from 2:1 to 1:2, or about 1:1 or 4:1.

A catalyst is mixed with the reactant mixture to form the reaction mixture. Suitable catalysts that can be used for catalyzing the reaction between the first and second reactants include, but are not limited to, $PdCl_2$(dppf), PdCl2 (dppf)DCM Complex, Tetrakis, $PdCl_2(PPh_3)_2$, XPhos Pd G3, and $Pd(OAc)_2/PPh_3$, and a combination thereof.

The reaction mixture containing the first reactant, the second reactant, optionally a base, and the catalyst in the solvent can be heated at a suitable temperature for a period of time sufficient to form a product containing the compound having the structure of any one of Formulae I-XIIb.

In some forms, the reaction mixture can be heated at a temperature in a range from 50° C. to 150° C., from 60° C. to 150° C., from 70° C. to 150° C., from 80° C. to 150° C., from 50° C. to 140° C., from 50° C. to 120° C., from 70° C. to 120° C., from 80° C. to 120° C., such as about 100° C., for a time period of at least 1 hour, at least 2 hours, at least 3 hours, at least 4 hours, at least 5 hours, at least 6 hours, at least 8 hours, at least 10 hours, up to 20 hours, up to 18 hours, up to 16 hours, in a range from 1 hour to 18 hours, from 2 hours to 16 hours, or from 2 hours to 15 hours, such as about 2 hours, about 15 hours, or about 16 hours.

In some forms, the method can further include a step of mixing the first reactant, the second reactant, and the solvent to form the reactant mixture prior to step (i). In some forms, the first reactant, the second reactant, and the solvent, and optionally a base are mixed at room temperature (i.e., a temperature in the range from about 20° C. to about 22° C. at 1 atm).

In some forms, the method can further include a step of purging the reactant mixture with an inert gas prior to step (ii). Examples of suitable inert gas for purging the reactant mixture are nitrogen, helium, neon, argon, krypton, xenon, and radon.

In some forms, the method can further include a step of stirring the reaction mixture during step (ii). Methods of stirring a reaction mixture during the reaction are known, such as using a magnetic stirring bar or a mechanical mixer.

In some forms, the method can further include a step of purifying the product containing the compound having the structure of any one of Formulae I-XIIb. In some forms, the product containing the compound can be purified by filtration, chromatography, or a combination thereof. In some forms, the product containing the compound can be purified by performing filtration and HPLC sequentially. In some forms, following purification, the purity of the compound in the product is at least 90 wt %, at least 92 wt %, or at least 95 wt %. In some forms, the method does not include any purification, and the purity of the compound in the product is at least 90 wt %, at least 92 wt %, or at least 95 wt %.

In some forms, the method can further include one or more of the above-described steps: mixing the first reactant, the second reactant, and the solvent to form the reactant mixture prior to step (i); purging the reactant mixture with an inert gas prior to step (ii); stirring the reaction mixture during step (ii); and purifying the product containing the compound.

Additional exemplary first and second reactants and more specific methods for synthesizing exemplary compounds are described in the Examples below.

IV. Methods of Use

A. Preventing or Treating or Ameliorating Symptom(s) Associated with Pseudo Allergic Reactions, Pseudo Allergic Diseases, and/or Pseudo Inflammatory Diseases Methods of using the compounds for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject in need thereof are disclosed. The pseudo allergic reaction, pseudo allergic disease, and pseudo inflammatory disease can be local or systemic in the subject.

Pseudo allergic reactions, pseudo allergic diseases, and pseudo inflammatory diseases are non-IgE mediated allergic and inflammatory reactions mediated by the activation of MC's MRGPRX2. The compound can act as MC's MRGPRX2 antagonist. For example, the compounds can target and bind in the binding pocket of MRGPRX2 and thus block the receptor, i.e., MRGPRX2, which prevents the MCs activation and release of inflammatory and pro-inflammatory mediators.

Generally, the method for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject in need thereof includes administering to the subject a pharmaceutical formulation containing one or more of the compounds disclosed herein. The pharmaceutical formulation can be administered in an effective amount to prevent or reduce inflammation, prevent or reduce anaphylaxis symptoms, prevent or reduce tissue damage, and/or prevent or reduce MCs degranulation in the subject. The step of administering an effective amount of the pharmaceutical formulation can be achieved in a single administration step or using multiple steps of administering the pharmaceutical formulation. The subject can be a mammal, such as a human, a dog, a cat, a rat, a monkey, rabbits, guinea pigs, etc., that is in need of treatment.

In some forms of the method, whether inflammation is reduced may be identified by a variety of diagnostic manners known to one skill in the art including, but not limited to, an observed reduction in the size of the tissue where a local allergic reaction occurs, e.g., more than a 5% decrease in size of the inflamed tissue is observed compared to a control tissue without treatment with the compound. A control tissue is a tissue where the same local allergic reaction occurs but treated with a vehicle, such as DMSO or saline, without the compounds.

In some forms of the method, whether anaphylaxis symptoms are reduced may be identified by a variety of diagnostic manners known to one skill in the art including, but not limited to, a lower anaphylaxis score of a subject treated with the compound compared to a control subject without treatment with the compound, where the anaphylaxis score system is as follows: 0, no symptoms; 1, scratching and rubbing around the nose and head; 2, puffiness around the eyes and mouth, diarrhea, pilar erecti, reduced activity, and/or decreased activity with an increased respiratory rate; 3, wheezing, labored respiration, and cyanosis around the mouth and the tail; 4, no activity after prodding or tremor and convulsion; 5, death. A control subject is the subject experiencing the same or similar local or systemic allergic reactions but treated with a vehicle, such as DMSO or saline, saline without the compounds.

In some forms of the method, whether tissue damage is reduced may be identified by a variety of diagnostic manners known to one skill in the art including, but not limited to, a measured reduction in the dye extravasation, such as the Evans blue extravasation, from a tissue where a local allergic reaction occurs compared to a control tissue without treatment with the compound, e.g., more than a 10%, more than a 15%, more than a 20%, more than a 25%, more than a 30%, more than a 35%, more than a 40%, more than a 45%, or more than a 50% of reduction in the dye extravasation, such as Evans blue extravasation, from the tissue where the local allergic reaction occurs is observed compared to a control tissue without treatment with the compound.

In some forms of the method, whether MCs degranulation is reduced may be identified by a variety of diagnostic manners known to one skill in the art including, but not limited to, a measured reduction in the percentage of degranulated MCs in a tissue where a local allergic reaction occurs compared to a control tissue without treatment with the compound, e.g., more than a 10%, more than a 15%, more than a 20%, more than a 25%, more than a 30%, more than a 35%, more than a 40%, more than a 45%, or more than a 50% of reduction in the percentage of degranulated MCs in the tissue where a local allergic reaction occurs is observed compared to a control tissue without treatment with the compound.

1. Pseudo Allergic Reactions, Pseudo Allergic Diseases, and/or Pseudo Inflammatory Diseases The pseudo allergic reactions, pseudo allergic diseases, and pseudo inflammatory diseases being treated by the disclosed method can be any allergic reactions, allergic diseases, or inflammatory diseases that are mediated by MCs activation.

Examples of suitable pseudo allergic reactions, pseudo allergic diseases, and pseudo inflammatory diseases and symptoms associated with the pseudo allergic reactions, pseudo allergic diseases, and pseudo inflammatory diseases that can be treated by the disclosed method include, but are not limited to, anaphylaxis, pruritus ani, cough, migraine, pain, and pain of aphthous ulcers, mastocytosis, mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, SUllliller seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma, and a combination thereof.

2. Administration Routes

The pharmaceutical formulation containing one or more of the disclosed compounds and/or their pharmaceutically acceptable salts can be administered to the subject by oral administration, parenteral administration, inhalation, mucosal, topical administration, or a combination thereof.

For example, the pharmaceutical formulation containing one or more of the disclosed compounds and/or their pharmaceutically acceptable salts can be orally administered to a subject by a medical professional or the subject being treated (e.g., self-administration). The pharmaceutical formulation containing one or more of the disclosed compounds and/or their pharmaceutically acceptable salts can be administered as tablets, capsules containing particulates, granules, powders, lozenges (including liquid-filled lozenges), chews, multi- and nano-particulates, gels, or liquids (e.g., solution or suspensions in aqueous or non-aqueous solvent).

Optionally, the pharmaceutical formulation containing one or more of the disclosed compounds and/or their pharmaceutically acceptable salts can be administered to the subject by intravenous injection or intraperitoneal injection. The intravenous injection or intraperitoneal injection can be performed by a medical professional or the subject being treated (e.g., self-injection).

Alternatively, the pharmaceutical formulation containing one or more of the disclosed compounds and/or their pharmaceutically acceptable salts can be administered to the subject by inhalation, such as mouth inhalation and/or nasal inhalation.

Optionally, the pharmaceutical formulation containing one or more of the disclosed compounds and/or their pharmaceutically acceptable salts can be administered to the subject by topically applying the compound(s) or the pharmaceutical composition or formulation on one or more of the exposed surfaces of the subject.

3. Effective Amount

The step of administering an effective amount of the pharmaceutical formulation can be achieved in a single administration step or using multiple steps of administering the pharmaceutical formulation. For example, if the unit dosage form contains an effective amount of the compounds to prevent or reduce inflammation, prevent or reduce anaphylaxis symptoms, prevent or reduce tissue damage, and/or prevent or reduce MCs degranulation in the subject, then the method only requires a single administration step. Alternatively, if the unit dosage form contains less than the needed effective amount of the compounds to prevent or reduce inflammation, prevent or reduce anaphylaxis symptoms, prevent or reduce tissue damage, and/or prevent or reduce MCs degranulation in the subject, then the method involves at least two steps of administering the pharmaceutical formulation, and optionally more than two steps of administering the pharmaceutical formulation to the subject until an effective amount of the pharmaceutical formulation is administered to the subject to prevent or reduce inflammation, prevent or reduce anaphylaxis symptoms, prevent or reduce tissue damage, and/or prevent or reduce MCs degranulation in the subject. When multiple administration steps are needed to administer an effective amount of the pharmaceutical formulation to the subject, each administration step may involve administering the same dosage or different dosages of the pharmaceutical formulation to the patient. In some forms, the method involves a single administration of the pharmaceutical formulation in an effective amount to prevent or reduce inflammation, prevent or reduce anaphylaxis symptoms, prevent or reduce tissue damage, and/or prevent or reduce MCs degranulation in the subject.

In some forms of the method, the pharmaceutical formulation administered to the subject is in an effective amount to reduce the size of a tissue where local allergic reaction occurs, compared to a control tissue without treatment with the compound. In some forms of the method, the pharmaceutical formulation is administered to the subject is in an effective amount to lower the anaphylaxis score of the subject compared to a control without treatment with the compound. In some forms of the method, the pharmaceutical formulation is administered to the subject is in an effective amount to reduce the dye extravasation, such as the Evans blue dye extravasation, of a tissue where local allergic reaction occurs, compared to a control tissue without treatment with the compound, which is indicative of reduced vascular leakage in the tissue. In some forms of the method, the pharmaceutical formulation is administered to the subject is in an effective amount to reduce the percentage of degranulated MCs in a tissue where a local allergic reaction occurs compared to a control without treatment with the compound.

In some forms of the method, the pharmaceutical formulation administered to the subject is in an effective amount to reduce the size, the dye extravasation, and/or the percentage of degranulated MCs of a tissue where local allergic reaction occurs compared to a control tissue without treatment with the compounds, and/or lower the anaphylaxis score of the subject compared to a control without treatment with the compounds.

In some forms of the method, the pharmaceutical formulation administered to the subject is in an effective amount to reduce the size of a tissue where the local allergic reaction occurs by at least 5%, at least 10%, at least 15%, or at least 20%, compared to a control tissue without treatment with the compound.

In some forms of the method, the pharmaceutical formulation administered to the subject is in an effective amount to lower the anaphylaxis score of the subject by at least 1, at least 2, at least 3, at least 4, or 5, where the anaphylaxis score system is as follows: 0, no symptoms; 1, scratching and rubbing around the nose and head; 2, puffiness around the eyes and mouth, diarrhea, pilar erecti, reduced activity, and/or decreased activity with an increased respiratory rate; 3, wheezing, labored respiration, and cyanosis around the mouth and the tail; 4, no activity after prodding or tremor and convulsion; 5, death.

In some forms of the method, the pharmaceutical formulation administered to the subject is in an effective amount to reduce the dye extravasation, such as the Evans blue dye extravasation, from a tissue where local allergic reaction occurs by more than 10%, more than 15%, more than 20%, more than 25%, more than 30%, more than 35%, more than 40%, more than 45%, or more than 50%, compared to a control tissue without treatment with the compounds.

In some forms of the method, the pharmaceutical formulation administered to the subject is in an effective amount to reduce the percentage of degranulated MCs in a tissue where a local allergic reaction occurs by more than 10%, more than 15%, more than 20%, more than 25%, more than 30%, more than 35%, more than 40%, more than 45%, or more than 50%, compared to a control without treatment with the compound.

In some forms, treatment regimens utilizing compounds include administration of from about 0.1 mg to about 300 mg of the compounds per kilogram body weight of the recipient per day in multiple doses or in a single dose. In some embodiments, a suitable dose may be in the range of 0.1 to 300 mg per kilogram body weight of the recipient per day, optionally in the range of 6 to 150 mg per kilogram body weight per day, optionally in the range of 15 to 100 mg per kilogram body weight per day, optionally in the range of 15 to 80 mg per kilogram body weight per day, optionally in the range of 15 to 50 mg per kilogram body weight per day, and optionally in the range of 15 to 30 mg per kilogram body weight per day.

The desired dose may be presented as two, three, four, five or six or more sub-doses administered at appropriate intervals throughout the day. These sub-doses may be administered in unit dosage forms, for example, containing from 0.01 mg to 1500 mg, from 0.1 mg to 1500 mg, from 1 mg to 1500 mg, from 10 mg to 1500 mg, from 20 mg to 1500 mg, from 0.01 mg to 1000 mg, from 0.1 mg to 1000 mg, from 1 mg to 1000 mg, from 10 mg to 1000 mg, from 20 mg to 1000 mg, from 0.01 mg to 700 mg, from 0.1 mg to 700 mg, from 1 mg to 700 mg, from 10 mg to 700 mg, from 20 mg to 700 mg, from 50 mg to 700 mg, from 0.01 mg to 500 mg, from 0.1 mg to 500 mg, from 1 mg to 500 mg, from 10 mg to 500 mg, from 20 mg to 500 mg, from 50 mg to 500 mg, from 0.01 mg to 100 mg, or from 0.1 mg to 100 mg of the compounds per unit dosage form.

4. Optional Steps a. Administering Additional Active Agent(s)

One or more active agents in addition to the compounds may be administered to the subject throughout the method or at different intervals during the method. For example, the one or more additional active agents is administered to the subject prior to, during, and/or subsequent to step (i) administering the pharmaceutical formulation containing the compounds. In some forms, the one or more additional active agents can be included in the pharmaceutical formulation containing the compound(s) and administered to the subject simultaneously with the compound(s).

In some forms, the one or more additional active agents are one or more antiallergic and/or anti-inflammatory agents as described above. The amount of the one or more additional antiallergic and/or anti-inflammatory agents administered will vary from subject to the subject according to their need.

B. Treating Mast Cells

In some forms, the compounds can be used in a method for treating mast cells ("MCs") in a subject in need thereof.

The method can follow the method step described above, for example, administering to the subject an effective amount of a pharmaceutical formulation containing one or more of the compounds by oral administration, parenteral administration, inhalation, mucosal, topical administration, or a combination thereof. In some forms, the method can include the additional step described above. For example, the user can administer one or more additional active agents to the subject prior to, during, and/or subsequent to administering the pharmaceutical formulation to the subject.

In some forms of the method, the compounds can inhibit MCs degranulation and/or MRGPRX2 activation in the subject, compared with cells in a control not treated with the compounds, tested under the same conditions. Additionally or alternatively, the compounds can reduce the calcium cation ("$Ca^{2+}$") flux in the MCs of the subject, compared with MCs in a control not treated with the compounds, tested under the same conditions. Additionally or alternatively, the compounds can reduce the release of inflammatory chemokine and/or cytokine, compared with MCs in a control not treated with the compounds, tested under the same conditions.

In some forms of the method, the compound can inhibit MCs degranulation with an $IC_{50}$ value that is lower than an $IC_{50}$ value of a positive control compound, such as genistein, tested under the same condition. Alternatively or additionally, the compound can inhibit MRGPRX2 activation with an $IC_{50}$ value that is lower than an $IC_{50}$ value of a positive control compound, such as genistein, tested under the same condition.

1. Inhibition of MCs Degranulation and/or MRGPRX2 Activation

In some forms of the method, the pharmaceutical formulation administered to the subject is in an effective amount to inhibit MCs degranulation in the subject, compared with MCs in a control not treated with the compounds, tested under the same conditions. "Same conditions" for testing the inhibition of MCs degranulation means test is performed using the same assay, such as a MCs degranulation assay, using the same protocol, such as same amount of cells and enzymes, same buffer and buffer concentration, same dye and dye concentration, and same incubation time and temperature, etc.

MCs degranulation is an event in releasing preformed/de novo synthesized mediators and developing the edema and lesions in allergy. MCs granules store a potent cocktail of preformed inflammatory mediators, such as histamine, heparin, serotonin, tryptase, and chymase. Several de-novo synthesized mediators such as prostaglandins derived from the precursor molecule arachidonic acid. Thus, the level of MCs degranulation can be assessed using the MCs degranulation assay by measuring the percentage of an inflammatory mediator release, such as the percentage of β-Hexosaminidase release.

In some forms of the method, the pharmaceutical formulation administered to the subject is in an effective amount to inhibit MCs degranulation in the subject by at least 30%, at least 35%, at least 40%, at least 45%, at least 50%, at least 55%, at least 60%, at least 65%, at least 70%, at least 75%, in a range from 30% to 90%, from 30% to 80%, from 30% to 75%, from 35% to 75%, from 35% to 75%, from 40% to 90%, from 40% to 80%, or from 40% to 75%, compared with MCs in a control not treated with the compounds, tested under the same conditions.

In some forms of the method, the pharmaceutical formulation administered to the subject is in an effective amount to inhibit MRGPRX2 activation in the subject, compared with cells in a control not treated with the compounds, tested under the same conditions. "Same conditions" for testing the inhibition of MRGPRX2 activation means test is performed using the same assay, such as MRGPRX2 activation assay, using the same protocol, such as the same amount of cells and enzymes, same buffer and buffer concentration, same dye and dye concentration, and same incubation time and temperature, etc. In some forms, the cells used in the MRGPRX2 activation assay are MRGPRX2-Tango transfected HTLA cells.

In some forms of the method, the pharmaceutical formulation administered to the subject is in an effective amount to inhibit MRGPRX2 activation in the subject by at least 30%, at least 35%, at least 40%, at least 45%, at least 50%, at least 55%, at least 60%, at least 65%, at least 70%, at least 75%, in a range from 30% to 99%, from 30% to 95%, from 30% to 90%, from 30% to 85%, from 30% to 80%, from 30% to 75%, from 30% to 70%, from 40% to 99%, from 40% to 95%, from 40% to 90%, from 40% to 85%, from 40% to 80%, from 40% to 75%, from 40% to 70%, from 45% to 99%, from 45% to 95%, from 45% to 90%, from 45% to 85%, from 45% to 80%, from 45% to 75%, or from 45% to 70%, compared with cells in a control not treated with the compounds, tested under the same conditions.

In some forms of the method, the pharmaceutical formulation administered to the subject is in an effective amount to inhibit MCs degranulation and MRGPRX2 activation in the subject, compared with cells in a control not treated with the compounds, tested under the same conditions. In some forms of the method, the compounds can inhibit MCs degranulation in the subject by at least 30%, at least 35%, at least 40%, at least 45%, at least 50%, at least 55%, at least 60%, at least 65%, at least 70%, at least 75%, in a range from 30% to 90%, from 30% to 80%, from 30% to 75%, from 35% to 75%, from 35% to 75%, from 40% to 90%, from 40% to 80%, or from 40% to 75%, compared with MCs in a control not treated with the compounds, tested under the same conditions, and inhibit MRGPRX2 activation in the subject by at least 30%, at least 35%, at least 40%, at least 45%, at least 50%, at least 55%, at least 60%, at least 65%, at least 70%, at least 75%, in a range from 30% to 99%, from 30% to 95%, from 30% to 90%, from 30% to 85%, from 30% to 80%, from 30% to 75%, from 30% to 70%, from 40% to 99%, from 40% to 95%, from 40% to 90%, from 40% to 85%, from 40% to 80%, from 40% to 75%, from 40% to 70%, from 45% to 99%, from 45% to 95%, from 45% to 90%, from 45% to 85%, from 45% to 80%, from 45% to 75%, or from 45% to 70%, compared with cells (such as MRGPRX2-Tango transfected HTLA cells) in a control not treated with the compounds, tested under the same conditions.

In some forms of the method, the pharmaceutical formulation administered to the subject is in an effective amount to inhibit MCs degranulation in the subject with an $IC_{50}$ value of less than 30 μM, less than 25 μM, less than 20 μM, less than 15 μM, less than 10 μM, less than 5 μM, in a range from 1 μM to 30 μM, from 1 μM to 25 μM, from 1 μM to 20 μM, from 1 μM to 15 μM, from 1 μM to 10 μM, from 1 μM to 5 μM, from 4 μM to 30 μM, from 4 μM to 25 μM, from 4 μM to 20 μM, from 4 μM to 15 μM, or from 4 μM to 10 μM, tested in a MCs degranulation assay.

In some forms of the method, the pharmaceutical formulation administered to the subject is in an effective amount to inhibit MRGPRX2 activation in the subject with an $IC_{50}$ value of less than 25 μM, less than 20 μM, less than 15 μM, less than 10 μM, in a range from 1 μM to 25 μM, from 1 μM to 20 μM, from 1 μM to 15 μM, from 1 μM to 10 μM, from 5 μM to 25 μM, from 5 μM to 20 μM, from 5 μM to 15 μM, or from 5 μM to 10 μM, tested in a MRGPRX2 activation assay.

In some forms of the method, the pharmaceutical formulation administered to the subject is in an effective amount to inhibit MCs degranulation with an $IC_{50}$ value that is lower than an $IC_{50}$ value of a positive control compound, such as genistein, tested under the same condition.

In some forms of the method, the pharmaceutical formulation administered to the subject is in an effective amount to inhibit MCs degranulation with an $IC_{50}$ value that is at least 10% lower, at least 15% lower, at least 20% lower, at least 25% lower, at least 30% lower, at least 40% lower, at least 50% lower, at least 1-fold lower, at least 2-fold lower, at least 3-fold lower, at least 4-fold lower, or at least 5-fold lower than an $IC_{50}$ value of a positive control compound, such as genistein, tested under the same condition.

In some forms of the method, the pharmaceutical formulation administered to the subject is in an effective amount to inhibit MRGPRX2 activation with an $IC_{50}$ value that is lower than an $IC_{50}$ value of a positive control compound, such as genistein, tested under the same condition.

In some forms of the method, the pharmaceutical formulation administered to the subject is in an effective amount to inhibit MRGPRX2 activation with an $IC_{50}$ value that is at least 10% lower, at least 15% lower, at least 20% lower, at least 25% lower, at least 30% lower, at least 40% lower, at least 50% lower, at least 1-fold lower, at least 2-fold lower, at least 3-fold lower, at least 4-fold lower, or at least 5-fold lower than an $IC_{50}$ value of a positive control compound, such as genistein, tested under the same condition.

Exemplary $IC_{50}$ values of exemplary compounds and exemplary known compounds for MCs inhibition and MRGPRX2 activation, tested under specific conditions, are described in the Examples below.

2. Reduction of $Ca^{2+}$ Flux

MRGPRX2 activation can lead to a rapid increase in intracellular $Ca^{2+}$ flux that decays very slowly, and MCs degranulation is preceded by surges of intracellular $Ca^{2+}$ concentrations. This sustained $Ca^{2+}$ flux response induced by MRGPRX2 is unique compared to other GPCRs, which mostly induce a transient $Ca^{2+}$ response that almost immediately returns to baseline due to their rapid desensitization and internalization.

In some forms of the method, the compounds can reduce the calcium cation ("$Ca^{2+}$") flux in the MCs of the subject, compared with MCs in a control not treated with the compounds, tested under the same conditions. "Same conditions" for testing the $Ca^{2+}$ flux in MCs means test is performed using the same assay, such as MCs degranulation assay, using the same protocol, such as the same amount of cells and enzymes, same buffer and buffer concentration, same dye and dye concentration, and same incubation time and temperature, etc.

In some forms of the method, the pharmaceutical formulation administered to the subject is in an effective amount to reduce the $Ca^{2+}$ flux in MCs of the subject by at least 20%, at least 30%, at least 40%, at least 45%, at least 50%, at least 55%, at least 60%, at least 65%, at least 70%, at least 75%, at least 80%, at least 85%, at least 90%, in a range from 20% to 95%, from 20% to 90%, from 20% to 85%, from 30% to 80%, from 30% to 95%, from 30% to 90%, from 30% to 85%, from 30% to 80%, from 40% to 95%, from 40% to 90%, from 40% to 85%, or from 40% to 80%, compared with MCs in a control not treated with the compounds, tested under the same conditions.

3. Reduction of Inflammatory Chemokine and/or Cytokine Release

MCs activation includes an early phase that includes $Ca^{2+}$ flux and degranulation and a delayed phase that induces production and release of inflammatory chemokine and/or cytokine, such as monocyte chemoattractant protein-1 ("MCP-1") and Prostaglandin D-2 ("PGD-2").

In some forms of the method, the compounds can reduce the amount of an inflammatory chemokine and/or cytokine, such as MCP-1 and/or PGD-2, released from MCs of the subject, compared with MCs in a control not treated with the compounds, tested under the same conditions. "Same conditions" for testing the amount of inflammatory chemokine and/or cytokine released from MCs means test is performed using the same assay, such as MCs degranulation assay, using the same protocol, such as same amount of cells and enzymes, same buffer and buffer concentration, same dye and dye concentration, and same incubation time and temperature, etc.

In some forms of the method, the pharmaceutical formulation administered to the subject is in an effective amount to reduce the amount of an inflammatory chemokine and/or cytokine, such as MCP-1, released from MCs of the subject by at least 5%, at least 10%, at least 15%, at least 20%, at least 25%, at least 30%, at least 35%, at least 40%, at least 45%, at least 50%, in a range from 5% to 50%, from 10% to 50%, from 5% to 45%, from 10% to 45%, from 5% to 40%, or from 10% to 40%, compared with MCs in a control not treated with the compounds, tested under the same conditions.

In some forms of the method, the pharmaceutical formulation administered to the subject is in an effective amount to reduce the amount of an inflammatory chemokine and/or cytokine, such as PGD-2, released from MCs of the subject by at least 30%, at least 35%, at least 40%, at least 45%, at least 50%, at least 55%, at least 60%, in a range from 30% to 80%, from 30% to 75%, from 30% to 70%, from 30% to 65%, from 30% to 60%, or from 30% to 55%, compared with MCs in a control not treated with the compounds, tested under the same conditions.

In some forms of the method, the pharmaceutical formulation administered to the subject is in an effective amount to reduce the amount of MCP-1 released from MCs of the subject by at least 5%, at least 10%, at least 15%, at least 20%, at least 25%, at least 30%, at least 35%, at least 40%, at least 45%, at least 50%, in a range from 5% to 50%, from 10% to 50%, from 5% to 45%, from 10% to 45%, from 5% to 40%, or from 10% to 40%, and to reduce the amount of PGD-2 released from MCs of the subject by at least 30%, at least 35%, at least 40%, at least 45%, at least 50%, at least 55%, at least 60%, in a range from 30% to 80%, from 30% to 75%, from 30% to 70%, from 30% to 65%, from 30% to 60%, or from 30% to 55%, compared with MCs in a control not treated with the compounds, tested under the same conditions.

The disclosed compounds, methods of using, and methods of making can be further understood through the following enumerated paragraphs.

1. A compound having the structure of

Formula I

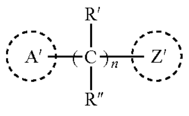

(a) wherein n is an integer from 0 to 6, from 0 to 5, from 0 to 4, from 0 to 3, from 0 to 2, or 0 or 1;

(b) wherein $R_1$ and $R_2$ are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;

(c) wherein A' and Z' are independently a substituted or unsubstituted polyaryl or a substituted or unsubstituted polyheteroaryl; and (d) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

2. The compound of paragraph 1, wherein the compound has the structure of

Formula Ia

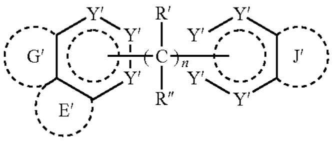

(a) wherein E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(b) wherein J' is a substituted or unsubstituted heterocyclyl, a substituted or unsubstituted aryl, a substituted or unsubstituted heteroaryl, a substituted or unsubstituted polyaryl, or a substituted or unsubstituted polyheteroaryl;

(c) wherein each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (d) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

3. The compound of paragraph 1 or 2, wherein n is 0.

4. The compound of paragraphs 1 or 3, wherein A' has the structure of

Formula II

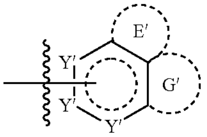

(a) wherein E' and G' are independently a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; and (b) wherein each occurrence of Y' is independently $CR_1$, O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (c) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

5. The compound of any one of paragraphs 1-4, wherein A' has the structure of

Formula IVa

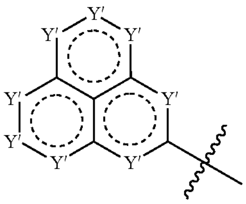

-continued

Formula IVb

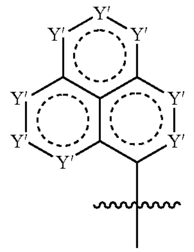

(a) wherein each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

6. The compound of any one of paragraphs 1-5, wherein A' has the structure of

Formula Va

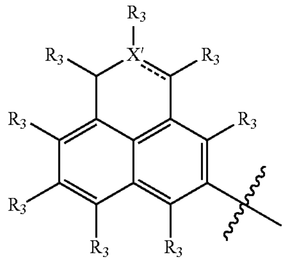

-continued

Formula Vb

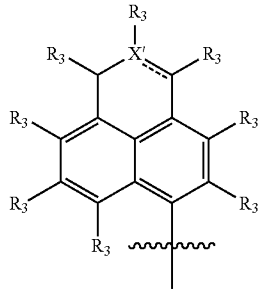

(a) wherein X' is C, N, O, or S;

(b) wherein each occurrence of $R_3$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (c) the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

7. The compound of paragraph 6, (a) wherein X' is C or N;

(b) wherein each occurrence of $R_3$ is independently a hydrogen, a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a thiol, a sulfonyl, a hydroxyl, or a halogen; and (c) wherein the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

8. The compound of paragraph 6 or 7, (a) wherein X' is C or N;

(b) wherein each occurrence of $R_3$ is independently a hydrogen, a substituted or unsubstituted alkyl, a substituted or unsubstituted aryl, an amino, an oxo, a halogen, a hydroxyl, a heterocyclic group

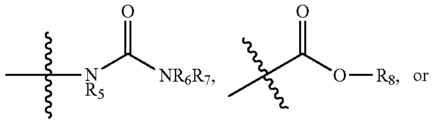

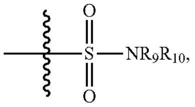

and $R_5$-$R_{10}$ are independently a hydrogen, a substituted or unsubstituted alkyl, a substituted or unsubstituted aryl, an amino, or a halogen; and (c) wherein the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

9. The compound of any one of paragraphs 6-8, (a) wherein X' is C or N;

(b) wherein each occurrence of $R_3$ is independently a hydrogen, a substituted or unsubstituted alkyl, an oxo, a hydroxyl, or a carboxyl; and (c) wherein the substituent are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

10. The compound of any one of paragraphs 1 or 3-9, wherein Z' has the structure of Formula VI

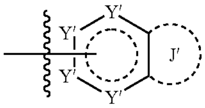

(a) wherein each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;

(b) wherein J' is a substituted or unsubstituted heterocyclyl, a substituted or unsubstituted aryl, a substituted or unsubstituted heteroaryl, a substituted or unsubstituted polyaryl, or a substituted or unsubstituted polyheteroaryl; and (c) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

11. The compound of any one of paragraphs 1-10, wherein Z' has the structure of

Formula VIII

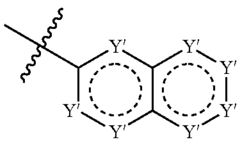

(a) wherein each occurrence of Y' is independently $CR_1$, O, S, or $NR_2$, and at least one Y' is O, S, or $NR_2$, wherein $R_1$ and $R_2$ is independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

12. The compounds of any one of paragraphs 1-11, wherein Z' has the structure of Formula IX

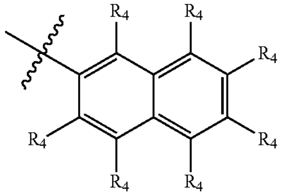

(a) wherein each occurrence of $R_4$ can be independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen; and (b) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

13. The compound of paragraph 12, (a) wherein each occurrence of $R_4$ is independently a hydrogen, a substituted or unsubstituted alkyl, a substituted or unsubstituted aryl, an amino, an oxo, a halogen, a hydroxyl, a heterocyclic group,

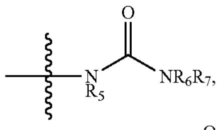,
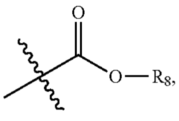, or

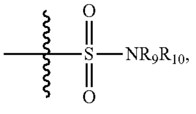, and $R_5$-$R_{10}$ are independently a hydrogen, a substituted or unsubstituted alkyl, a substituted or unsubstituted aryl, an amino, or a halogen; and (b) wherein the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

14. The compound of paragraph 12 or 13, (a) wherein each occurrence of $R_4$ is independently a hydrogen,

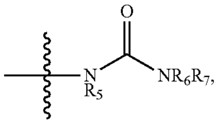, or 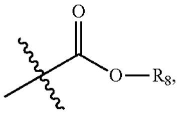, and $R_5$-$R_8$ are independently a hydrogen or a substituted or unsubstituted alkyl; and (b) wherein the substituents are independently a substituted or unsubstituted alkyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, an amino, an amido, or an oxo.

15. The compound of any one of paragraphs 1-14 having the structure of

GE0117

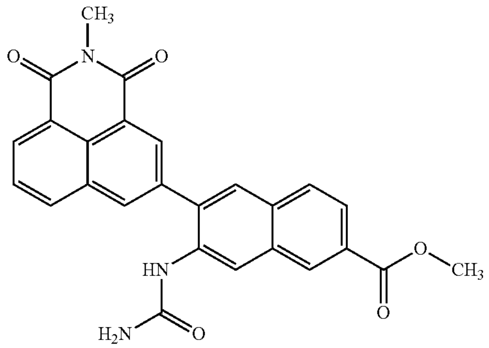

GE0118

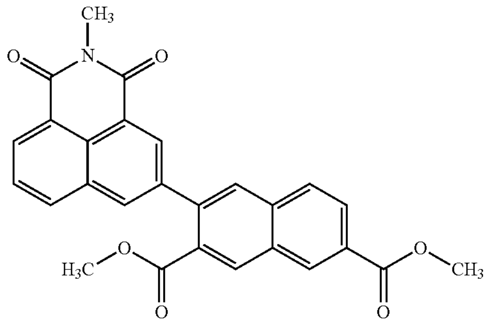

-continued

GE0119

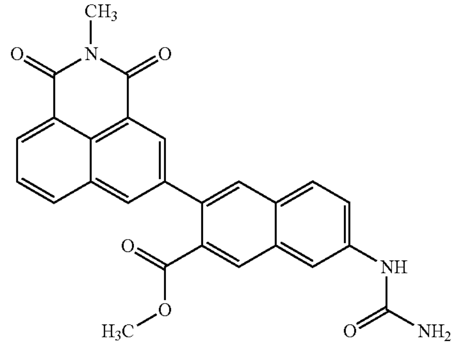

GE1109

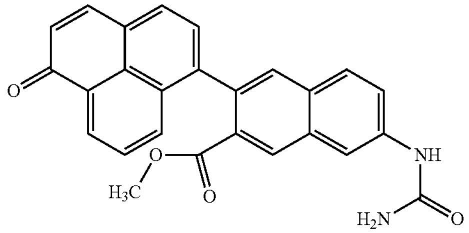

GE1110

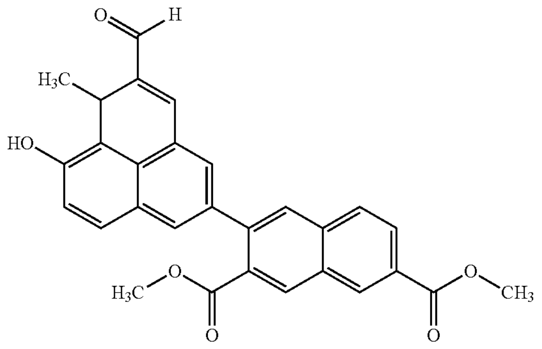

GE1111

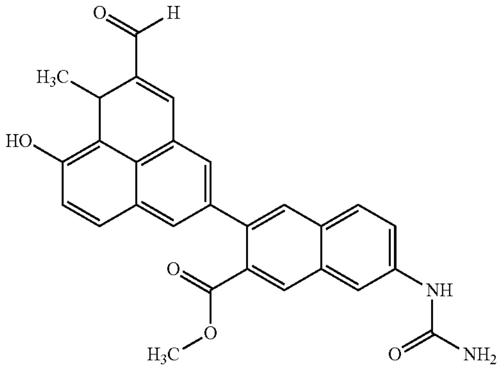

16. A pharmaceutical formulation comprising
one or more compounds of any one of paragraphs 1-15; and
a pharmaceutically acceptable excipient,
wherein the one or more compounds are in an effective amount to prevent or treat a pseudo allergic reaction, a pseudo allergic disease, or a pseudo inflammatory disease, or treat or ameliorate one or more symptoms associated with a pseudo allergic reaction, a pseudo allergic disease, or a pseudo inflammatory disease in a subject.

17. The pharmaceutical formulation of paragraph 16 further comprising a second active agent, optionally more than one second active agent.

18. The pharmaceutical formulation of paragraph 16 or 17, wherein the second active agent is an antiallergic agent or an anti-inflammatory agent, or a combination thereof.

19. A method for making the compound of any one of paragraphs 1-15 comprising
(i) mixing a reactant mixture and a catalyst to form a reaction mixture, wherein the reactant mixture comprises a first reactant, a second reactant, and a solvent; and
(ii) heating the reaction mixture at a suitable temperature for a period of time sufficient to form a product containing the compound of paragraph 1,
wherein step (i) is performed prior to or simultaneously with step (ii).

20. The method of paragraph 19, wherein the first reactant has the structure of

Formula XIII

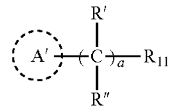

(a) wherein a is an integer from 0 to 6, from 0 to 5, from 0 to 4, from 0 to 3, from 0 to 2, or 0 or 1;
(b) wherein R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;
(c) wherein A' is a substituted or unsubstituted polyaryl or a substituted or unsubstituted polyheteroaryl;
(d) wherein $R_{11}$ is a halogen or has the structure of Formula XIV

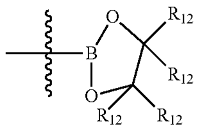

wherein each occurrence of $R_{12}$ is independently a hydrogen or a substituted or unsubstituted alkyl; and
(e) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

21. The method of paragraph 19 or 20, wherein the second reactant has the structure of Formula XIX

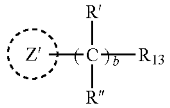

(a) wherein b is an integer from 0 to 6, from 0 to 5, from 0 to 4, from 0 to 3, from 0 to 2, or 0 or 1;

(b) wherein R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;

(c) wherein Z' is a substituted or unsubstituted polyaryl or a substituted or unsubstituted polyheteroaryl;

(d) wherein $R_{13}$ is trifluoromethanesulfonate ("OTf") or has the structure of Formula XIV; and (e) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

22. The method of any one of paragraphs 19-21, wherein the solvent is water, dioxane, dimethoxyethane, 2-methyltetrahydrofuran, cyclopentyl methyl ether, tetrahydrofuran, tert-butyl methyl ether, or dichloromethane, or a combination thereof.

23. The method of any one of paragraphs 19-22, wherein the catalyst is $PdCl_2$(dppf), $PdCl_2$(dppf)DCM Complex, Tetrakis, $PdCl_2(PPh_3)_2$, XPhos Pd G3, or $Pd(OAc)_2/PPh_3$, or a combination thereof.

24. The method of any one of paragraphs 19-24, wherein in step (ii), the reaction mixture is heated at a temperature in a range from 50° C. to 150° C., from 60° C. to 150° C., from 70° C. to 150° C., from 80° C. to 150° C., from 50° C. to 140° C., from 50° C. to 120° C., from 70° C. to 120° C., from 80° C. to 120° C., such as about 100° C., for a time period of at least 1 hour, at least 2 hours, at least 3 hours, at least 4 hours, at least 5 hours, at least 6 hours, at least 8 hours, at least 10 hours, up to 20 hours, up to 18 hours, up to 16 hours, in a range from 1 hour to 18 hours, from 2 hours to 16 hours, or from 2 hours to 15 hours.

25. The method of any one of paragraphs 19-24 further comprising mixing the first reactant, the second reactant, and the solvent to form the reactant mixture prior to step (i), purging the reactant mixture with an inert gas prior to step (ii), stirring the reaction mixture during step (ii), and/or purifying the product containing the compound.

26. A method for preventing or treating pseudo allergic reactions, pseudo allergic diseases, and/or pseudo inflammatory diseases, or treating or ameliorating one or more symptoms associated with a pseudo allergic reaction, a pseudo allergic disease, and/or a pseudo inflammatory disease in a subject in need thereof comprising (i) administering to the subject the pharmaceutical formulation of any one of paragraphs 16-18, wherein step (i) occurs one or more times.

27. The method of paragraph 26 comprising only a single administration of the pharmaceutical formulation, wherein the pharmaceutical formulation comprises an effective amount of the compounds to prevent or reduce inflammation, prevent or reduce anaphylaxis symptoms, prevent or reduce tissue damage, and/or prevent or reduce MCs degranulation in the subject.

28. The method of paragraph 26 or 27 comprising more than one step of administering to the subject the pharmaceutical formulation, wherein following all of the administration steps, an effective amount of the compounds to prevent or reduce inflammation, prevent or reduce anaphylaxis symptoms, prevent or reduce tissue damage, and/or prevent or reduce MCs degranulation in the subject is administered to the subject.

29. The method of any one of paragraphs 26-28, wherein the subject is a mammal.

30. The method of any one of paragraphs 26-29, wherein the pharmaceutical formulation is administered by oral administration, parenteral administration, inhalation, mucosal administration, topical or a combination thereof.

31. The method of any one of paragraphs 26-30 further comprising administering to the subject a second active agent, optionally more than one second active agent, prior to, during, and/or subsequent to step (i).

32. The method of paragraph 31, wherein the second active agent is an antiallergic agent or an anti-inflammatory agent, or a combination thereof.

33. A method for treating mast cells ("MCs") in a subject in need thereof comprising (i) administering to the subject the pharmaceutical formulation of any one of paragraphs 16-18, wherein step (i) occurs one or more times.

34. The method of paragraph 33 comprising only a single administration of the pharmaceutical formulation, wherein the pharmaceutical formulation comprises an effective amount of the compounds to inhibit MCs degranulation, inhibit MRGPRX2 activation, reduce calcium cation ("$Ca^{2+}$") flux in the MCs, and/or reduce the release of inflammatory chemokine and/or cytokine, compared with cells in a control not treated with the compounds, tested under the same conditions.

35. The method of paragraph 33 or 34 comprising more than one step of administering to the subject the pharmaceutical formulation, wherein following all of the administration steps, an effective amount of the compounds to inhibit MCs degranulation, inhibit MRGPRX2 activation, reduce $Ca^{2+}$ flux in the MCs, and/or reduce release of inflammatory chemokine and/or cytokine, compared with cells in a control not treated with the compounds, tested under the same conditions.

The present invention will be further understood by reference to the following non-limiting examples.

EXAMPLES

Example 1. Synthesis of Exemplary Compounds

Materials and Methods

Homology and Pharmacophore Identification of MRGPRX2

A 3D homology model of MRGPRX2 was developed by using a template of the kappa-opioid receptor (PDB ID: 6B73) according to the previous class B hSCTR model development method. Three different homology models were developed using both SWISS-MODEL algorithms and MODELLER algorithms. The models were further evaluated and screened for steric collisions between atoms by Ramachandran's help in the Rampage server. The homology model was validated by Auto dock vina virtual docking of small compound agonists ZINC72453573 and C48-80 at known binding sites on the receptor. To identify the pharmacophore region, genistein was docked with the MRGPRX2 receptor via Auto Dock vina and visualized by PyMOL, Discovery studio visualizer and Schrodinger maestro suite. The amino acid residues were defined and further used to develop the pharmacophore model via Pharmit. The active site pre-defined from the MRGPRX2-genistein model was analyzed to locate the interactive amino acid residues. This complex was used as the principal structure for the designing and screening of small compound antagonists.

In-Silico Designing and Screening of Potential Small Compound Antagonists

Based on the amino acid interaction map and genistein's pharmacophore, several compounds with different H-bond donors and functional groups (Ar—$NH_2$, alkyl-OH, Ar—OH, alkyl-COOH, alkyl-NH—CO—NH-alkyl, alkyl-$S(O)_2$—NH-alkyl, alkyl-NH—CO—NH—Ar, halogens, and heterocyclic amine) were designed. The compounds' chemical structure was drawn using ACD/ChemSketch software (Advanced Chemistry Development 2020), saved as a MOL file, and optimized before docking study using an advanced molecule editor visualizer software Avogadro. The auto-optimization tool of Avogadro was used to apply interactive interface, Universal Force Field (UFF), and Steepest descent algorithm. All the compounds were optimized and saved as a PDB file. To select the best hit, molecular docking was performed. Molecular docking simulations were performed using Auto Dock Vina's Broyden-Fletcher-Goldfarb-Shanno (BFGS) search algorithm. PyRx dock was used as an interface to run Auto Dock vina on the windows platform. In each round of molecular docking, the best hit compounds were ranked according to their binding affinity and further processed for analyzing the amino acid interaction. Briefly, a blind docking was performed for each compound to identify a potential binding region on the MRGPRX2 homology model. A rational docking simulation was then performed to get the most accurate binding mode for each compound. A blind docking was first performed by selecting the whole receptor area with exhaustiveness of 50 by AutoDock Vina. The docked pose of AutoDock Vina was very closely superimposed onto the original pose within the active site of MRGPRX2 with a root-mean-square deviation (RMSD) of ~0.8 Å, which was within the acceptable range (≤2 Å) for successful validation of self-docking. In post-docking analysis, the docked poses and relevant binding affinity scores of ligands were highly reproducible in AutoDock Vina when carried out in four to six independent runs (standard error: 0.45-0.9 kcal/mol). After identification of the binding site, focused docking was applied with exhaustiveness set to 50. Further validation of the binding pocket was done with the patch dock/firedock algorithm. The docked compounds were scored according to their binding score calculated from docking algorithms. The receptor and protein-ligand interactions visualization were done by PyMOL, maestro, and Discovery studio visualizer.

Drug-Like Properties of Novel Small Compound Antagonists

An online ADME prediction tool SwissADME (http://www.swissadme.ch) was used for measuring the drug-likeness of the novel small compounds. The drug-likeness was predicted by adopting Lipinski's Rule of 5 which is based on the ground rule on physicochemical properties of small compounds. The Rule of 5 predicts small compounds with molecular weight more than 500 Da, more than 5H-bond donors, more than 10H-bond acceptors, and the Log P (M Log P) more than 5 may likely have low absorption or membrane permeability. Therefore, small compounds that do not meet the criteria may unlikely become orally bioavailable as drugs.

Synthesis of Small Compound Antagonists

Instrumentation and Chemicals

All the chemicals and reagents were purchased from Sigma Aldrich, Alfa Aesar, Combi-Blocks, GLR Innovations, Spectrochem, TCI chemicals India and used without further purification. Rf values were determined using precoated Merck silica gel 60F254 aluminum sheets (Merck, Germany). The visualization of TLC plates was accomplished using the UV light and iodine vapors. $^1H$ NMR (400 MHz) was recorded on Bruker Avance-III HD FT-NMR spectrophotometer (Bruker, USA) and interpreted manually.

LC-MS spectra were recorded as detailed below. (a) Water Acquity UPLC H class equipped with PDA and acquity SQ detector; sunfire C18 (150 mm×4.6 mm) columns, 3.5 μM, the mobile phase A was 0.1% formic acid in Milli Q water (pH=2.70) and mobile phase B was 0.1% Formic acid in Milli Q water: Acetonitrile (10:90). For MS ESI probe and both positive and negative mode of Ionization was used. (b) Waters 996 photodiode array detector equipped with waters micromass ZQ detector. The Xtimate Welch C18 4.6*150 mm 5.0 μM column and 5 mM ammonium acetate and 0.1% formic acid (pH=3.50) in milli Q water as mobile phase A while mobile methanol as phase B was used. For MS ESI probe and both positive and negative mode of Ionization were used.

The percentage purity of the compounds was determined using high-performance liquid chromatography as detailed below. (a) Agilent Technologies. 1260 Series, Infinity-II with PDA detector and sunfire C18 (150 mm×4.6 mm), 3.5 μM column. The mobile phase A was 0.05% trifluoroacetic acid in milli Q water (pH=2.2), and mobile phase B was acetonitrile. The flow rate was 1.0 mL/min for a total run time of 17 min. (b) Waters Alliance e2695 with 2998 PDA detector with Atlantis C18 (150 mm×4.6 mm), 5.0 μM or Welch C18 (150 mm×4.6 mm), 5.0 μM column. The mobile phase A was 0.1% ammonia in Milli Q water (pH=10.5), and mobile phase B was acetonitrile. The flow rate was 1.0 mL/min with a total run time of 17 min. (c) Waters Acquity Ultra Performance LC connected with PDA and equipped with SQ detector. The XTIMATE 2.1*50 mm 1.8 μM column was used with a mobile phase A of 0.1% Formic acid in Milli Q water (pH=2.70) and mobile phase B of 0.1% formic acid in Milli Q water: Acetonitrile (10:90). The flow rate was 0.8 mL/min, and the samples were run for a total of 4 min.

SYNTHESIS AND CHARACTERIZATION OF GE0117

Scheme 1:
Preparation of the upper scaffold U1; Methyl 6-(2-methyl-1,3-dioxo-2,3-dihydro-1H-benzo[de] isoquinolin-5-yl)-7-ureido-2-naphthoate

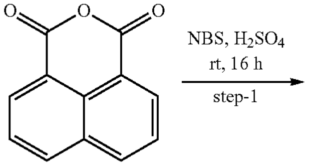

CAS No: 81-84-5

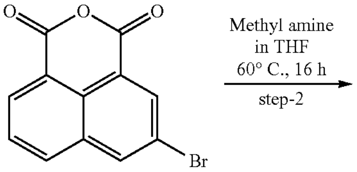

MW: 275.94
U1A1

-continued

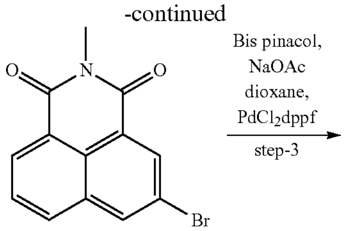

MW: 288.97
U1A2

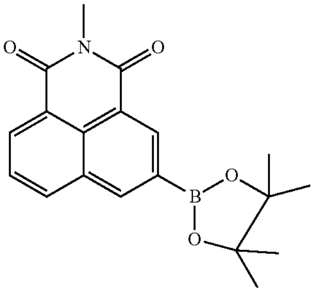

MW: 337.15
U1

Scheme 2:
Preparation of the lower scaffold L1; Methyl 6-(((trifluoromethyl)sulfonyl)oxy)-7-ureido-2-naphthoate

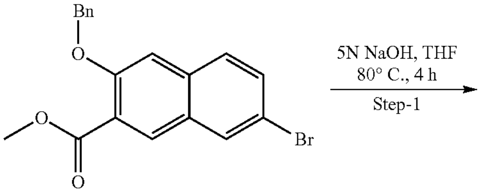

M.W: 371.06
L1A1

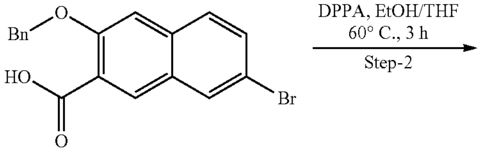

M.W: 357.20
L1A2

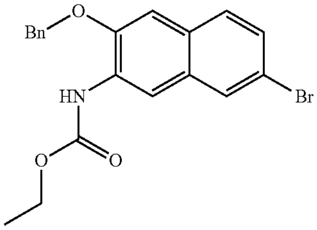

M.W: 400.27
L1A3

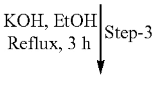

-continued

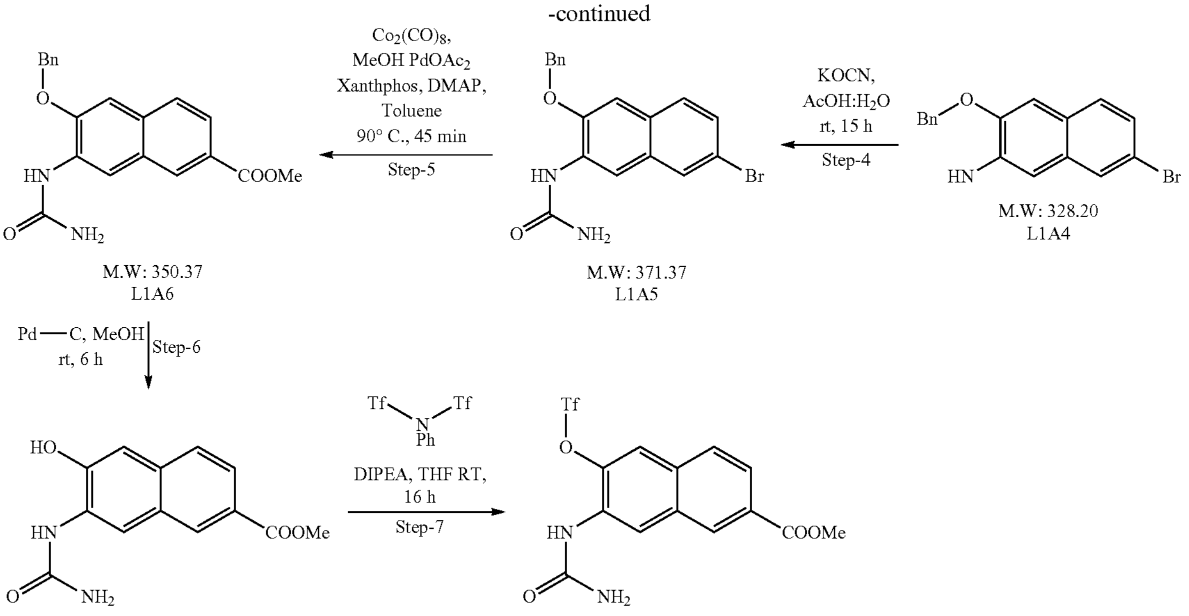

M.W: 328.20
L1A4

M.W: 371.37
L1A5

M.W: 350.37
L1A6

M.W: 260.25
L1A7

M.W: 392.32
L1

Scheme 3: Preparation of GE0117; Methyl 6-(2-methyl-1,3-dioxo-2,3-dihydro-1H-benzo[de]isoquinolin-5-yl)-7-ureido-2-naphthoate

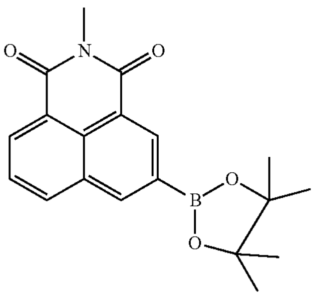

MW: 337.15
U1

+

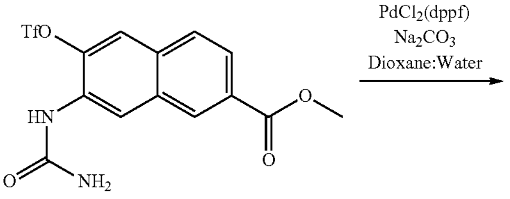

M.W: 392.03
L1

-continued

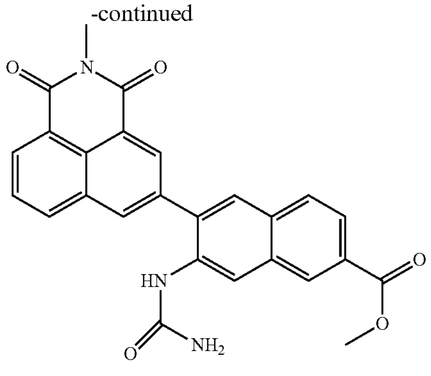

MW: 453.13
GE0117

The small compound antagonist GE0117 was synthesized by amalgamating the upper scaffold U1 with the lower scaffold L1, as demonstrated in Scheme 3. Three-step reactions and two intermediates synthesized the upper scaffold U1 as per the reaction scheme represented in Scheme 1. To a stirred solution of U1 (0.1 g, 0.3 mmol) and L1 (0.14 g, 0.35 mmol) in 1,4-Dioxane (10 ml), $Na_2CO_3$ (0.95 g, 0.9 mmol) was added at RT. The solution was purged with $N_2$ (g) for 15 min followed by adding $PdCl_2$(dppf) (0.02 g, 0.03 mmol); the reaction mixture was stirred at 100° C. for 16 h. After completing the reaction as monitored by TLC, the resulting reaction mixture was filtered through celite bed washed with ethyl acetate (50 mL). The filtrate was evaporated and the crude material was purified by reverse-phase prep-HPLC purification using 1M HCl in water/MeCN to yield brown solid color GE0117. $^1H$ NMR and LCMS characterized all the intermediates. Briefly, the upper scaffold U1 demonstrated molecular weights 337.15 (M+1) confirmed by LCMS. The lower scaffold L1 was synthesized by seven steps reactions as per Scheme 2. Briefly, the six intermediates (L1A2, L1A3, L1A4, L1A5, L1A6, and L1A7) were synthesized and characterized by $^1$H NMR and LCMS. The lower scaffold L1 synthesis was confirmed by characteristic $^1$H NMR and LCMS spectra.

Finally, GE0117 was synthesized by fusing the upper scaffold U1 with lower scaffold L1 in the presence of 1,4-Dioxane, $Na_2CO_3$, and $PdCl_2$(dppf) as per Scheme 3. The final product was proofed by its characteristic singlet peak for 1H NMR spectra (400 MHz, DMSO-d6) δ 8.64-8.53 (m, 6H), 8.03 (d, J=10, 2H), 7.98-7.85 (m, 3H), 6.56 (s, 1H) 6.60 (s, 1H), 3.93 (s, 3H), 3.45 (s, 3H). LCMS confirmed the purity (>95%) and molecular weight 545.1 (M+1) (the retention time of GE0117 in the HPLC column was about 1.936 minute; it showed >95% purity and 454.1 (M+1) molecular ion peak; the yield after isolation was about 6 wt %).

Synthesis and Characterization of GE0118

Scheme 4:
Preparation of the lower scaffold L2; dimethyl 3-(4,4,5,5-tetramethyl-1,3,2-dioxaborolan-2-yl) naphthalene-2,7-dicarboxylate

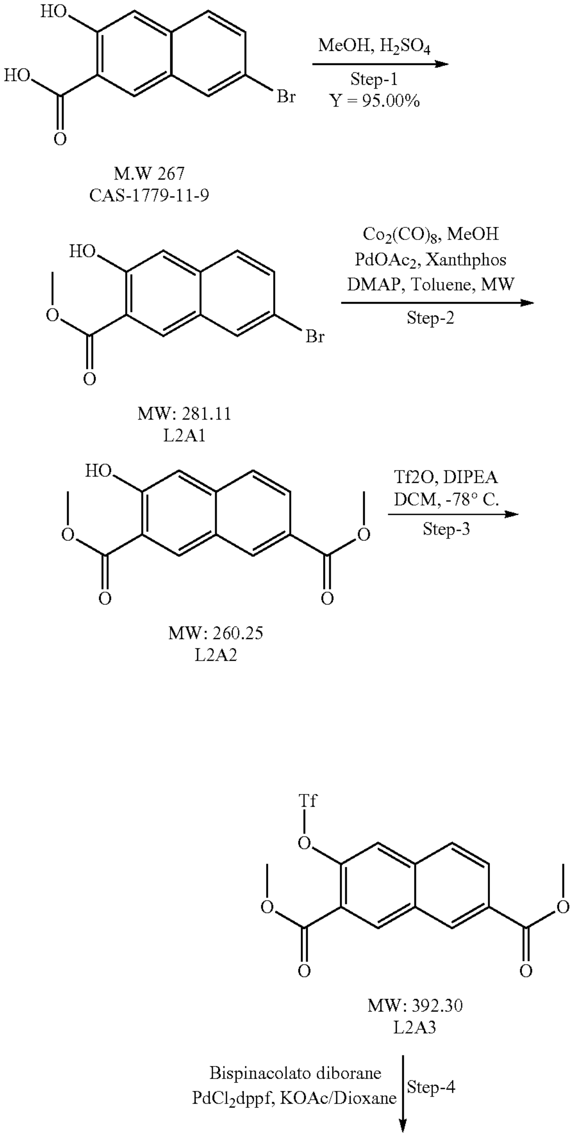

M.W 267
CAS-1779-11-9

MW: 281.11
L2A1

MW: 260.25
L2A2

MW: 392.30
L2A3

-continued

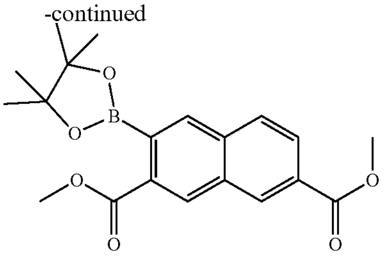

MW: 370.21
L2

Scheme 5:
Preparation of GE0118; Dimethyl 3-(2-methyl-1,3-dioxo-2,3-dihydro-1H-benzo[de]isoquinolin-5-yl) naphthalene-2,7-dicarboxylate

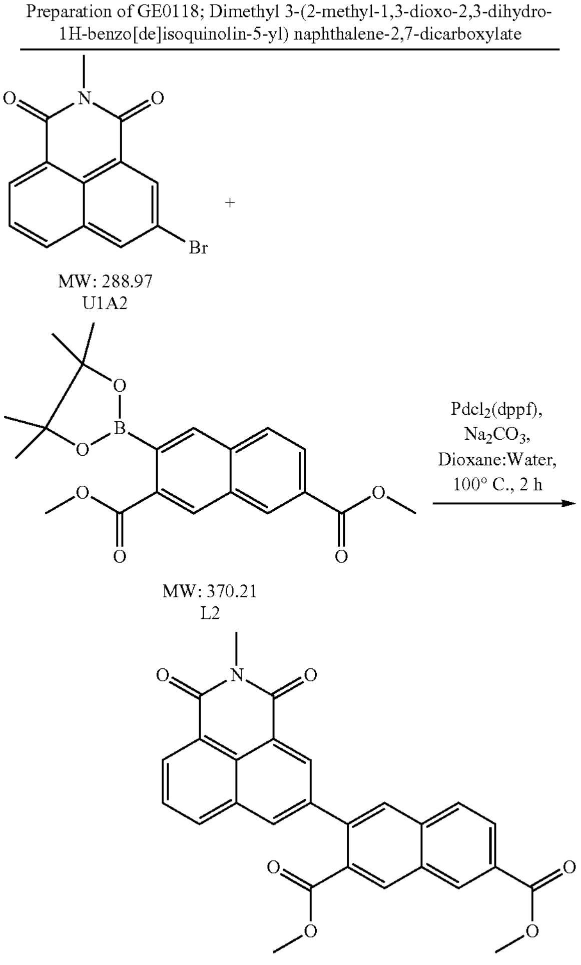

MW: 288.97
U1A2

+

MW: 370.21
L2

MW: 453.13
GE0018

The small compound antagonist GE0118 was synthesized by amalgamating the upper scaffold U1A2 with the lower scaffold L2 as per Scheme 5. The upper scaffold U1A2 (5-bromo-2-methyl-1H-benzo[de]isoquinoline-1,3(2H)-dione) was previously synthesized as an intermediate and represented in Scheme 1. The $^1$H NMR spectra of U1A2 showed characteristic singlet peak for $^1$H NMR (400 MHz, $CDCl_3$) δ 8.68 (d, J=1.6 Hz, 1H), 8.62 (d, J=7.2 Hz, 1H), 8.39 (s, 1H), 8.15 (d, J=8.4 Hz, 1H), 7.80 (t, J=7.6 Hz, 1H), 3.58 (s, 3H) and mass of 289.9 (M+1) by LCMS. The lower scaffold L2 was synthesized via Scheme 4. The three intermediates (L2A1, L2A2, and L2A3) and L2 were synthesized via four-step reactions and characterized by $^1$H NMR and LCMS. The lower scaffold L2 was characterized by $^1$H NMR (400 MHz, DMSO-d6) δ 8.81 (s, 1H), 8.73 (s, 1H), 8.17-8.10 (m, 3H), 3.93 (m, 3H) 3.92 (s, 3H), 3.89 (s, 3H), 1.36 (s, 12H) and the molecular mass of 371.4 (M+1) by LCMS.

The final reaction to getting GE0118 was done by fusing the upper scaffold U1A2 with lower scaffold L2 in the presence of 1,4-Dioxane, $Na_2CO_3$, and $PdCl_2$(dppf) as per Scheme 5. To a stirred solution of U1A2 (0.05 g, 0.18 mmol) and L2 (0.05 g, 0.17 mmol) in 1,4-Dioxane (10 ml), $Na_2CO_3$ (0.05 g, 0.54 mmol) was added at Room Temperature. The $N_2$ (g) was purged for 15 min followed by adding $PdCl_2$ (dppf) (0.012 g, 0.01 mmol), the reaction mixture was stirred at 100° C. for 2 h. After completing the reaction as monitored by TLC, the resulting reaction mixture was filtered through celite bed washed with ethyl acetate (50 mL). The filtrate was evaporated and eluted by 15% ethyl acetate in hexane to obtain off-white solid color compound GE0118. The NMR spectra of GE0118 demonstrated characteristic singlet peak for 1H NMR (400 MHz, DMSO-d6) δ 8.89 (s, 1H), 8.82 (s, 1H), 8.55 (t, J=12 Hz 3H), 8.44 (s, 1H) 8.30 (s, 1H), 8.32-8.16 (m, 2H), 7.94 (t, J=7.6 Hz, 1H), and molecular mass of 454.2 (M+1) by LCMS with >95% purity (the retention time of GE0118 in the HPLC column was about 10.331 minute; it showed >95% purity and 454.2 (M+1) molecular ion peak; the yield after isolation was about 26.5 wt %).

Synthesis and Characterization of GE0119

Scheme 6:
Preparation of the lower scaffold L3; 5-bromo-2-methyl-1H-benzo[de]isoquinoline-1,3(2H)-dione

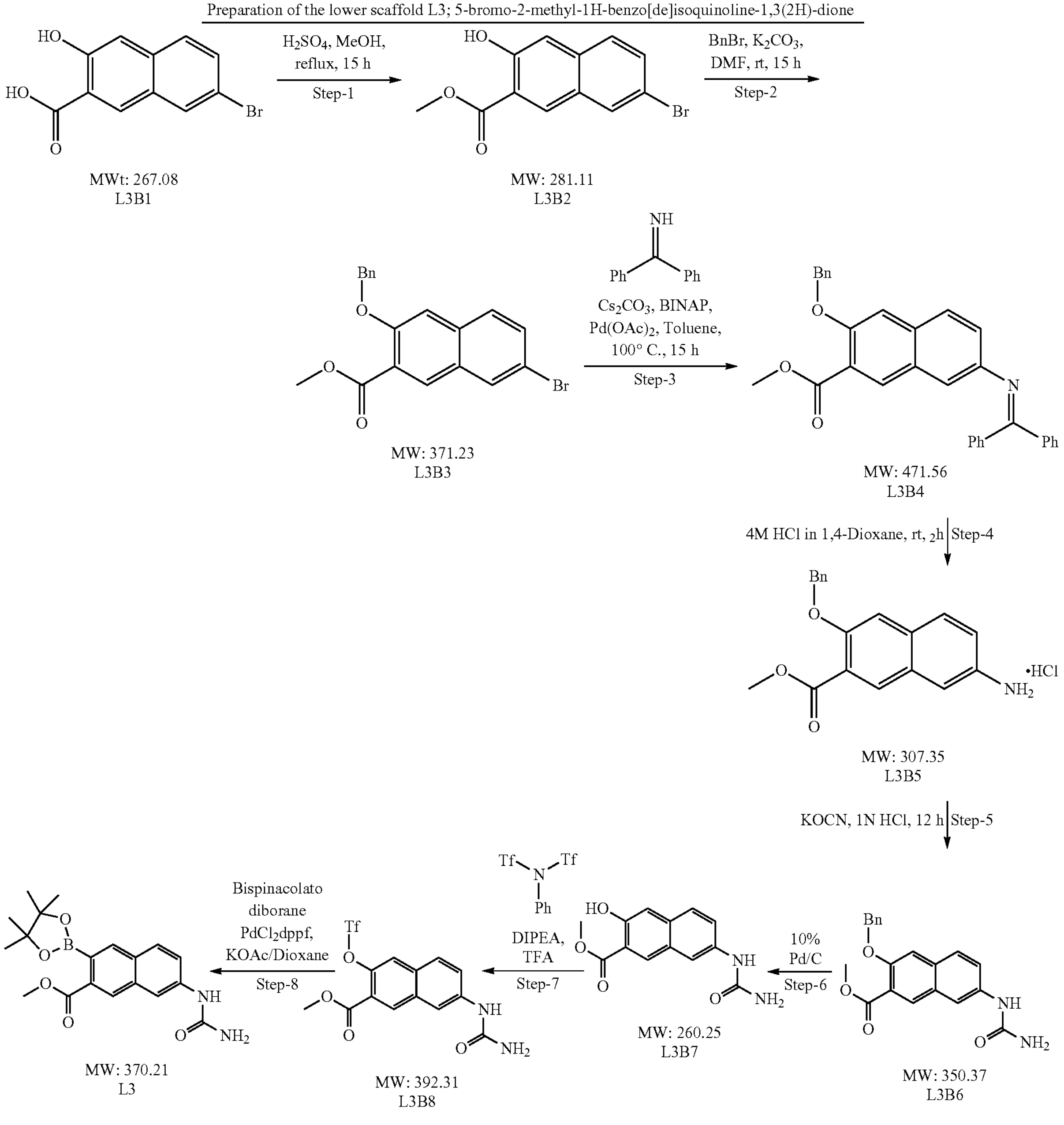

Scheme 7:
Preparation of GE0119; Methyl 3-(2-methyl-1,3-dioxo-2,3-dihydro-1H-benzo[de]isoquinolin-5-yl)-7-ureido-2-naphthoate

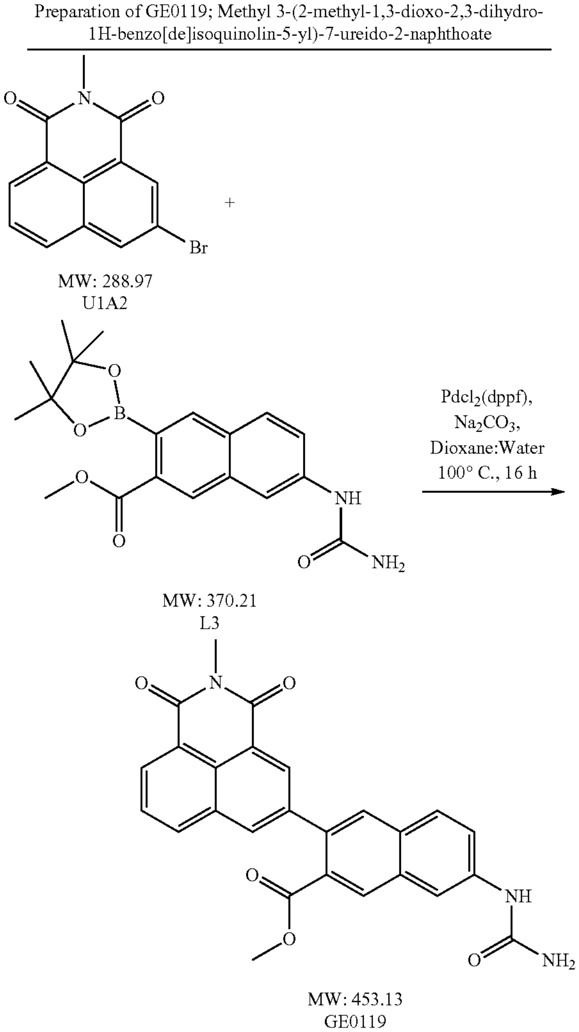

The small compound antagonist GE0119 was synthesized by fusing upper scaffold U1A2 with the lower scaffold L3 as per Scheme 7. The upper scaffold U1A2 has been previously synthesized and characterized (in Scheme 1 of GE0117), and the lower scaffold L3 was synthesized via Scheme 6. Briefly, the chemical reactions included 8 steps and seven intermediates (L3B2, L3B3, L3B4, L3B5, L3B6, L3B7, and L3B8), which were characterized by $^1$H NMR and LCMS. The $^1$H NMR spectra of intermediate L3 showed characteristic singlet peak of (400 MHz, DMSO-d6) δ 8.89 (s, 1H), 828 (s, 1H), 8.09 (s, 1H), 7.92-7.85 (m, 2H), 7.65 (d, J=8.8 Hz, 1H), 6.03 (s, 2H), 3.88 (s, 3H), 1.35 (s, 12H) and the molecular weights 371.49 (M+H) was confirmed by LCMS.

Finally, GE0119 was synthesized by a chemical reaction of U1A2 with L3 in $PdCl_2$(dppf), $Na_2CO_3$, and Dioxane: water as per Scheme 7. To a stirred solution of U1A2 (0.1 g, 0.3 mmol) and L3 (0.14 g, 0.35 mmol) in 1,4-Dioxane (10 ml), $Na_2CO_3$ (0.95 g, 0.9 mmol) was added at Room Temperature. The $N_2$ (g) was purged for 15 min followed by the addition of $PdCl_2$(dppf) (0.02 g, 0.03 mmol) and the reaction mixture was stirred at 100° C. for 16 h. After completion of the reaction as monitored by TLC, the resulting reaction mixture was filtered through celite bed washed with ethyl acetate (50 mL). The filtrate was evaporated, and the crude material was purified by normal phase prep-HPLC purification using n-heptane/IPA to yield brown color compound GE0119. GE0119 was characterized by $^1$H NMR spectra of (400 MHz, DMSO-d6) δ 8.38 (s, 1H), 8.52 (s, 3H), 8.40 (d, J=9.6 Hz 2H), 8.24 (s, 1H) 8.05 (s, 1H), 7.97-7.90 (m, 2H), 7.72 (d, J=8.0 Hz, 1H), 3.66 (s, 3H), 3.43 (s, 3H) and mass of 454.1 (M+1) by LCMS with >95% purity (the retention time of GE0119 in the HPLC column was about 9.071 minute; it showed >95% purity and M+1 peak of 454.1; the yield after isolation was about 6 wt %).

Synthesis and Characterization of GE1109

Scheme 8:
Preparation of Upper scaffold U2; 6-Bromo-1H-phenalen-1-one

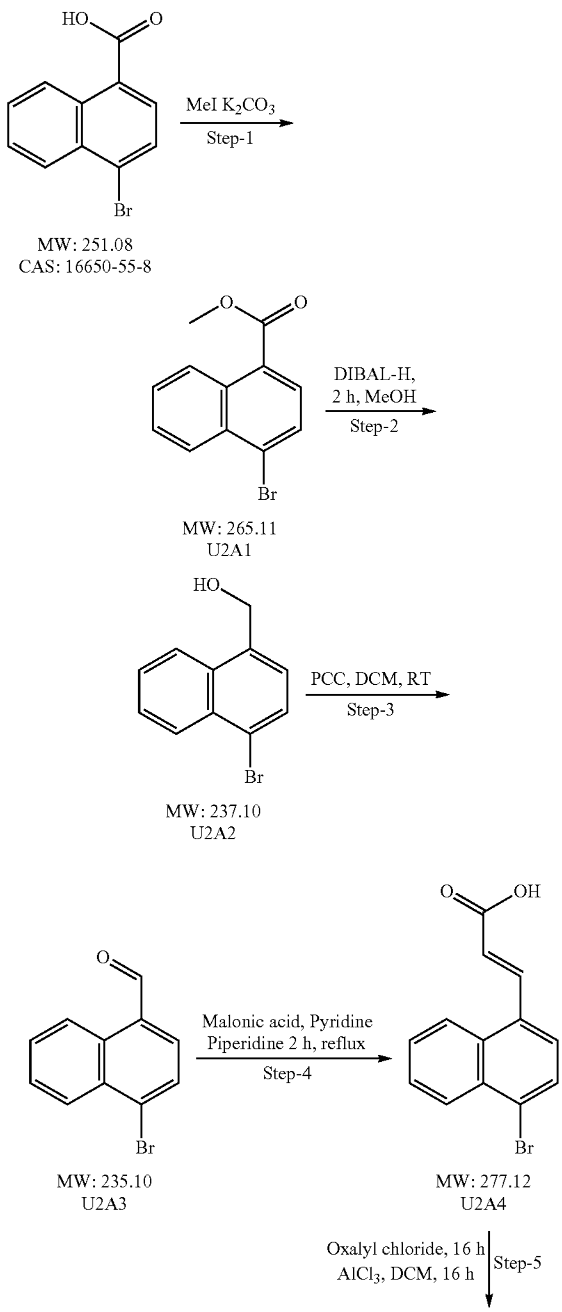

-continued

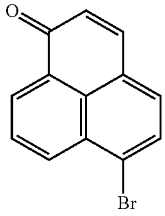

MW: 259.10
U2

Scheme 9:
Preparation of GE1109; methyl 3-(1-oxo-1H-phenalen-6-yl)-7-ureido-2-naphthoate

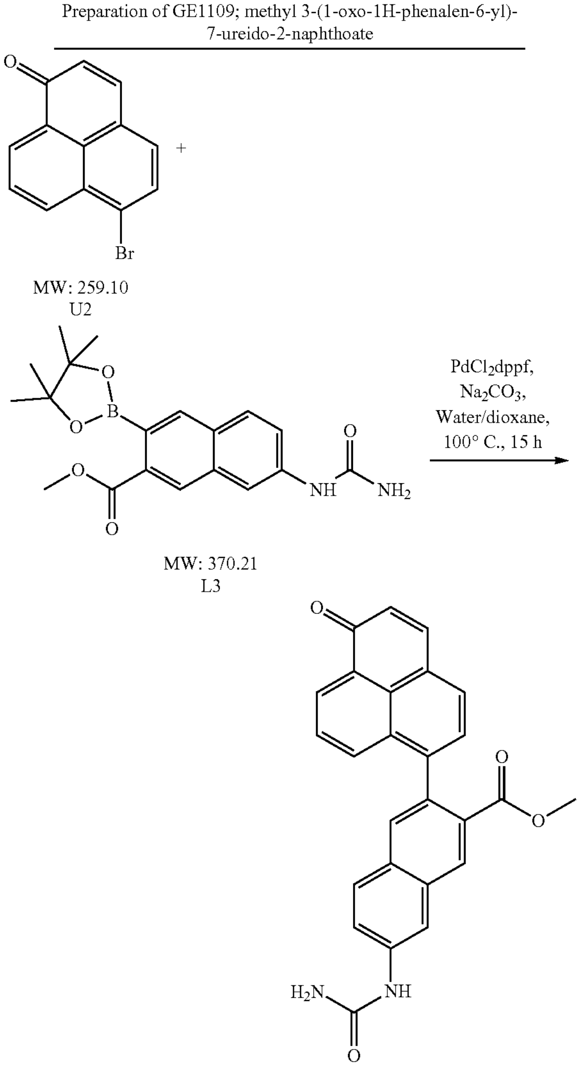

MW: 259.10
U2

MW: 370.21
L3

MW: 422.44
GE1109

The small compound antagonist GE1109 was synthesized by a chemical reaction of upper scaffold U2 with the lower scaffold L3 as per Scheme 9. A 5 steps chemical reaction synthesized the upper scaffold U2 as per Scheme 8; both $^1$H NMR and LCMS characterized the 4 intermediates. The upper scaffold U2 showed characteristic $^1$H NMR peak (400 MHz, CDCl3) δ 8.68 (dd, J=7.6 Hz, 1H). 8.62 (d, J=8.4 Hz, 1H), 7.90-7.86 (m, 2H) 7.71 (d, J=10 Hz, 1H) 7.56 (d, J=8.4 Hz, 1H) 6.75 (d, J=8.8 Hz, 1H), and molecular mass of 259.18, 261.2 (M & M+2) by LCMS. The lower scaffold L3 was similar to GE0119 and was previously synthesized as shown in Scheme 6 and characterized as described above.

Finally, GE1109 was synthesized by amalgamating the upper scaffold U2 with lower scaffold L3 in the presence of $PdCl_2$(dppf), $Na_2CO_3$, and water/dioxane and characterized by both $^1$H NMR and LCMS. GE1109 demonstrated the $^1$H NMR spectra of (400 MHz, DMSO-d6) δ 8.96 (s, 1H), 8.51-8.48 (m, 2H), 8.26 (s, 1H), 8.10-8.06 (m, 2H), 7.95-7.85 (m, 3H), 7.78 (t, J=7.6 Hz, 1H), 7.71 (d, J=9.2 Hz, 1H), 7.62 (d, J=7.2 Hz, 1H), 6.73 (d, J=9.6 Hz, 1H), 6.06 (s, 2H), 3.43 (s, 3H) and molecular mass of 423.44 (M+1) by LCMS with >95% purity (the retention time of GE1109 in the HPLC column was about 2.062 minute; it showed >95% purity and M+1 peak of 423.44; the yield after isolation was about 20 wt %).

Synthesis and Characterization of GE1110

Scheme 10:
Preparation of the upper scaffold U3; 5-Bromo-9-hydroxy-1-methyl-1H-phenalene-2-carbaldehyde

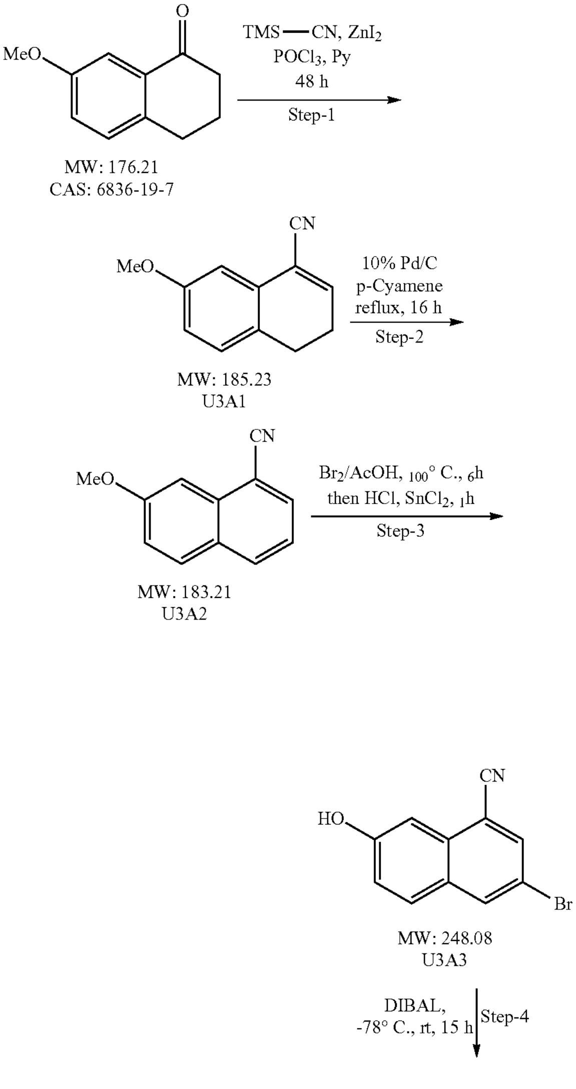

MW: 176.21
CAS: 6836-19-7

MW: 185.23
U3A1

MW: 183.21
U3A2

MW: 248.08
U3A3

-continued

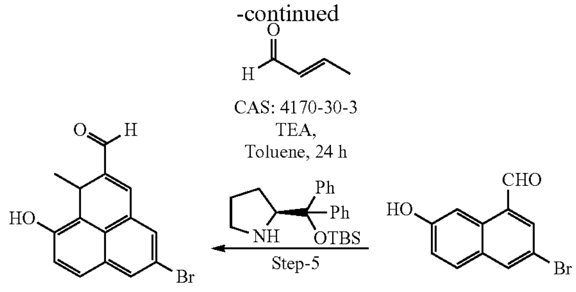

MW:303.15
U3

MW:251.08
U3A4

Scheme 11:
Preparation of GE1110; Dimethyl 3-(2-formyl-9-hydroxy-1-methyl-1H-phenalen-5-yl) naphthalene-2,7-dicarboxylate

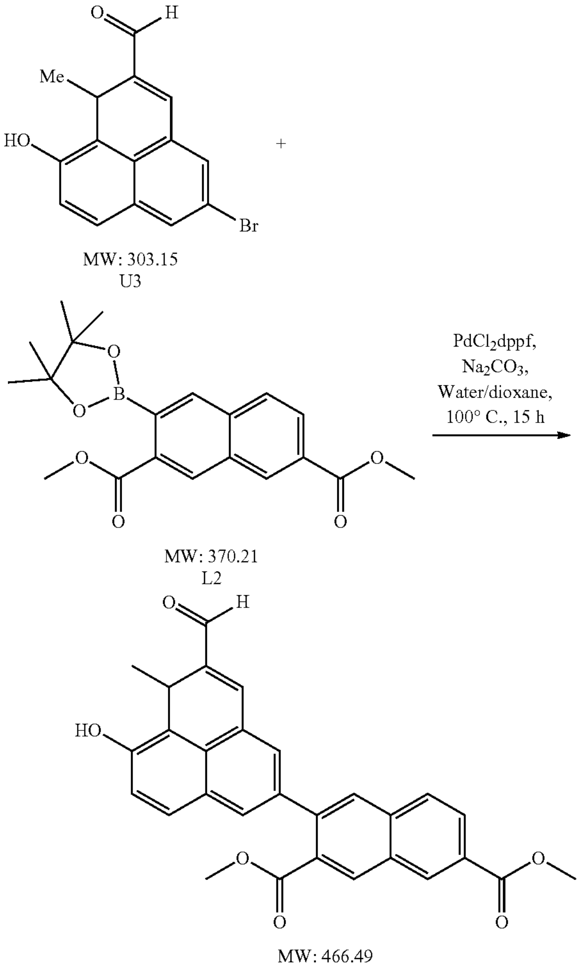

MW: 303.15
U3

MW: 370.21
L2

MW: 466.49
GE1110

The small compound antagonist GE1110 was synthesized by a chemical reaction of upper scaffold U3 with the lower scaffold L2 as per Scheme 11. Briefly, the upper scaffold U3 synthetic scheme includes 5 steps chemical reaction and 4 intermediates (Scheme 10). Both $^1H$ NMR and LCMS characterized all the intermediates. The upper scaffold U3 demonstrated characteristic $^1H$ NMR peak (400 MHz, DMSO-d6) δ 10.23 (s, 1H), 9.65 (s, 1H), 8.04 (s, 1H), 7.86-7.66 (m, 3H), 7.24 (d, J=8.8 Hz, 1H), 4.38 (q, 1H), 1.19 (d, J=6.8 Hz, 3H) and molecular mass of 303.2 & 305.1 (M & M+2) by LCMS. The lower scaffold L2 was similar to GE0118 and was previously synthesized as shown in Scheme 4 and characterized as described above.

The final synthesis step includes the reaction of the upper scaffold U3 with lower scaffold L2 in the presence of $PdCl_2$(dppf), $Na_2CO_3$, and water/dioxane. A solution of U3 (0.04 g, 0.13 mmol), L2 (0.058 g, 0.15 mmol) and $Na_2CO_3$ (0.041 g, 0.39 mmol) in 1,4-dioxane (0.8 mL): $H_2O$ (0.2 mL) was purged with $N_2$ (g) for 5 min. Then $PdCl_2$(dppf) (0.009 g, 0.013 mmol) was added to the reaction mixture and stirred at 100° C. for 15 h. After completion of the reaction as indicated by TLC, the resulting reaction mixture was filtered through celite bed and washed with ethyl acetate (30 mL). The filtrate was evaporated, and crude material (0.1 g) was purified by column chromatography (0-5% ethyl acetate in hexane) to obtain yellow color solid compound GE1110. GE1110 demonstrated the characteristic $^1H$ NMR signal (400 MHz, DMSO-d6) δ 10.17 (s, 1H), 9.68 (s, 1H), 8.84 (s, 1H), 8.70 (s, 1H), 8.22 (s, 1H), 8.19-8.13 (m, 2H), 7.88 (s, 1H), 7.78 (s, 1H), 7.76 (s, 1H), 7.55 (s, 1H) 7.28 (d, J=8.8 Hz, 1H), 4.44-4.42 (m, 1H), 3.95 (s, 3H), 3.69 (s, 3H), 1.25 (d, J=9.2 Hz, 3H) and molecular mass of 467.54 (M+1) by LCMS with >95% purity (the retention time of GE1110 in the HPLC column was about 2.614 minute; it showed >95% purity and M+1 peak of 467.54; the yield after isolation was about 31.5 wt %).

Synthesis and Characterization of GE1111

Scheme 12:
Preparation of GE1111; Methyl 3-(2-formyl-9-hydroxy-1-methyl-1H-phenalen-5-yl)-7-ureido-2-naphthoate

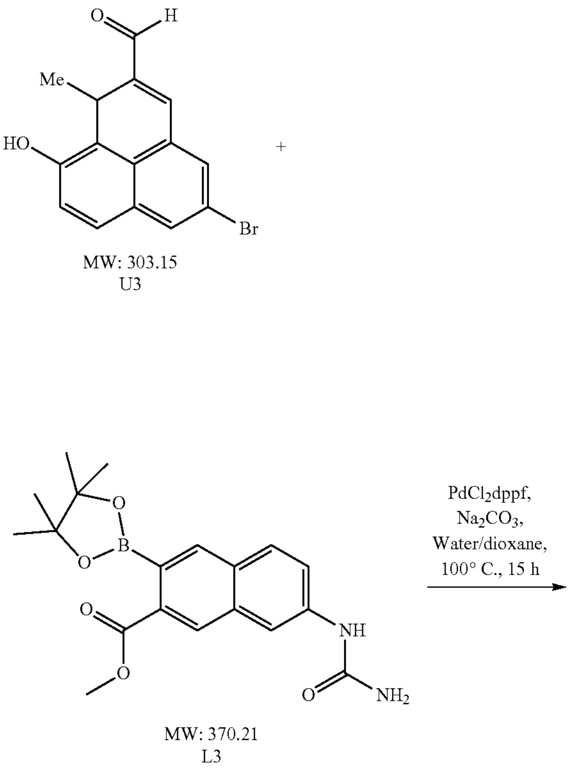

MW: 303.15
U3

MW: 370.21
L3

-continued

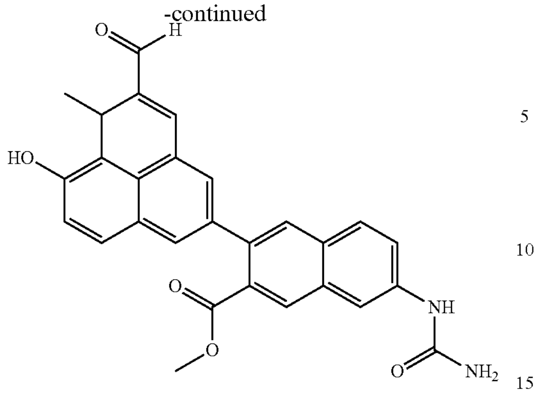

MW: 466.49
GE1111

The small compound antagonist GE1111 was synthesized by a chemical reaction of the upper scaffold U3 with the lower scaffold L3 as per Scheme 12. The upper scaffold U3 and lower scaffold L3 synthetic scheme was previously described in Scheme 10 and Scheme 6, respectively. A solution of U3 (0.06 g, 0.19 mmol), L3 (0.08 g, 0.23 mmol) and $Na_2CO_3$ (0.041 g, 0.39 mmol) in 1,4-Dioxane (1.6 mL): $H_2O$ (0.4 mL) was purged with $N_2$ (g) for 5 min. Then, $PdCl_2$(dppf) (0.014 g, 0.019 mmol) was added to reaction mixture and stirred at 100° C. for 15 h. After completion of the reaction as indicated by TLC, the resulting reaction mixture was filtered through celite bed and washed with ethyl acetate (50 mL). The filtrate was evaporated, and crude was purified by normal phase prep-HPLC purification to obtain yellow color compound GE1111. Both $^1H$ NMR and LCMS characterized all the intermediates. The final synthesis step includes the reaction of the upper scaffold U3 with lower scaffold L3 in the presence of $PdCl_2$(dppf), $Na_2CO_3$, and water/dioxane. The synthesis of GE1111 was confirmed by its characteristic $^1H$ NMR spectra of (400 MHz, DMSO-d6) δ 10.10 (bs, 1H), 9.68 (s, 1H), 8.92 (s, 1H), 8.28 (s, 1H), 8.16 (s, 1H), 7.96-7.91 (m, 2H), 7.81 (s, 1H), 7.75-7.65 (m, 3H), 7.51 (s, 1H), 7.26 (d, J=8.8 Hz 2H), 6.04 (bs, 2H), 4.44-4.42 (m, 1H), 3.67 (s, 3H), 1.26-1.24 (d, J=6.8 Hz, 3H) and molecular mass of 467.59 (M+1) by LCMS with >95% purity (the retention time of GE1111 in the HPLC column was about 2.148 minute; it showed >95% purity and M+1 peak of 467.59; the yield after isolation was about 15.5 wt %).

Results

Homology Modeling and Pharmacophore Identification

Figure 1B:
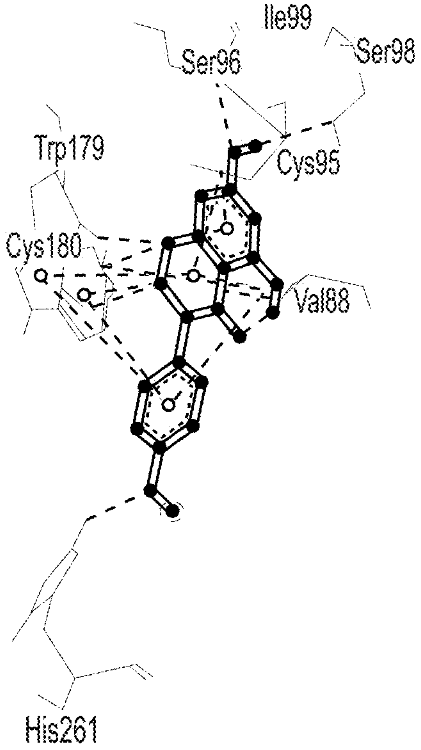
FIG. 1B is a 3D amino acid interaction map showing the interaction of genistein at the binding site of N-terminal amino acid residues of MRGPRX2.
Figure 1C:
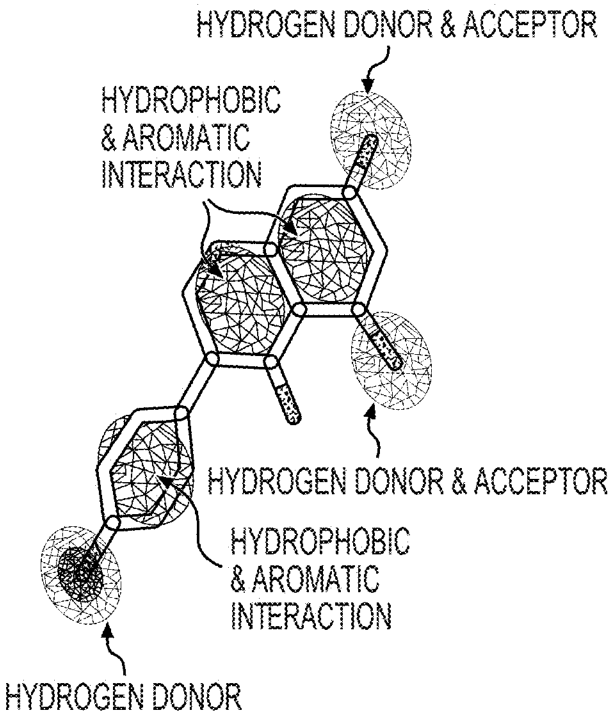
FIG. 1C is a 3D illustration of the pharmacophore developed from the genistein binding site on MRGPRX2.
Figure 2A:
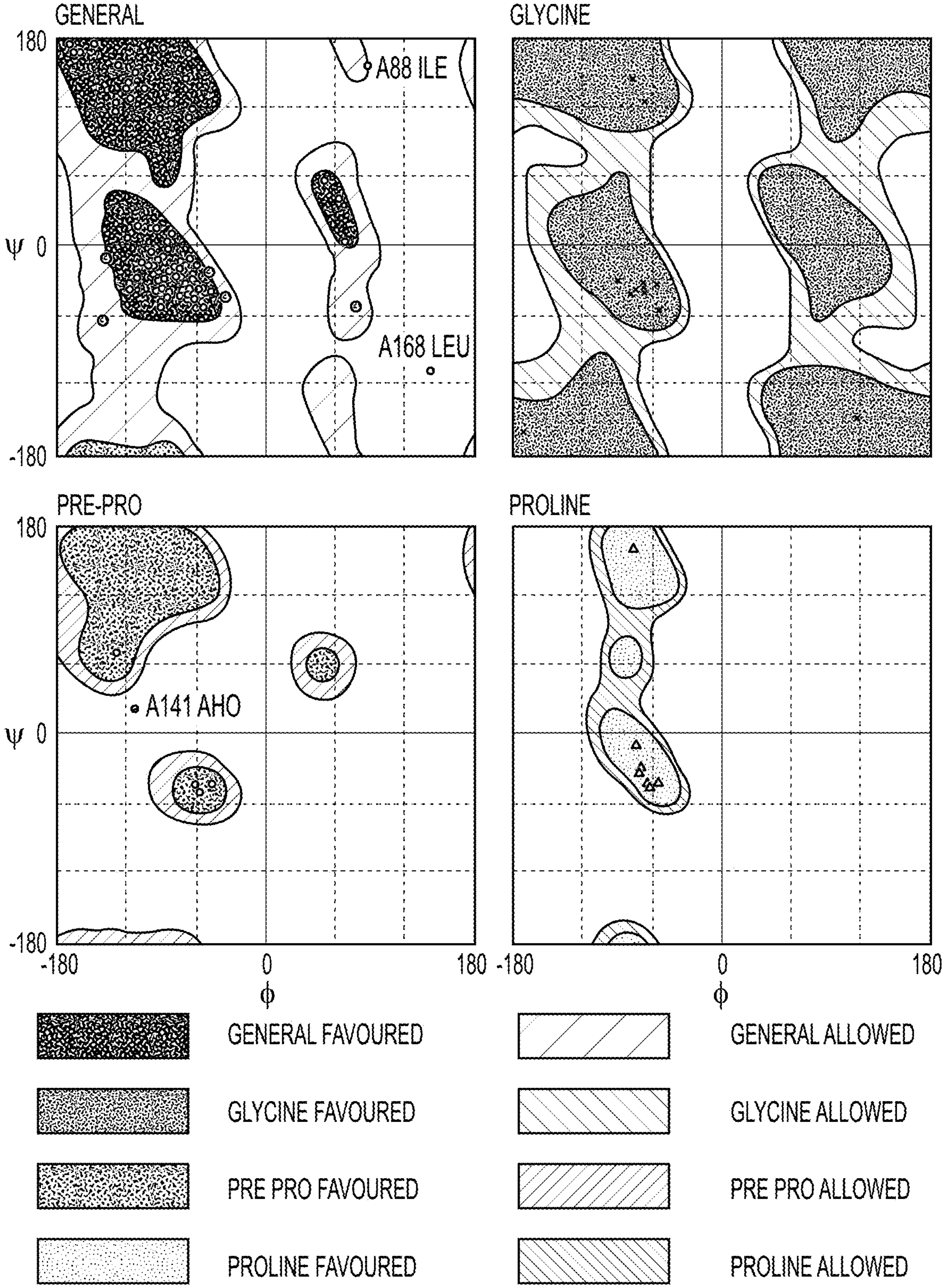
FIG. 2A is the Ramachandran plot representing 98.8% amino acid residues in the favored region with three residues in the outlier region.
Figure 2B:
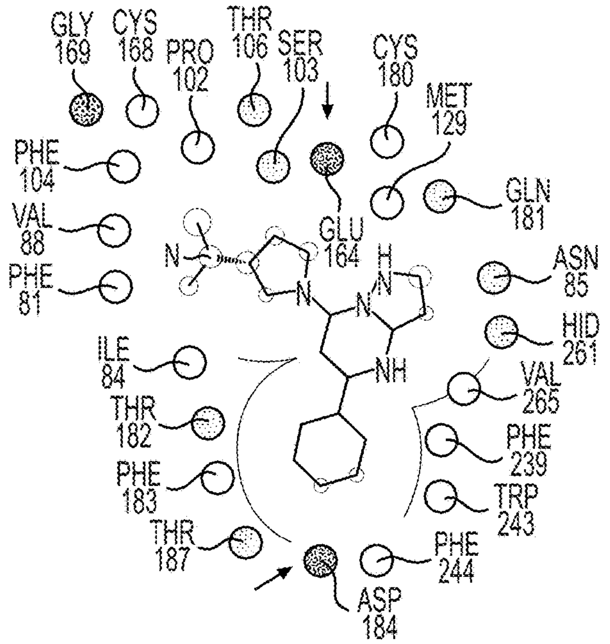
FIG. 2B is a schematic showing the 2D receptor-drug interaction view of ZINC72453573 with MRGPRX2. The receptor amino acid residues are presented as circles with amino acid name and number with ZINC72453573 at the center. The negatively charged residues GLU164 and ASP184 are highlighted by arrows.
Figure 2C:
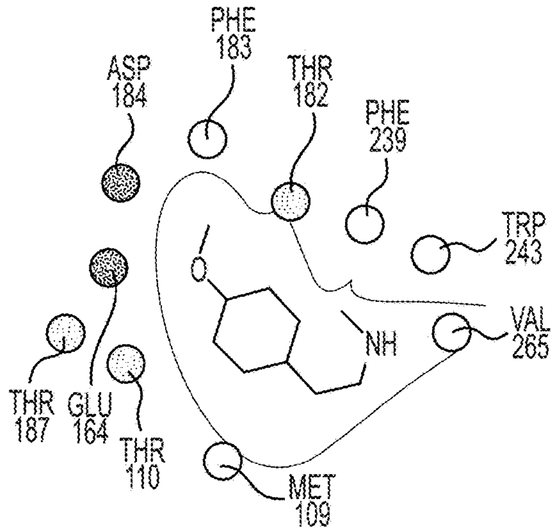
FIG. 2C is a schematic showing the 2D receptor-drug interaction view of C48/80 with the MRGPRX2 model.

To get insight into the 3D structure and ligand binding sites of MRGPRX2, a homology model of MRGPRX2 was developed since the crystallographic 3D structure of MRGPRX2 on RCSB Protein Data Bank is not available. MRGPRX2 is a class A orphan receptor and structurally similar to opioid GPCRs. Three MRGPRX2 homology models were developed and out of three developed models, the final selected MRGPRX2 model has 98.8% of amino acid residues at favored or at allowed regions (FIG. 1A). With Schrodinger Desmond's help, the energy of the full receptor structure was minimized in the most thermodynamically stable configuration, which was then validated by Ramachandran plot and Auto dock vina molecular docking (FIGS. 2A-2C). The experimental data on these ligands' structure-function relationship as an MRGPRX2 agonist is not well established. The cyclized variant of C48/80 containing a tetra-hydro isoquinoline (THIQ) motif was seven times more potent than C48/80 as an MCs degranulator. A common THIQ motif and bulky hydrophobic group with charged nitrogen nearby as a common structure in most of the known small molecule MRGPRX2 agonists such as non-steroidal neuromuscular blocking drugs (NMBDs), and fluoroquinolone antibiotics. The MRGPRX2 agonist shares common basic and hydrophobic domain structural features and is collectively called basic secretagogue or cationic-amphiphilic ligands. A GPCR dependent activity of basic secretagogue on MCs was also reported. Genistein has been used to identify the ligand's pharmacophore and perform a structure-based drug design to develop a potent small compound MRGPRX2 antagonist. The MRGPRX2 receptor was docked with genistein via Auto Dock vina and visualized by PyMOL, Schrodinger maestro suite and Discovery studio visualizer (FIGS. 1A-1C). The active site pre-defined from the MRGPRX2-genistein model was analyzed to locate the interactive amino acid residues. This complex was used as the structure for designing and screening small compounds. The amino acid interaction map demonstrates genistein interaction with the N-terminal extracellular domain of the MRGPRX2, via residues Ser96, Ser98, His261, Cys180, Trp179, Cys95, Val88, and Cys180 (FIG. 1B). The docked MRGPRX2-genistein complex was further evaluated and used to develop the pharmacophore model by the help of Pharmit. Several pharmacophore regions of genistein were identified, which demonstrates several contacts of genistein with amino acid of N terminal region of MRGPRX2 binding site. The pharmacophore of genistein has been determined to contain two hydroxyl groups of chromone ring as hydrogen donor and acceptor, hydroxyl group of phenol ring as hydrogen donor, phenol ring as hydrophobic and aromatic and chromone ring as hydrophobic and aromatic pharmacophore (FIG. 1C).

Designing of Small Compound Antagonists and in-Silico Screening

To select functional groups that can improve the binding affinity of MRGPRX2 antagonists, an in silico library of small compounds has been designed and screened via molecular docking and post docking analysis. The blind docketing results show that all the molecules localized, with high frequency, in a similar pocket as lead compound (data not shown). The rational docking simulation results show that all derivatives are located in the same binding pocket, assuming a similar binding pose, and their binding affinity for the MRGPRX2 was comparatively high compared to genistein (data are not shown). A hybrid combination of bromobenzo[de]isoquinoline/Phenalen-1-one with naphthoate has been identified, which significantly improves the binding affinity as well as the ligand-amino acid interaction. A series of compounds have been designed by substituting several functional groups such as carboxylic, methyl acetate, hydroxyl, amides, methyl, and aryl-OH aryl-COOH, halogen, and heterocyclic groups in the hybrid structure at different carbon positions. These compounds were tested against MRGPRX2 via molecular docking in a similar way. A significantly increased binding affinity and amino acid interaction was discovered by substituting the hydrogen atom at C17/C18 and C21/C22 in the naphthoate ring with methyl acetate and amide, as shown in Structure 1 and Structure 2 below.

Structure 1

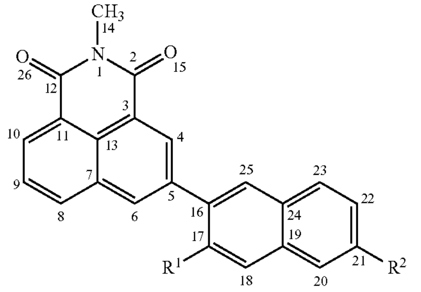

Structure 2

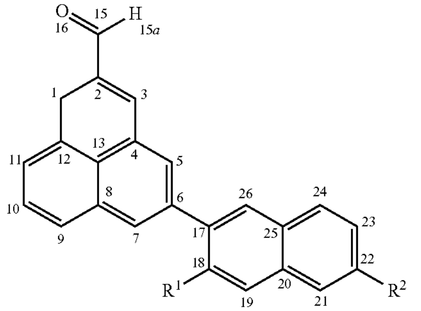

Figure 3A:
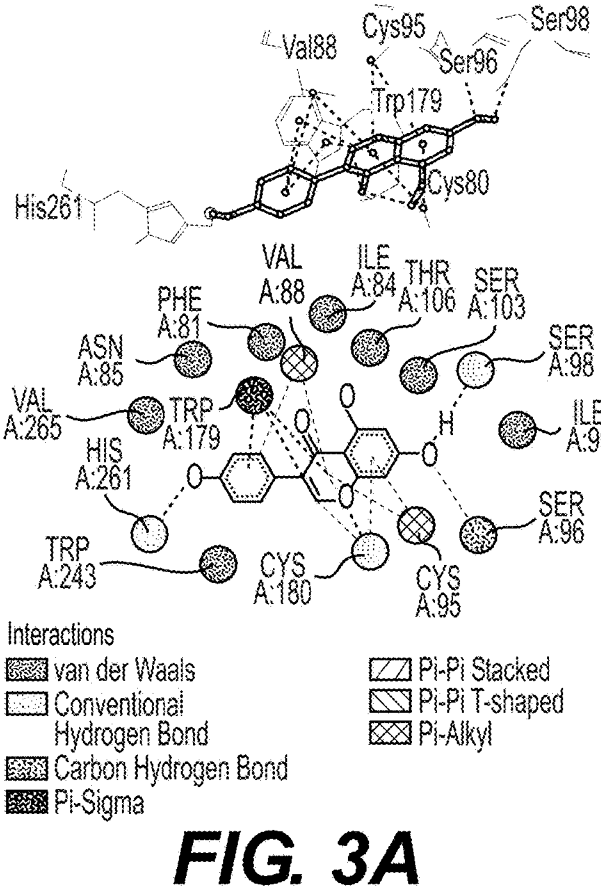
FIGS. 3A-3H are schematics showing the 3D and 2D binding pose and amino acid interaction map of genistein (FIG. 3A), C48/80 (FIG. 3B), and the small compound antagonists GE0117 (FIG. 3C), GE0118 (FIG. 3D), GE0119 (FIG. 3E), GE1109 (FIG. 3F), GE1110 (FIG. 3G), and GE1111 (FIG. 3H) with MRGPRX2.
Figure 3B:
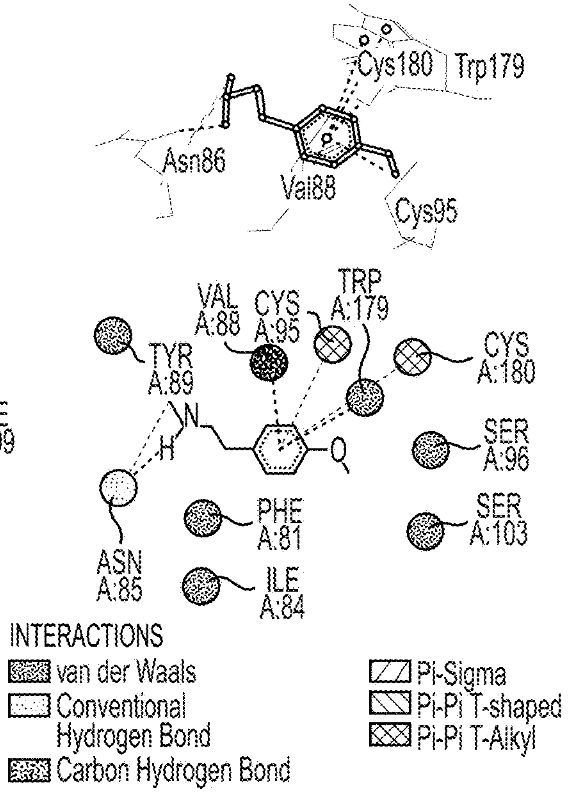
Figure 3C:
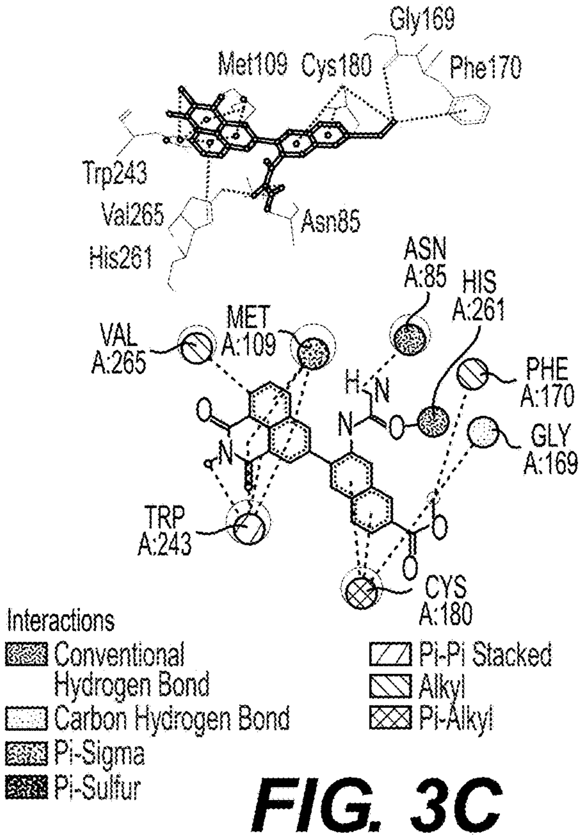
Figure 3D:
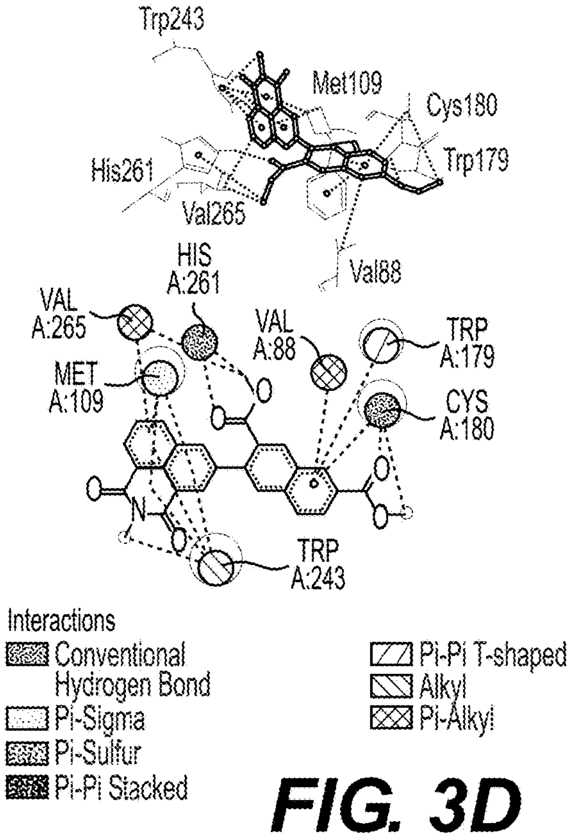
Figure 3E:
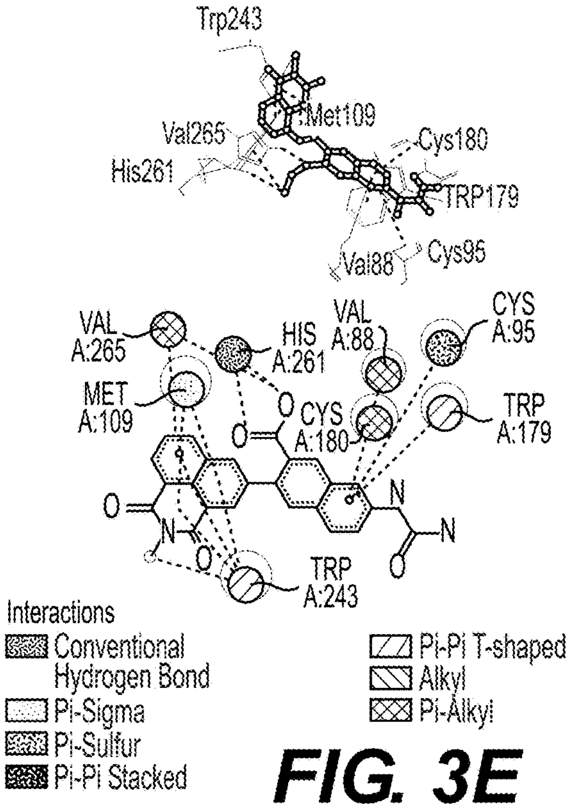
Figure 3F:
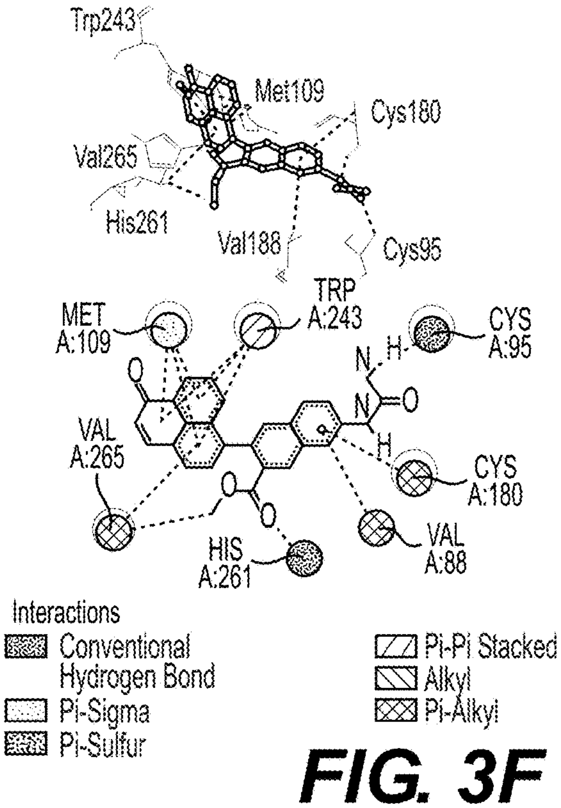
Figure 3G:
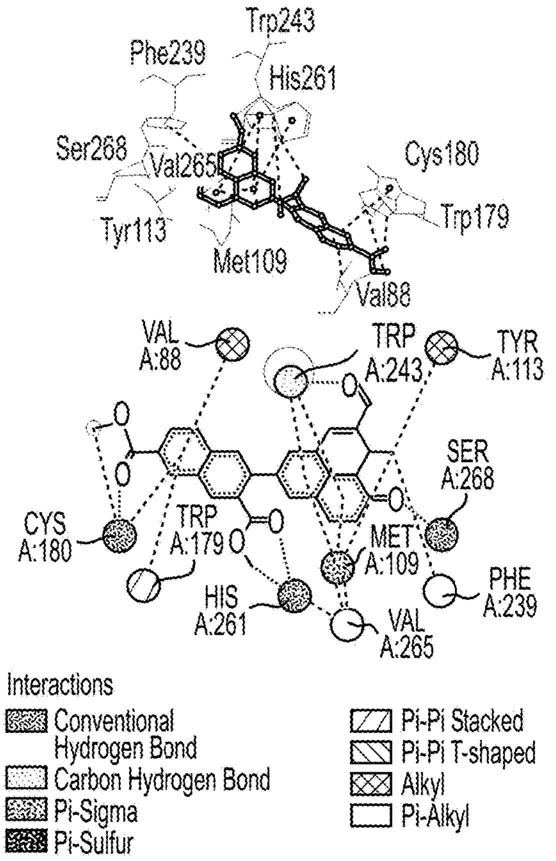
Figure 3H:
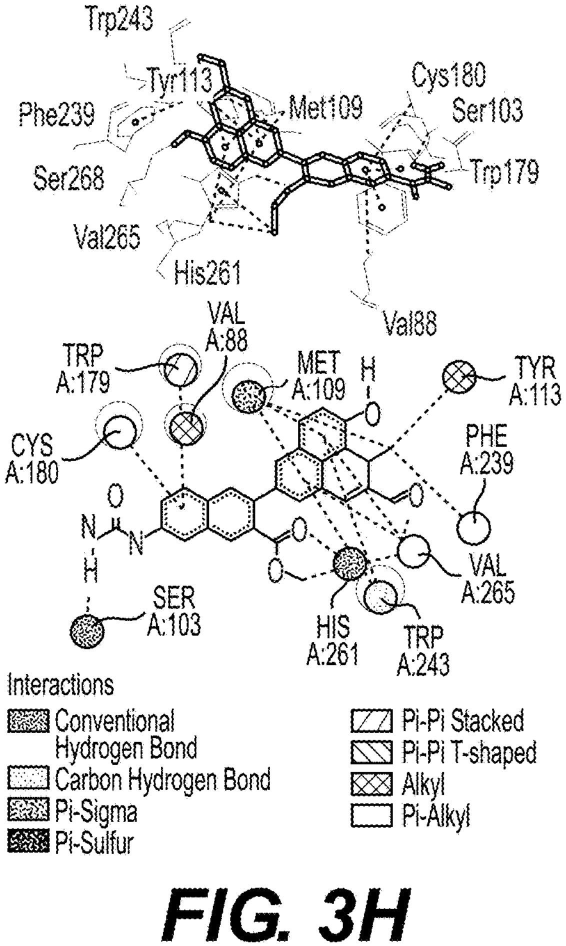

After the screening, based on the binding affinity and synthesis feasibility, six small compounds were selected and analyzed by post docking to check the amino acid interaction. As compared to genistein, these compounds show significantly high binding affinity and improved the amino acid interaction within the binding pockets via several hydrogen bonds, Π-sigma, Π-Π stacking, Π-Π T shaped, Π-alkyl, and pi-sulfur bonds (Table 1). FIGS. 3A-3H illustrate the 3D and 2D amino acid interaction of genistein, C48/80, and small compound antagonist with MRGPRX2. The in-silico results show that the six small compounds bind at the same binding site with high affinity inside the MRGPRX2 binding pocket located in the N-terminal region. As shown in FIG. 3A, genistein shows one Pi sigma and two pi-pi T-shaped bonds with TRP179; one conventional hydrogen bond with HIS261; one conventional hydrogen bond, one van der waals, and two pi-alkyl bonds with CYS180; one van der Waals bond with SER96, one conventional hydrogen bond with SER98 and two pi-alkyl bonds with VAL88. As shown in FIG. 3B, compound 48/80 shows one pi-pi T-shaped bond with TRP179; one pi-pi alkyl bond with CYS180; one pi-sigma bond with VAL88; one pi-alkyl bond with CYS95 and one conventional hydrogen and one van der Waals bond with ASN85. As shown in FIG. 3C, GE0117 shows one pi-sigma, one pi-sulfur and one-alkyl bond with MET109; one pi-alkyl bond with VAL265; three pi-pi stacked and one pi-alkyl bond with TRP243; one conventional hydrogen bond with ASN85; one conventional hydrogen bond with HIS261; one pi-alkyl bond with PHE170; one carbon-hydrogen bond with GLY169 and three pi-alkyl bonds with CYS180. As shown in FIG. 3D, GE0118 shows one pi-sigma, and two pi-sulfur bonds with MET109; two pi-alkyl bonds with VAL265; three pi-pi stacked and one pi-alkyl bond with TRP243; one conventional hydrogen bond and one pi-alkyl bond with HIS261; one pi-alkyl bond with VAL88; one pi-pi stacked bond with TRP179; one conventional hydrogen and two pi-alkyl bonds with CYS180. As shown in FIG. 3E, GE0119 shows one pi-sigma and two pi-sulfur bond with MET109; two pi-alkyl bonds with VAL265; three pi-pi stacked and one pi-alkyl bond with TRP243; one conventional hydrogen bond and one pi-alkyl bond with HIS261; one pi-alkyl bond with VAL88; one pi-pi stacked bond with TRP179; one pi-alkyl bond with CYS180 and one pi-sulfur bond with CYS95. As shown in FIG. 3F, GE1109 shows two pi-sigma and one pi-sulfur bonds with MET109; two pi-alkyl bonds with VAL265; three pi-pi stacked bonds with TRP243; one conventional hydrogen bond with HIS261; one pi-alkyl bond with VAL88; one pi-alkyl bond with CYS180 and one conventional hydrogen bond with CYS95. As shown in FIG. 3G, GE1110 shows one pi-sigma, one pi-sulfur and one pi-alkyl bond with MET109; three pi-alkyl bonds with VAL265; two pi-pi stacked and one carbon-hydrogen bond with TRP243; one pi-pi stacked with TRP179; one conventional hydrogen bond and one pi-pi T shaped bond with HIS261; one conventional hydrogen bond and two pi-alkyl bonds with VAL88; two pi-alkyl bond and one conventional hydrogen bond with CYS180; one conventional hydrogen bond with SER268; one pi-alkyl bond with TYR113 and one pi-alkyl bond with PHE239. As shown in FIG. 3H, GE1111 shows one pi-sigma, one pi-sulfur and one pi-alkyl bond with MET109; three pi-alkyl bonds with VAL265; two pi-pi stacked and one carbon hydrogen bond with TRP243; one pi-pi stacked bond with TRP179; one conventional hydrogen bond, one pi-pi T shaped bond with HIS261; one conventional hydrogen bond with VAL88; one pi-alkyl bond with CYS180; one conventional hydrogen bond with SER103; one pi-alkyl bond with TYR113 and pi-alkyl bond with PHE239.

TABLE 1

Binding affinity and interactive amino acid residues of exemplary small compounds and genistein against MRGPRX2.

| Compound ID | Binding affinity (kcal/mol) | Interactive amino acid residues* |
|---|---|---|
| GE0117 | −12.1 | Asn85[a], His261[a], Gly169[a], Met109[b, f], Trp243[c, e], Val265[e], Phe170[e], Cys180[e] |
| GE0118 | −11.5 | Cys180[a, e], His261[a, e], Met109[b, f], Trp179[c], Trp243[c, d, e], Val265[e], Val88[e] |
| GE0119 | −12.0 | His261[a, e], Met109[b, f], Trp179[c], Trp243[c, e] Val265[e], Cys180[e], Val88[e], Cys95[f], |
| GE1109 | −10.9 | His261[a], Cys95[a], Met109[b, f], Trp243[c, e], Val265[e], Val88[e], Cys180[e] |
| GE1110 | −11.5 | Cys180[a, e], His261[a, e], Ser268[a], Trp243[a, c, d], Trp179[b], Met109[b, e, f], Val88[e], Val265[e], Tyr113[e], Phe239[e] |
| GE1111 | −12.1 | Trp243[a], His261[a], Met109[b, e, f], Trp179[c], Cys180[e], Val88[e], Tyr113[e], Phe239[e], Val265[e], Ser103[a] |
| genistein | −8.6 | Ser96[a], Ser98[a], His261[a], Cys180[a, e], Trp179[b, c, d], Cys95[e], Val88[e], Cys180[e] |

*Interacting amino acid residues were measured 5Å distance from ligands.
[a]Hydrogen bond,
[b]Π-sigma,
[c]Π-Π stacking,
[d]Π-Π T shaped,
[e]Π-alkyl,
[f]pi-sulfur Drug-Like Properties of Novel Small Compound Antagonists The small compound antagonists meet all of the criteria for Lipinski's Rule of five and shown drug-like molecule properties. According to Lipinski's Rule of Five, an orally bioavailable drug should follow a set of rules (MW≤500; Log $P_{o/w}$≤5; H bond donor≤5; H bond acceptor≤10) and must not violate more than 2 of the rules. All the small compound antagonists have a molecular weight of less than 500 g/mol. The Log P value, hydrogen bond (H) donors, and acceptors are under the given acceptable criteria (Table 2). The results demonstrate the drug-like properties of these small compounds, which can be further developed as a therapeutic drug.

TABLE 2

Physical characterization of novel small compound antagonists' drug-likeness properties

| | GE0117 | GE0118 | GE0119 | GE1109 | GE1110 | GE1111 |
|---|---|---|---|---|---|---|
| M.W. (g/mol) | 453.45 | 453.44 | 453.45 | 422.43 | 466.48 | 466.48 |
| $LogP_{o/w}$ (MLOGP) | 3.72 | 4.3 | 3.72 | 3.28 | 3.74 | 3.15 |
| Rotatable bonds | 5 | 5 | 5 | 5 | 6 | 6 |
| H-bond donors | 2 | 0 | 2 | 2 | 1 | 3 |
| H-bond acceptors | 5 | 6 | 5 | 4 | 6 | 5 |

Synthesis and Characterization of Novel Small Compound Antagonists

All six small compound antagonists were investigated for their structural similarity and synthesis procedure via PubChem and SciFinder compound library. No structurally similar compound or similar synthetic method for these small compound antagonists were identified.

Example 2. The Compounds Show In Vitro MRGPRX2 Inhibitory Activity

Materials and Methods

Compound Preparation

All the small compounds were dissolved in dimethyl sulfoxide (DMSO) (Sigma, St. Louis, MO, USA) and diluted to the desired concentration in the buffer, media, or saline. The final DMSO concentration was ≤0.1% v/v for in-vitro cell culture experiments. For in-vivo experiments, the DMSO stock of compound was diluted with normal saline and the DMSO saline was used as vehicle control.

Cell Lines

Human mast cell Laboratory Allergic Disease 2 (LAD-2) cell line was grown and maintained in StemPro-34 medium supplemented with 10 ml/L StemPro nutritional supplements, penicillin (1:100), streptomycin (1:100), 2 mmol/L glutamine and 100 ng/ml human stem cell factor and incubated at 37° C. in 5% $CO_2$ incubator. Hemi-depletions of media and cell proliferation examination was performed every five days. HTLA cell line (HEK293 cell line which stably expressing a tTA-dependent luciferase reporter and a β-arrestin2-TEV fusion gene) were grown and maintained in Dulbecco's Modified Eagle Medium (DMEM) supplemented with 10% Fetal Bovine Serum (FBS), 2 μg/ml puromycin and 100 μg/ml hygromycin B and incubated in a humidified atmosphere at 37° C. in 5% $CO_2$ incubator.

β-Hexosaminidase MCs Degranulation Assay

Human LAD-2 mast cells were seeded at $2\times10^4$ cells/well/80 μL in a 96-well plate. A 10× stock of antagonist were prepared in HEPES buffer (HEPES (10 mM), NaCl (137 mM), KCl (2.7 mM), $Na_2HPO_4\cdot7H_2O$ (0.4 mM), glucose (5.6 mM), $CaCl_2\cdot2H_2O$ (1.8 mM), $MgSO_4\cdot7H_2O$ (1.3 mM), bovine serum albumin (0.04%), pH 7.4). The antagonist (10 μL of 10× concentration) or buffer was added to cells and incubated at 37° C. incubators without $CO_2$ for 30 min. Further, a graded concentration of agonist (10 μL of 10× concentration) or buffer was added to each well and cells were incubated at 37° C. without $CO_2$ for an additional 30 min. The plate was spun at 450×g for 5 minutes at room temperature, and 50 μL of supernatant was aliquoted to a new 96 well plate. The cells were lysed with 100 μL of 0.1% Triton X-100, and 50 μL of lysate was aliquoted to another 96 well plates. A 1.3 mg/ml solution of the substrate PNAG (4-Nitrophenyl N-acetyl-β-D-glucosaminide) was prepared in 0.1 M citric acid/sodium citrate buffer (pH 4.5, 24.087 g/L Sodium Citrate dihydrate, and 3.471 g/L Citric Acid). 50 μL of PNAG was added to each well of supernatant and lysate, and cells were incubated for 90 min at 37° C. (without $CO_2$). The reaction was stopped by adding 50 μL of 0.4 M Glycine buffer. The extent of yellow color was measured at 405 nm using Victor 4× plate reader (PerkinElmer), and percentage MCs degranulation (β-hexosaminidase release) was calculated by using the formula; % MCs degranulation:

$$\frac{OD \text{ at } 405 \text{ nm of the supernatant} \times 100\%}{(OD \text{ at } 405 \text{ nm of the supernatant} + OD \text{ at } 405 \text{ nm of the lysate})}.$$

MRGPRX2 Activation Assay (PRESTO-Tango Assay)

The activation of MRGPRX2 was measured by PRESTO-tango assay, according to Kroeze, Wesley K et al., with modification. HTLA cells were cultured in DMEM supplemented with 10% FBS, 2 μg/ml puromycin and 100 μg/ml hygromycin B in a humidified atmosphere at 37° C. in 5% $CO_2$ incubator. On day 1 of the experiment, HTLA cells were seeded at $1\times10^6$ cells per 100 mm cell culture dish for transfection. On the following day (day 2), HTLA cells were transfected with Tango MRGPRX2 DNA using the Lipofectamine transfection reagent (Thermo Fischer Scientific). On day 3, Tango MRGPRX2 transfected cells were transferred into 96-well white clear-bottom cell culture plates at a density of $2\times10^4$ cells/well/80 μL (PerkinElmer Life Science). On day 4, the antagonist (10 μL of 10× concentration) or buffer (10 μL of 20 mM HEPES in 1×HBSS at pH 7.4), was added to each well, and cells were incubated at 37° C. in 5% $CO_2$ incubator for 4 hours. After 4 hours of incubation, the graded concentration of agonist (10 μL of 10× stock) or buffer was added to each well and cells were incubated for another 14 hours at 37° C. in 5% $CO_2$ incubator. On day 5, after removing the complete media from each well, Bright-Glo solution (Promega) (30 μl/well) was added, and cells were incubated for 5 minutes at room temperature. Luminescence (relative luminescence units (RLU)) was measured in a Victor 4× plate luminescence counter (PerkinElmer) and Graph Pad Prism was used for the data analysis.

Cell Toxicity Assay

The cell cytotoxicity was determined via trypan blue exclusion assay and MTT assay using a standard protocol with modifications. Human LAD-2 MCs and HTLA cells were seeded into 96-well plates ($2.2\times10^4$ cells/well/90 μL) and allowed to adhere or equilibrate for 24 hours at 37° C. in a 5% $CO_2$ incubator. After 24 hours of incubation, the cells were treated with graded concentrations (10 μl of 10× of 0-100 μM) of the antagonist for 24 hours at 37° C. in a 5% $CO_2$ incubator. In trypan blue staining assay, after 24 hours of incubation, the cells were harvested, stained with trypan blue, and live and dead cells were counted using LUNA automated cell counter (logos biosystem). For MTT assay, 20 μl volume of MTT solution (5 mg/mL in phosphate buffer solution) was added to each well, and cells were incubated for 4 hours at 37° C. in 5% $CO_2$ incubator. For LAD-2 cells, the plate was centrifuged at 500 g for 5 minutes, and the media was aspirated, while for HTLA cells, the medium was aspirated directly. The formed formazan crystals were solubilized by adding 150 μL of MTT solvent (4 mM HCL+0.1% NP-40 in isopropanol) each well and incubated in a 4° C. shaker for 15 minutes. Finally, the intensity of the dissolved formazan crystals (purple color) was quantified using the Victor 4× plate reader (PerkinElmer) at 540 nm. The % cell viability was calculated by comparing the OD of drug treatment with control cells and plotted in Graph Pad Prism software. The controls cells were LAD-2 & HTLA) treated with vehicle (DMSO) instead of compounds.

Intracellular $Ca^{2+}$ Flux Assay

The intracellular $Ca^{2+}$ flux was measured in human LAD-2 MCs by using the Fluo-4 NW calcium assay kit and the protocol according to the manufacturer (Molecular Probe, Invitrogen, USA). Briefly, LAD-2 cells were plated in a 96-well black well plate (SPL Life Sciences) at a density of $1\times10^5$ cells/well/40 μL in assay buffer and incubated for 1 h at 37° C. incubators. After 1 h, 40 μL of the 2× dye loading solution and antagonist or buffer was added to the cells (10 μL of 10× stock). The cells were incubated for 30 minutes at 37° C. in 5% $CO_2$ incubator followed by an additional 30-minute incubation. After one hour of incubation, a graded concentration of agonist or buffer was added to the cells (10 μL of 10× stock). The fluorescence was measured at an excitation wavelength of 494 nm and an emission wavelength of 516 nm using Victor 4× plate reader (PerkinElmer) for 150 seconds. The ΔF was calculated by subtracting the maximum wavelength (after adding agonist C48/80) from minimum fluorescence (before adding agonist) and plotted by using Graph Pad Prism.

Monocyte Chemoattractant Protein-1 (MCP-1) and Prostaglandin D-2 (PGD2) Measurement MCP-1 and PGD2 were measured from human LAD2 MCs via individual ELISA kits. Briefly, MCs were seeded at a density of $1.5\times10^5$ cells/80 μL/well in a 96 well plate in complete Stem-Pro 34 media. The MCs were equilibrated for 1-2 hours and treated with 10 μL of 10× of different concentrations of small compound antagonist and incubated for 30 minutes at 37° C. in 5% $CO_2$ incubator. For measurement of MCP-1, after 30 minutes, cells were treated with agonist 100 ng/ml C48/80 (10 μL of 10× stock) and incubated for 6 hours at 37° C. in 5% $CO_2$ incubator. The cells were centrifuged to collect the supernatant and stored at −80° C. until analyzed. For PGD2 measurement, after 1 hour of antagonist treatment, cells were treated with agonist 30 μg/ml C48/80 (10 μL of 10× stock) and incubated for 24 hours at 37° C. in 5% $CO_2$ incubator. After 24 hours, cells were centrifuged to discard the media and lysed with 0.1M potassium phosphate via sonication. The supernatant of cell lysate was collected and stored at −80° C. until analyzed. MCP-1 (Abcam, Cambridge, UK) and PGD2 (Cayman Chemicals, MI, USA) were quantified by ELISA according to manufacturer instruction.

Results

Figure 4A:
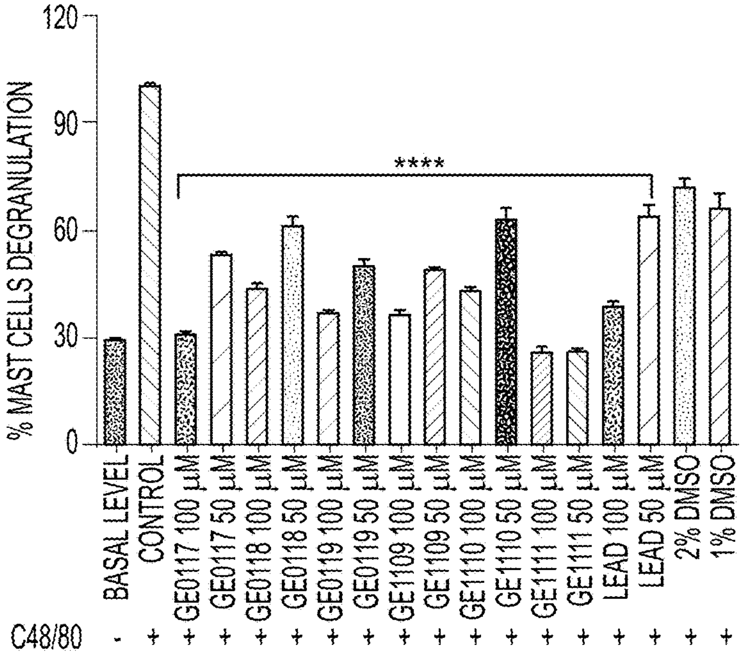
FIG. 4A is a bar graph showing the antagonistic effect of the small compound antagonists on MCs degranulation.
Figure 4B:
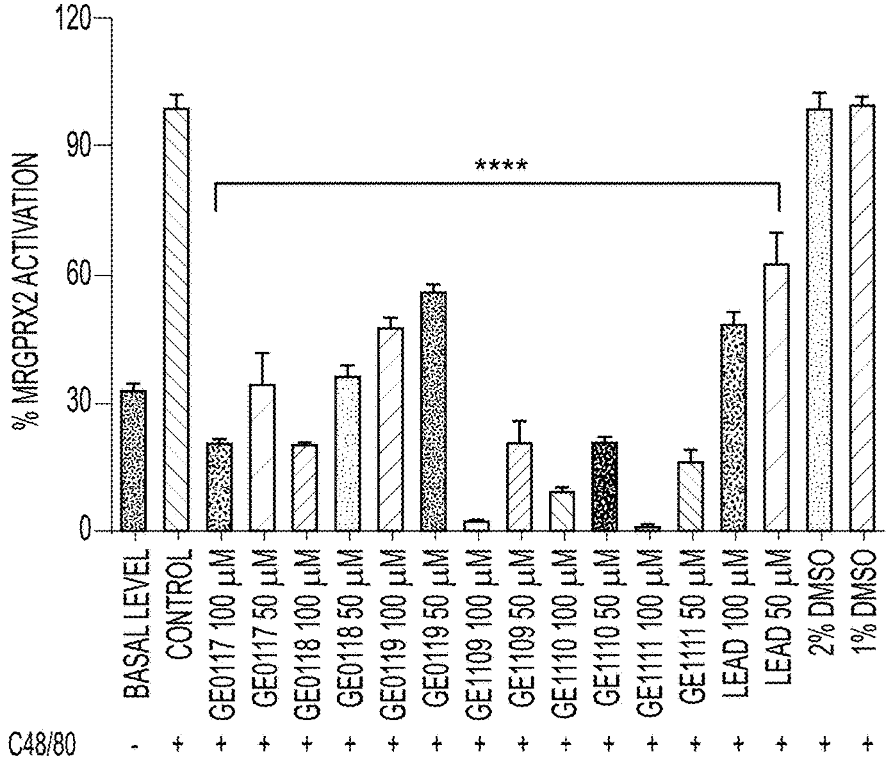
FIG. 4B is a bar graph showing the antagonistic effect of the small compound antagonists on MRGPRX2 activation.
Figure 4C:
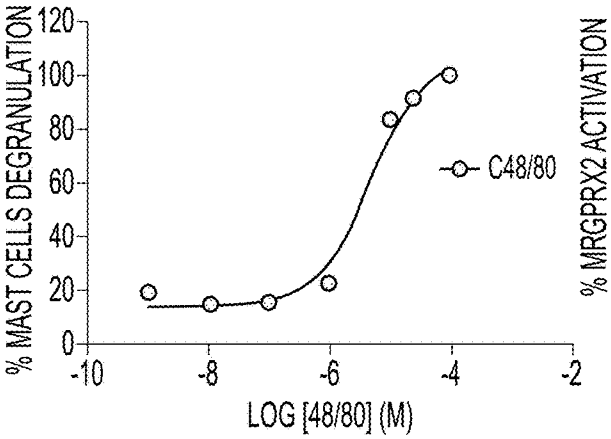
FIG. 4C is a graph showing the dose-response curve of C48/80 via MCs degranulation.
Figure 4D:
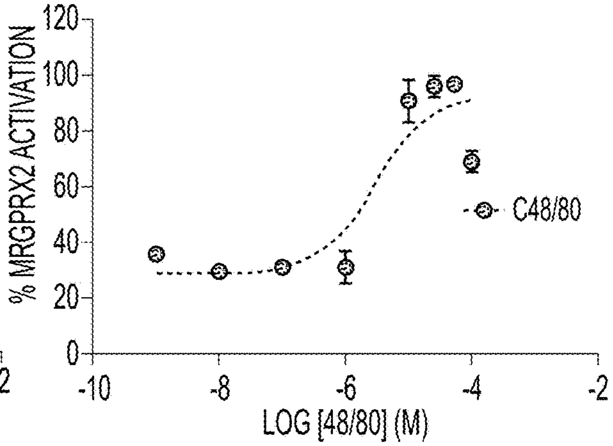
FIG. 4D is a graph showing the dose-response curve of C48/80 via MRGPRX2 activation assay. The $EC_{50}$ of C48/80 is 4.61 μM and 2.85 μM in MCs degranulation and MRGPRX2 activation assay, respectively. The $EC_{90}$ of C48/80 is −10 μM.
Figure 4E:
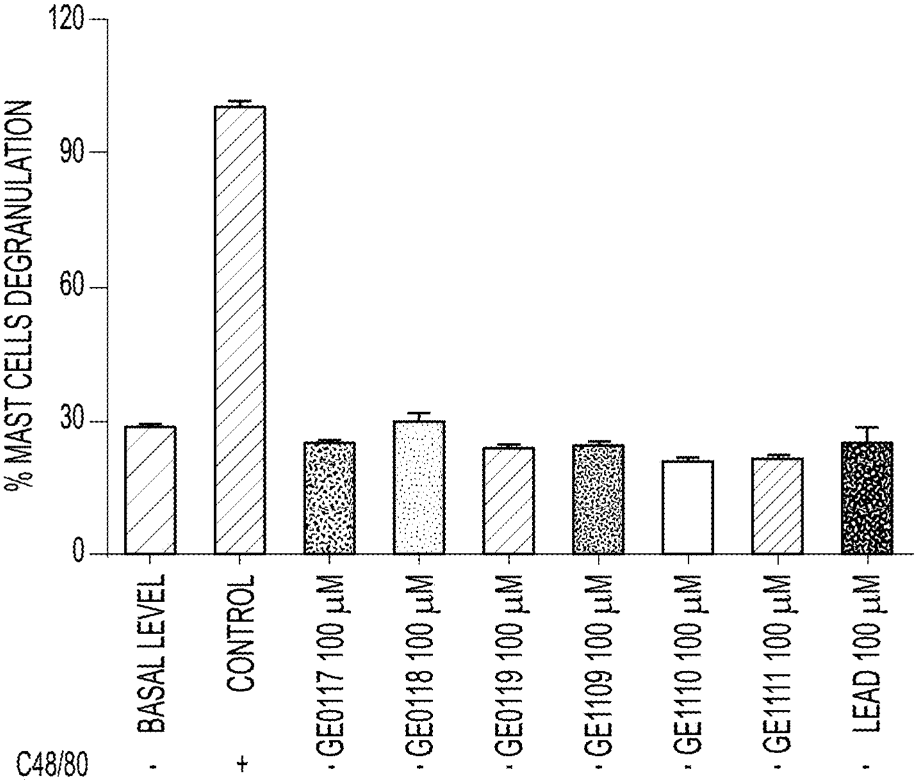
FIG. 4E is a bar graph showing MCs degranulation in the absence of C48/80.
Figure 4F:
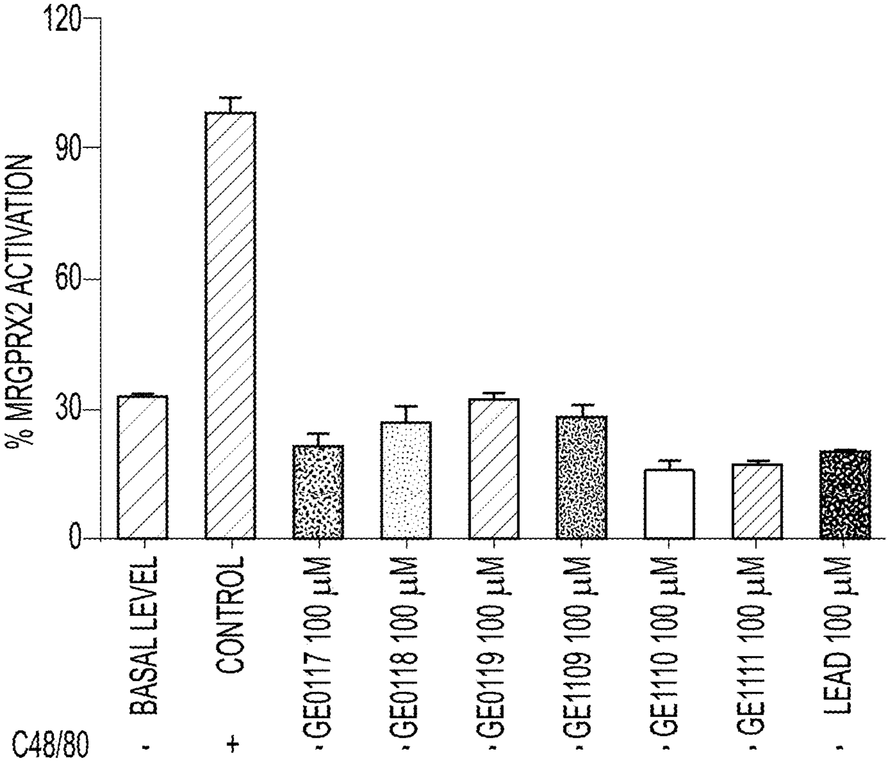
FIG. 4F is a bar graph showing MRGPRX2 activation assay in the absence of C48/80. The data are presented as the mean±SEM of three independent experiments, ****P<0.0001 compared to control (C48/80).
Figure 5A:
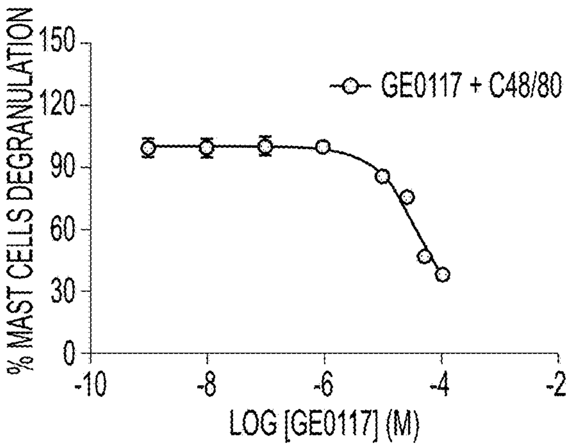
FIG. 5A-5G are graphs showing the antagonistic activity and $IC_{50}$ concentration of the small compound antagonists, where a dose response curve (DRC) was performed via MCs degranulation assay. Human LAD-2 MCs were treated with a graded concentration of the small compound antagonists, GE0117 (FIG. 5A) GE0118 (FIG. 5B), GE0119 (FIG. 5C), GE1109 (FIG. 5D), GE1110 (FIG. 5E), GE1111 (FIG. 5F), and genistein (also referred herein as "Lead") (FIG. 5G), followed by treatment with $EC_{90}$ concentration (10 μM) of C48/80.
Figure 5B:
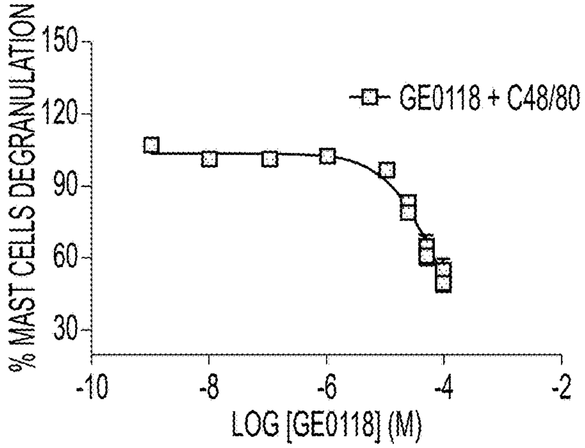
Figure 5C:
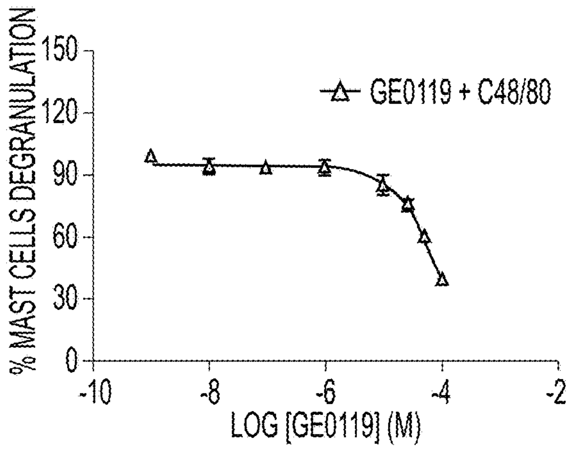
Figure 5D:
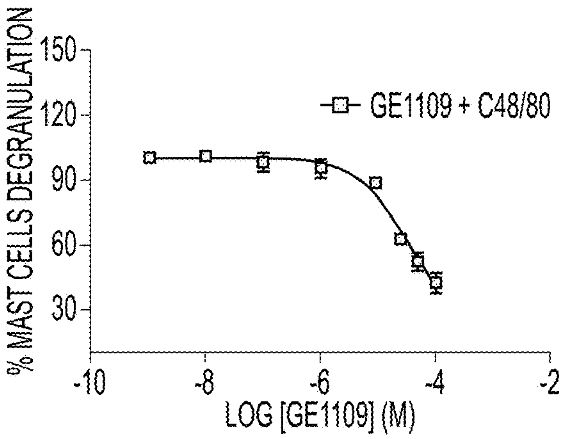
Figure 5E:
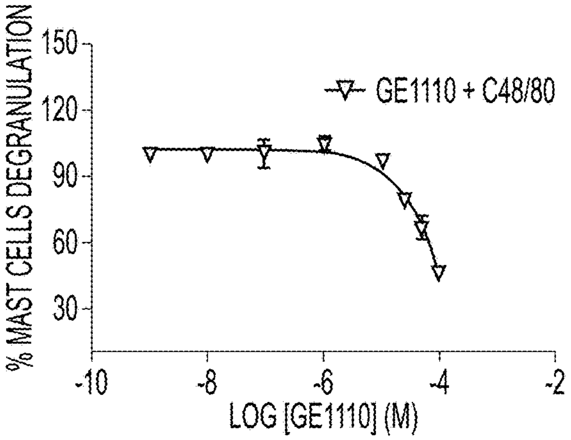
Figure 5F:
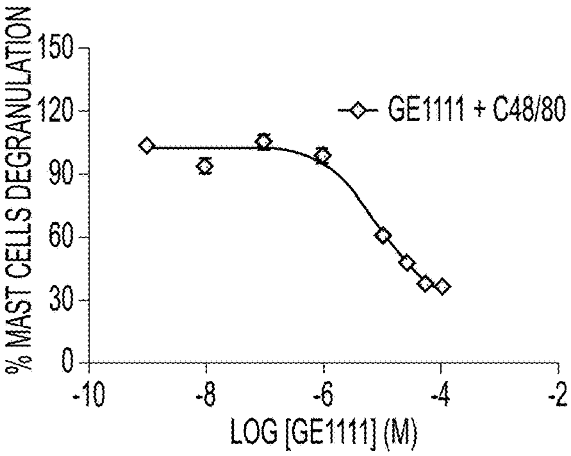
Figure 5G:
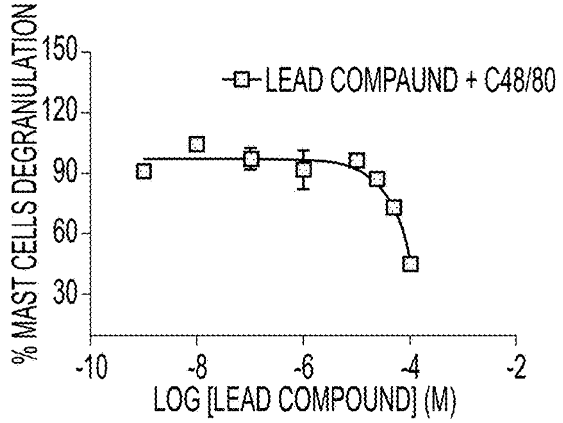
Figure 5H:
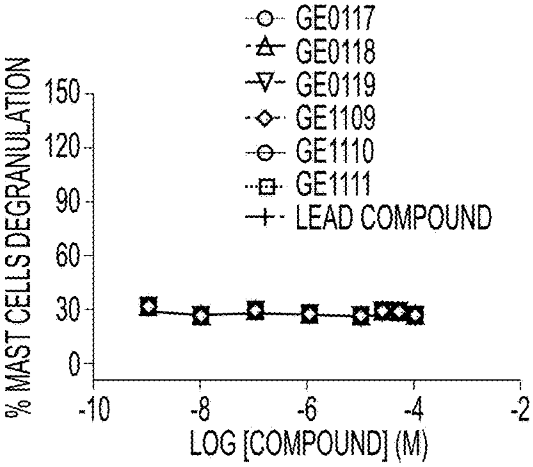
FIG. 5H is a graph showing Human LAD-2 MCs treated with a graded concentration of the small compound antagonists and genistein only. Each data represents the mean±SEM of four-six independent experiments.
Figure 6A:
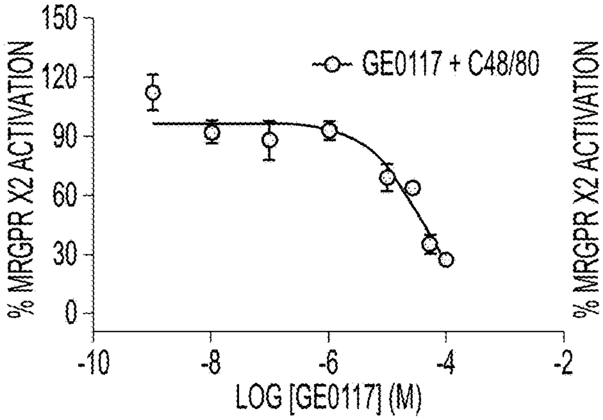
FIG. 6A-6G are graphs showing the $IC_{50}$ of the small compound antagonists via MRGPRX2 Tango assay. A DRC was performed for $IC_{50}$ evaluation. MRGPRX2-Tango transfected HTLA cells were treated with a graded concentration of the small compound antagonists followed by $EC_{90}$ concentration (10 μM) of C48/80, GE0117 (FIG. 6A), GE0118 (FIG. 6B), GE0119 (FIG. 6C), GE1109 (FIG. 6D), GE1110 (FIG. 6E), GE1111 (FIG. 6F), and genistein (FIG. 6G).
Figure 6B:
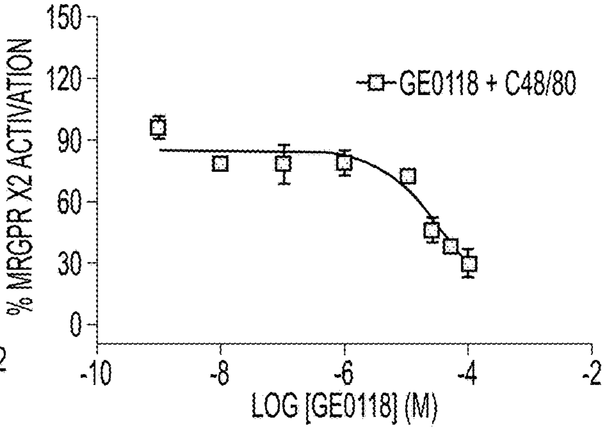
Figure 6C:
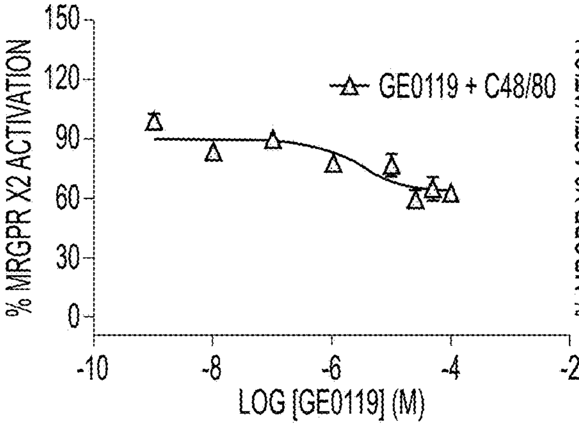
Figure 6D:
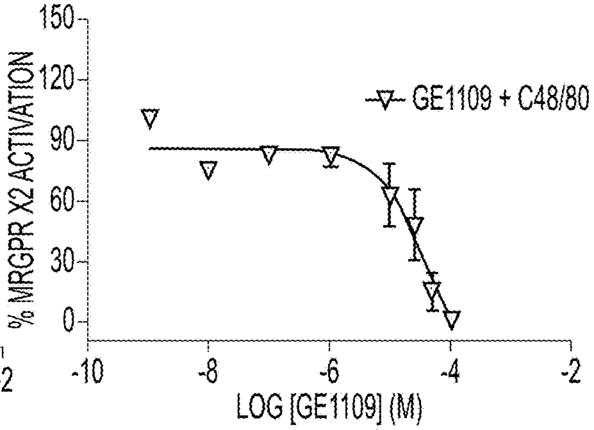
Figure 6E:
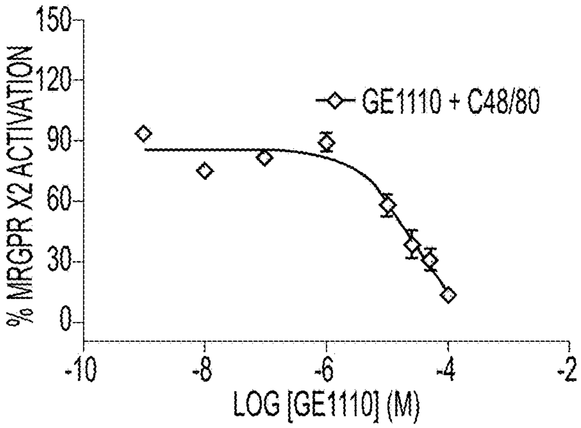
Figure 6F:
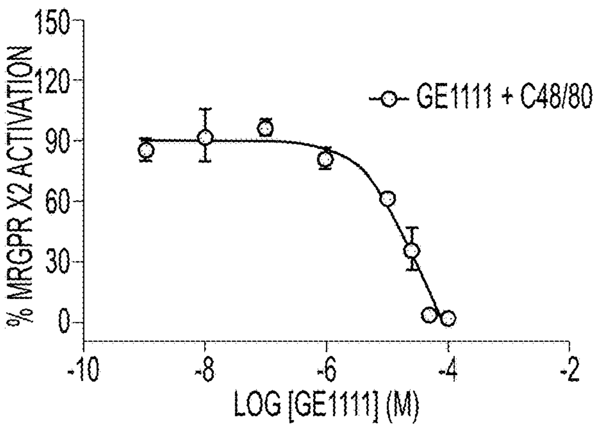
Figure 6G:
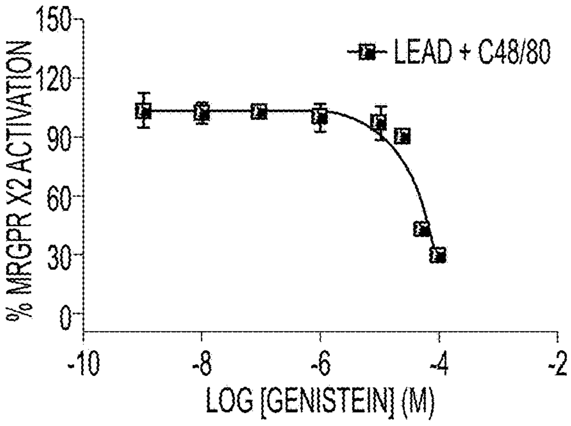
Figure 6H:
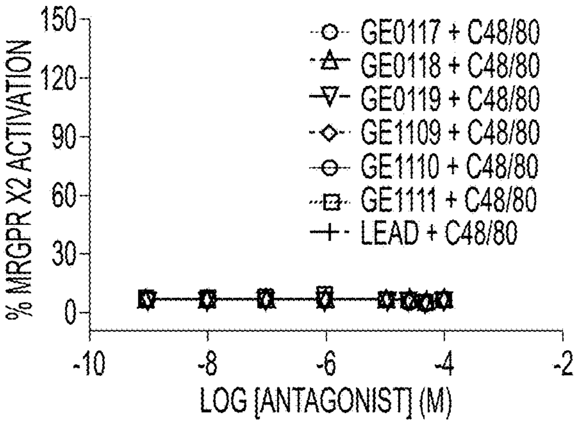
FIG. 6H is a graph showing Mock transfected HTLA cells (Non-MRGPRX2 plasmid) treated with a graded concentration of the small compound antagonists followed by $EC_{90}$ concentration (10 μM) of C48/80. Each data represents the mean±SEM of four-six independent experiments.

Primary Screening of Small Compound Antagonists Via In-Vitro MCs Degranulation and MRGPRX2 Activation Assay MCs degranulation is an event in releasing preformed/de novo synthesized mediators and developing the edema and lesions in allergy. MCs granules store a potent cocktail of preformed inflammatory mediators, such as histamine, heparin, serotonin, tryptase, and chymase. Moreover, several de-novo synthesized mediators such as prostaglandins derived from the precursor molecule arachidonic acid. To evaluate the antagonistic activity of synthesized novel small compound antagonists, MCs degranulation functional assay (% β-Hexosaminidase release) was performed on human MCs (FIG. 4A). Also, to evaluate the MRGPRX2 specific activity, MRGPRX2-Tango-β arrestin recruitment assay was performed on MRGPRX2-Tango transfected HTLA cells (FIG. 4B). For the primary screening, 50 μM and 100 μM concentrations of antagonists and vehicle control (DMSO 1% & 2%) were used. The MRGPRX2 agonist C48/80 was used at a concentration of 10 μM, which is based on the 90% maximal response effective concentration (~EC90) of C48/80 in both MCs degranulation and MRGPRX2-Tango activation assay (FIGS. 4C and 4D). The small compound antagonists have demonstrated significant inhibition of MCs degranulation (FIG. 4A) as well as MRGPRX2 activation at both concentrations (****$P<0.001$) (FIG. 4B). There was no significant difference in the C48/80 induced MCs degranulation and MRGPRX2 activation activity by the DMSO vehicle, demonstrating no DMOS vehicle activity in these bioassays. The primary screening results show the antagonizing potential of small compound antagonists compared to genistein. Additionally, to check the small compound antagonists' intrinsic agonistic potential, MCs degranulation and MRGPRX2 activation assay were performed without treating cells with agonist C48/80. There was no significant change in the MCs degranulation and MRGPRX2 activation, demonstrating no intrinsic activity of the small compound antagonists (FIGS. 4E and 4F).

Evaluation of Half-Maximal Inhibitory Concentration ($IC_{50}$) of Small Compound Antagonists Although several findings highlighted the role of the MCs-MRGPRX2 activation in the etiology of pseudo allergic reaction, there is no specific antagonist available that can be used in the prevention or treatment of pseudo allergic reactions. Several natural compounds have recently been tested for MRGPRX2 antagonistic activity; however, low potency and less efficacy are the primary concern for drug development. A graded concentration (0-100 μM) was used to assess $IC_{50}$ of the synthesized small compound antagonists (GE0117, GE0118, GE0119, GE1109, GE1110, and GE1111) and a dose-response curve via MCs degranulation (FIGS. 5A-5H) and MRGPRX2 activation assays (FIGS. 6A-6H) were obtained. Genistein was used as a positive reference standard. The small compound antagonists did not show any cytotoxicity up to 100 μM concentration to human LAD-2 MCs and HTLA cells determined by cell viability (using trypan blue, data not shown) and MTT assays (data not shown).

In both assays, the antagonists show a concentration-dependent inhibition of MCs degranulation and MRGPRX2 activation with an $IC_{50}$ in the micromolar concentration range (Table 3). Notably, in the functional MCs degranulation assay, GE1109 ($IC_{50}$; 9.87 μM) and GE1111 ($IC_{50}$; 4.70 μM) have shown significant inhibitory activity as compared to genistein ($IC_{50}$; 30.32 μM). However, comparatively, the antagonist GE0119 ($IC_{50}$; 25.49 μM) and GE1110 ($IC_{50}$; 23.42 μM) have shown a comparable inhibitory activity in MCs degranulation to genistein. There was no change in the basal MCs degranulation level by a graded concentration of small compound antagonists which demonstrates no intrinsic agonistic activity. In the receptor activation assay, GE1109 and GE1111 have shown an $IC_{50}$ of 7.14 μM and 9.42 μM, respectively, while the $IC_{50}$ of the genistein was 31.70 μM. Further, to verify the MRGPRX2 dependent effect of a fixed concentration of C48/80 and small compound antagonists, mock-transfected HTLA cells were treated with C48/80 and graded concentration of antagonist. There was no luminescence response recorded in these cells, which demonstrates the MRGPRX2 dependent activity of the small compound antagonists. GE0117, GE1109 and GE1111 have shown potent antagonizing activity in both MCs degranulation and MRGPRX2 activation assays.

TABLE 3

$IC_{50}$ concentration of novel small compound antagonists calculated by human MCs degranulation and MRGPRX2 activation assay

| Compounds ID | $IC_{50}$ concentration (MCs degranulation assay) | $IC_{50}$ concentration (MRGPRX2 activation assay) |
|---|---|---|
| GE0117 | 20.76 μM | 9.79 μM |
| GE0118 | 18.25 μM | 8.91 μM |
| GE0119 | 25.49 μM | 20.13 μM |
| GE1109 | 9.87 μM | 7.14 μM |
| GE1110 | 23.42 μM | 8.93 μM |
| GE1111 | 4.70 μM | 9.42 μM |
| genistein | 30.32 μM | 31.70 μM |

Figure 7:
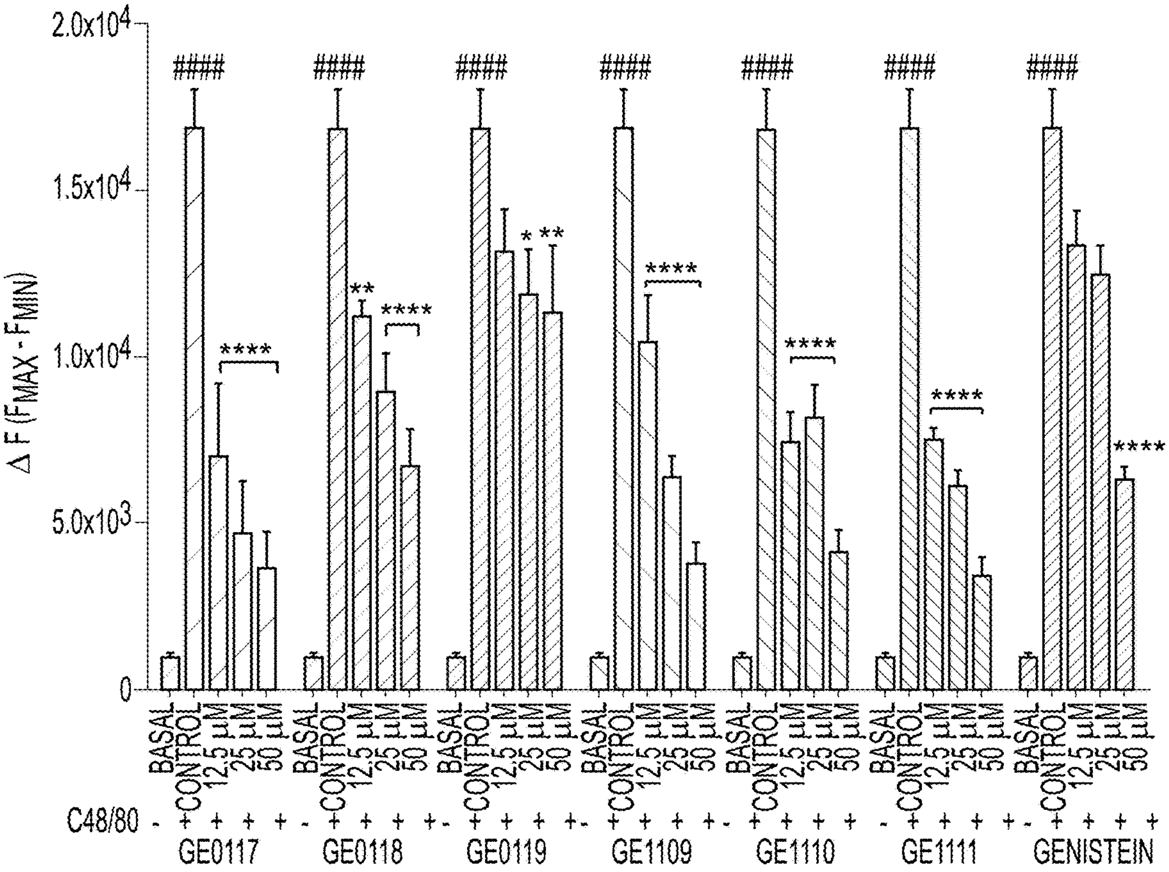
FIG. 7 is a bar graph showing the effect of the small compound antagonists on MCs calcium influx response. Small compound antagonists GE0117, GE0118, GE0119, GE1109, GE1110, GE1111, and genistein show a concentration-dependent decrease in C48/80 ($EC_{90}$ concentration) induced calcium influx. The data are presented as the mean±SEM of five-six independent experiments, $^{####}$P<0.0001 as compared to basal calcium influx, *P<0.05, P<0.01, *P<0.001, ****P<0.0001 as compared to control (C48/80).

GE0117, GE0118, GE0119, GE1109, GE1110, and GE1111 show a significant concentration-dependent reduction in $Ca^{2+}$ flux (FIG. 7). Among all, GE0117, GE1109, GE1110, and GE1111 have shown a higher efficacy at all three concentrations (12.5 μM, 25 μM, and 50 μM, **P<0.0001). Genistein was used as a reference standard and shows a significant (P<0.001) $Ca^{2+}$ flux reduction at 50 μM concentration only. The $Ca^{2+}$ flux assay results demonstrate the potent antagonistic activity against the early phase of MCs activation. As store-operated $Ca^{2+}$ entry (SOCE) via the calcium sensor, stromal interaction molecule 1 (STIM1) was reported to involve in MRGPRX2 activation; without being bound to any theories, the antagonists may exhibit its effect via modulating the SOCE-STIM1 activity in MCs.

Figure 8A:
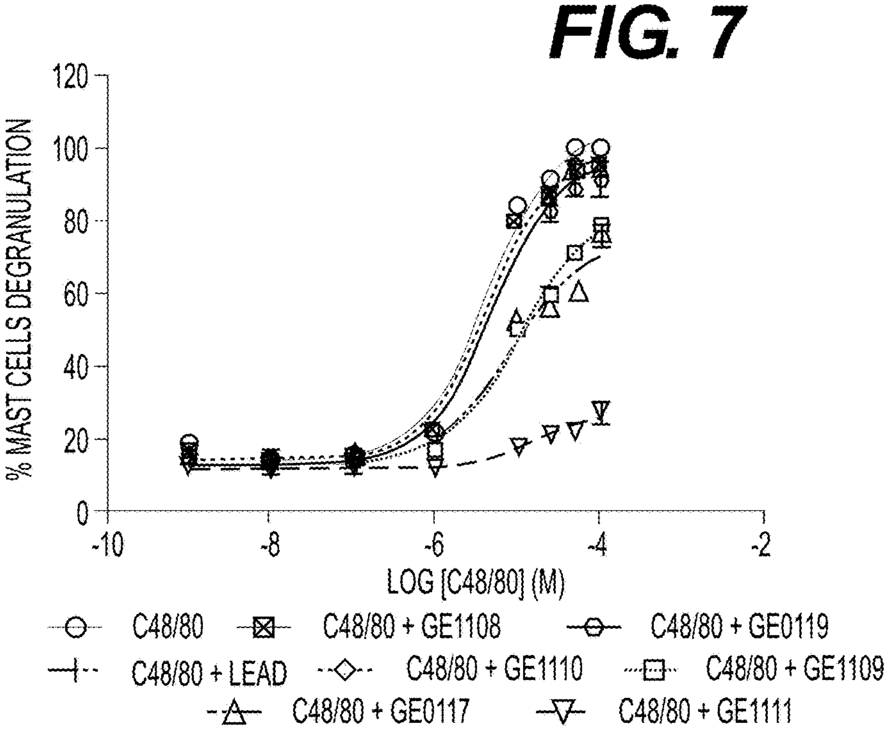
FIGS. 8A-8B are graphs showing the effect of the small compound antagonists on C48/80's $EC_{50}$ and Emax via MCs degranulation assay (FIG. 8A) and MRGPRX2 activation assay (FIG. 8B). The concentration of all of the small compound antagonists and genistein was 10 μM.
Figure 8B:
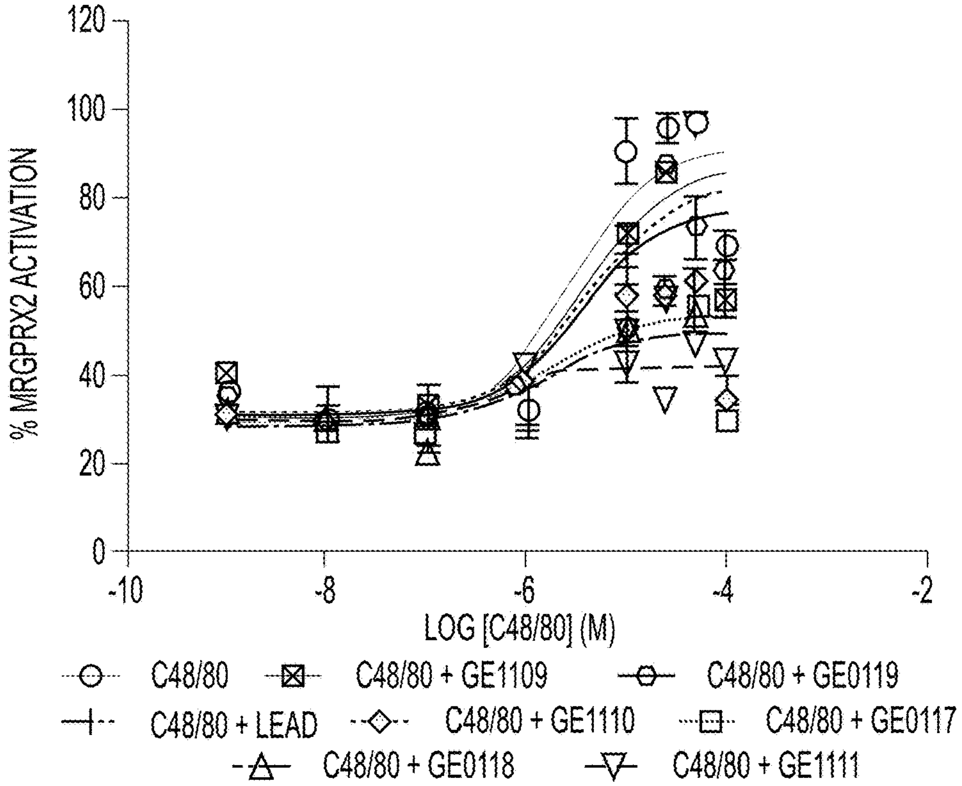

Evaluation of the Effect of Small Compound Antagonists on the Dose-Response Curve (EC50 & $E_{max}$) of Compound 48/80 Via MCs Degranulation Assay and MRGPRX2 Activation Assay C48/80 activates MCs via MRGPRX2 in a dose-dependent fashion; a dose-dependent activation of MCs via MCs degranulation assay and MRGPRX2 activation assay was measured. To compare all the small compound antagonist's efficacy, human LAD2 MCs cells and MRGPRX2 transfected HTLA cells were treated with a fixed concentration (10 μM) of antagonists followed by a graded concentration of agonist C48/80 (FIGS. 8A and 8B). Antagonist GE0117, GE1109 and GE1111 significantly antagonize the C48/80 induced MCs degranulation and MRGPRX2 activation, as shown by the EC50 and Emax change compared to genistein (Table 4).

TABLE 4

Changes in the $EC_{50}$ and $E_{max}$ of Dose-response curve (DRC) of C48/80 by the small compound antagonists calculated via human MCs degranulation and MRGPRX2 activation assays

| In-vitro assay | | Buffer | GE0117 | GE0118 | GE0119 | GE1109 | GE1110 | GE1111 | genistein |
|---|---|---|---|---|---|---|---|---|---|
| MCs degranulation | EC50 (μM) | 4.61 | 8.97 | 4.82 | 4.71 | 11.38 | 5.52 | 20.85 | 4.61 |
| | % Decrease in $E_{max}$ | | 29.56% | 5.98% | 7.44% | 20.93% | 4.30% | 72.75% | 8.55% |
| MRGPRX2 activation | EC50 (μM) | 2.85 | 17.2 | 13.83 | 3.13 | 3.93 | 19.92 | 27.68 | 3.83 |
| | % Decrease in $E_{max}$ | | 46.61% | 46.03% | 15.68% | 9.95% | 42.21% | 54.43% | 5.56% |

% Decrease in $E_{max}$ = ($E_{max}$ of C48/80 − $E_{max}$ of antagonist treated C48/80)/$E_{max}$ of C48/80*100

Evaluation of the Effect of the Small Compound Antagonists on Intracellular $Ca^{2+}$ Flux MRGPRX2 activation leads to a rapid increase in intracellular $Ca^{2+}$ flux that decays very slowly, and MCs degranulation is preceded by surges of intracellular $Ca^{2+}$ concentrations. This sustained $Ca^{2+}$ flux response induced by MRGPRX2 is unique compared to other GPCRs, which mostly induce a transient $Ca^{2+}$ response that almost immediately returns to baseline due to their rapid desensitization and internalization. To evaluate the effects of the small compound antagonists on the activation of human MC's $Ca^{2+}$ flux, the LAD2 MCs were treated with varying antagonist concentrations, followed by stimulation with C48/80 and $Ca^{2+}$ response measurement. The small compound antagonists by themselves did not induce $Ca^{2+}$ flux (data not shown). C48/80 treatment 20 induced a significant ($^{\#\#\#\#}$P<0.0001) $Ca^{2+}$ flux which was demonstrated by high fluorescence intensity as compared to basal level. Antagonist In the MCs degranulation assay of C48/80, GE0117, GE1109, and GE1111 have increased the $EC_{50}$ of C48/80 from 4.61 μM to 8.97 μM, 11.38 μM, and 20.85 μM, respectively, and decreased the $E_{max}$ of C48/80 by 29.56%, 20.93%, and 72.75, respectively (FIGS. 8A and 8B and Table 4). Moreover, in the receptor activation assay, the antagonists GE0117, GE1109 and GE1111 have shown a better efficacy via changing the C48/80 $EC_{50}$ as well as $E_{max}$ (FIGS. 8A and 8B and Table 4).

Figure 9A:
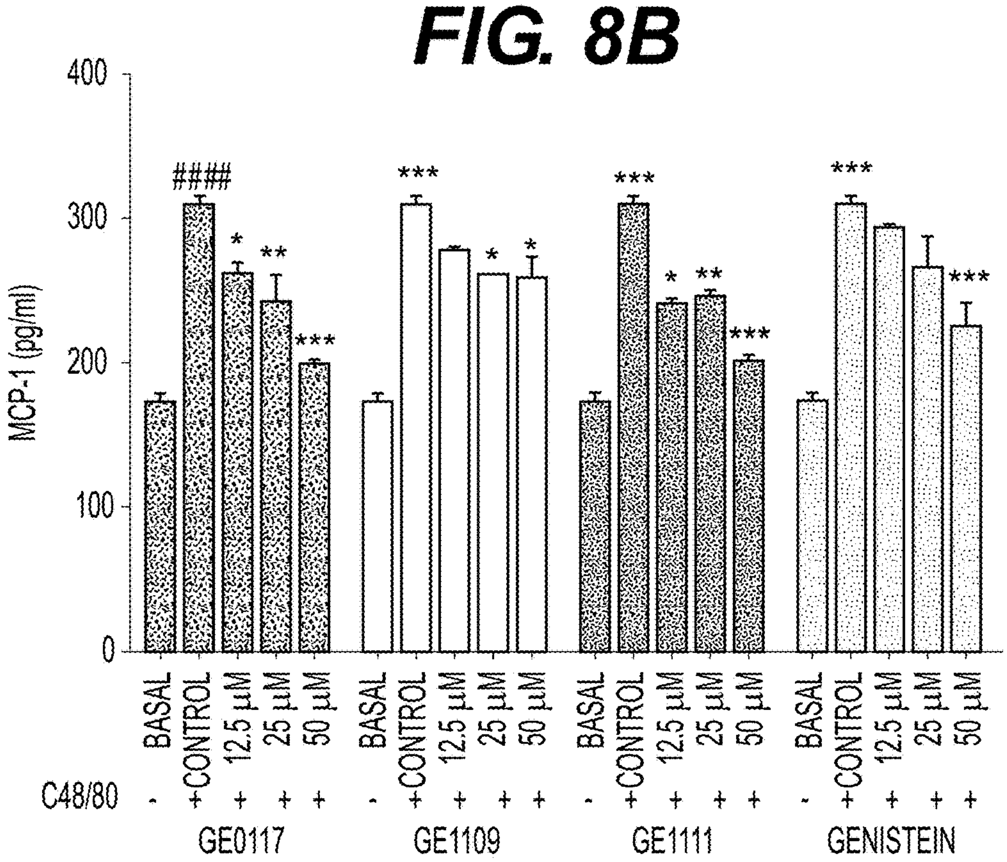
FIGS. 9A-9B are bar graphs showing the effect of the small compound antagonists (GE0117, GE1109, and GE1111) and genistein on C48/80 induced monocyte chemoattractant protein-1 (MCP-1) (FIG. 9A) and Prostaglandin D-2 (PGD-2) release from human MCs (FIG. 9B). The data are presented as the mean±SEM of three independent experiments (N=3), $^{####}$P<0.0001 as compared to the basal level of MCP-1/PGD-2, and *P<0.05, P<0.01, *P<0.001, ****P<0.0001 as compared to control (C48/80).
Figure 9B:
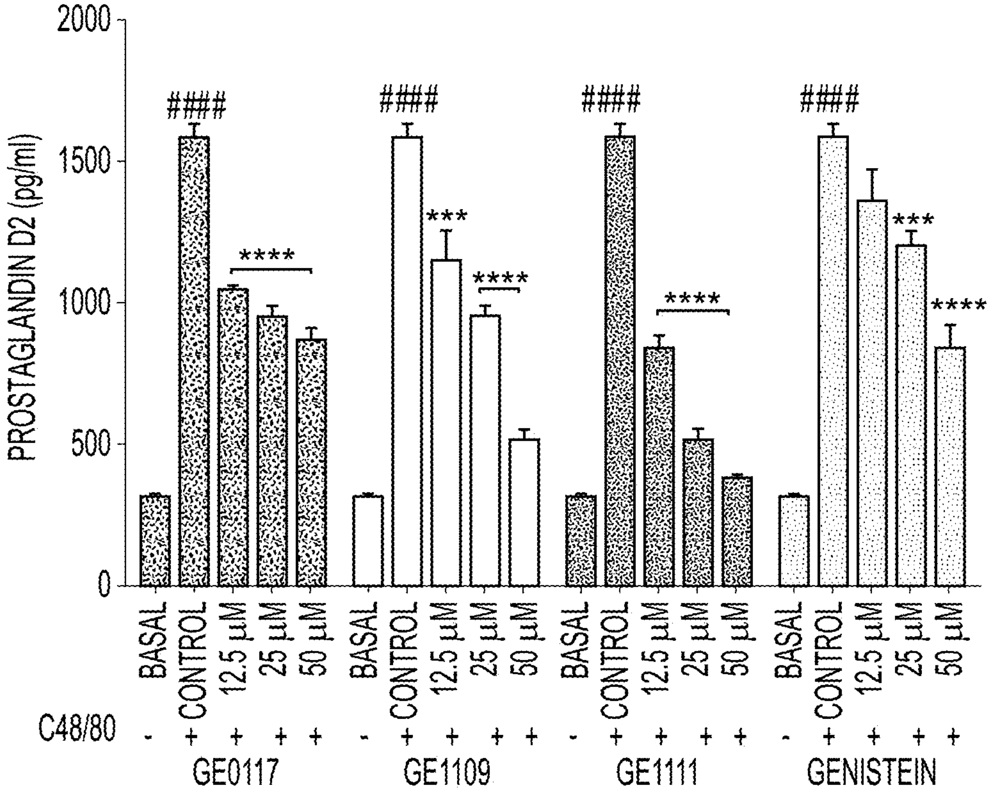

Evaluation of the Effect of the Small Compound Antagonists on Human Monocyte Chemoattractant Protein-1 and Prostaglandin D2 Level MCs activation includes an early phase that includes $Ca^{2+}$ flux and degranulation and a delayed phase that induces production and release of inflammatory chemokine or cytokine. The small compound antagonists (such as GE0117, GE1109, and GE1111) show the antagonizing activity in the early phase of MCs activation (MCs degranulation and $Ca^{2+}$ response). To test whether the potent antagonist GE0117, GE1109, and GE1111 regulate the delayed phase response of MCs activation, the release and production of Monocyte chemoattractant protein-1 (MCP-1) and Prostaglandin D2 (PGD2) were examined. C48/80 activates human LAD2 MCs and increases the production of MCP-1 and PGD2 as compared to basal level ($^{####}$P<0.0001) (FIGS. 9A and 9B). MCP-1 plays a role in recruiting other inflammatory cells such as monocytes, neutrophils, and lymphocytes and inducing chemotaxis through the activation of G-protein-coupled receptors. PGD2 is a significant prostanoid produced mainly by MCs in response to allergic or inflammatory stimuli. PGD2 production begins with the liberation of arachidonic acid from membrane phospholipids by phospholipase A2 in response to inflammatory stimuli. PGD2 plays a role in inducing vasodilatation and increased permeability in several allergic inflammatory diseases. Treatment of MCs with antagonist GE0117 or GE1111 significantly inhibits the release of MCP-1 at all the tested concentrations (12.5 μM *P<0.05, 25 μM, P<0.01 and 50 μM, *P<0.001) while GE1109 shows significant activity only at 25 μM, and 50 μM (*P<0.05) as compared to C48/80 control. The experimental results show the potent activity of the small compound antagonists in inhibiting the release of pre-stored inflammatory mediator (MCP-1) as well as de novo synthesized inflammatory mediator (PGD2) which extends its therapeutic role in the treatment of MCs activated allergic and inflammatory diseases.

Example 3. The Compounds Show Antiallergic Activity in Animal Models

Materials and Methods

In-Vivo Local Anaphylaxis/Pseudo Allergic Activity

Young adult male mice (C57/BL/6N aged 6-8 weeks old, n=6/group) were used to measure the local anaphylaxis activity by measuring Evans blue tissue extravasation in paw and ear tissue. The animal experiments were approved by the Committee on the Use of Live Animals in Teaching and Research (CULATR) (Animal ethical approval number CULATR 5125-19). Mice were anesthetized via intraperitoneal injection of ketamine and xylazine, and paw thickness was measure using a Vernier caliper. The antagonists (GE0117, GE1109, and GE1111) were injected at a dose of 5 mg/kg body weight via intraperitoneal injection followed by a tail vein injection of 50 μL 12.5% Evans blue in saline (irrespective of the bodyweight). After thirty minutes, C48/80 (10 μL of 30 μg/ml) was injected into one paw and ear, while saline was injected into the other paw and ear as a negative control. After fifteen minutes, the paw and ear tissue were photographed, and the paw thicknesses were measured again to calculate % increase in paw thickness. Mice were euthanized by cervical dislocation under anesthesia, and the collected paw and ear tissues were dried at 50° C. for 24 hours and weighed separately. Evans blue was extracted with formamide (500 μL/tissue) by incubating at 50° C. for 24 h. The supernatant was aliquoted into 96-well plates (200 μL/well, duplicate), and OD was measure at 595 nm using a Victor 4× plate reader (PerkinElmer). The paw edema/inflammation was measured as % increase in paw thickness=

$$\frac{(\text{paw thickness after injection} - \text{paw thickness before injection}) \times 100\%}{\text{paw thickness before injection}}$$

and absorbance values were normalized to per gram dried weight of each paw tissue to quantify the Evans blue extravasation.

In-Vivo Systemic Anaphylaxis Activity

Animals (C57/BL/6N aged 6-8 weeks old, n=6-8/group) were transported to the procedure area the day before injections to minimize stress. The antagonists (GE0117, GE1109, or GE1111) or vehicle was injected intraperitoneally, and mice were kept in the cage for 30 minutes. After 30 minutes of saline (negative control), 8 mg/kg of C48/80 was injected intraperitoneally. The volume of intraperitoneal injection was 10 ml/kg body weight as per AAALAC guidelines. The injection site was swabbed with cotton soaked in 70% alcohol, and the mouse was placed in a separate cage as one mouse per cage. Body core temperature was measured before (basal) and after the injections with an IR non-contact thermometer for one hour. Also, mice were monitored for anaphylaxis symptoms/severity and scored from 0-5 for 1 h or until death following C48/80 injection, whichever was first. Briefly, the scoring system was followed as 0, no symptoms; 1, scratching and rubbing around the nose and head; 2, puffiness around the eyes and mouth, diarrhea, pilar erecti, reduced activity, and/or decreased activity with an increased respiratory rate; 3, wheezing, labored respiration, and cyanosis around the mouth and the tail; 4, no activity after prodding or tremor and convulsion; 5, death. The body core temperature and anaphylaxis score were plotted using Graph Pad Prism.

Histological Analysis

The mice were anesthetized with ketamine/xylazine and were injected with antagonists (GE0117, GE1109, and GE1111) at a dose of 5 mg/kg body weight intraperitoneally. After 30 minutes, C48/80 (10 μL of 30 μg/ml) and saline (as negative control) were injected into the ear. Fifteen minutes later, the mice were sacrificed, and the injection site of the ear was excised, washed with PBS, and fixed with 10% buffered formalin for 24 h. After 24 hours, the ear tissue was dehydrated in a graded concentration of ethanol (30%, 50% & 70% ethanol every 24 hours) at 4° C. Further, the tissue was processed in an automated tissue processor (Leica ASP300) and embedded into paraffin using Embedding Centre (Leica EG1150). The paraffin-embedded tissue was sectioned at 5 μM size using a fully automatic Microtome (Leica RM2265). The tissue sections were subjected to H&E staining using an automated slide Stainer (Leica ST5020) using standard staining protocol. After staining, the slides were dried under a fume hood and mounted with DPX. For the MCs detection, the sectioned ear tissue was subjected to Toluidine blue O staining according to the available online protocol (http://www.ihcworld.com/_protocols/special-_stains/toluidine_blue.htm). Images were captured under 10× and 20× magnification using a Nikon Eclipse Ni-U, upright microscope, and Nikon DS-Ri2 microscopic camera (Nikon, Tokyo, Japan).

Statistical Analysis

The data are presented as the mean±SEM of at least three independent experiments otherwise specified. The graphs are plotted using Prism 7.0 software (GraphPad Software Inc.). The data were analyzed using analysis of variance (ANOVA), two-tailed tests, followed by Tukey's multiple comparisons test. A value of p<0.05 was considered to be significant.

Results

Figure 10A:
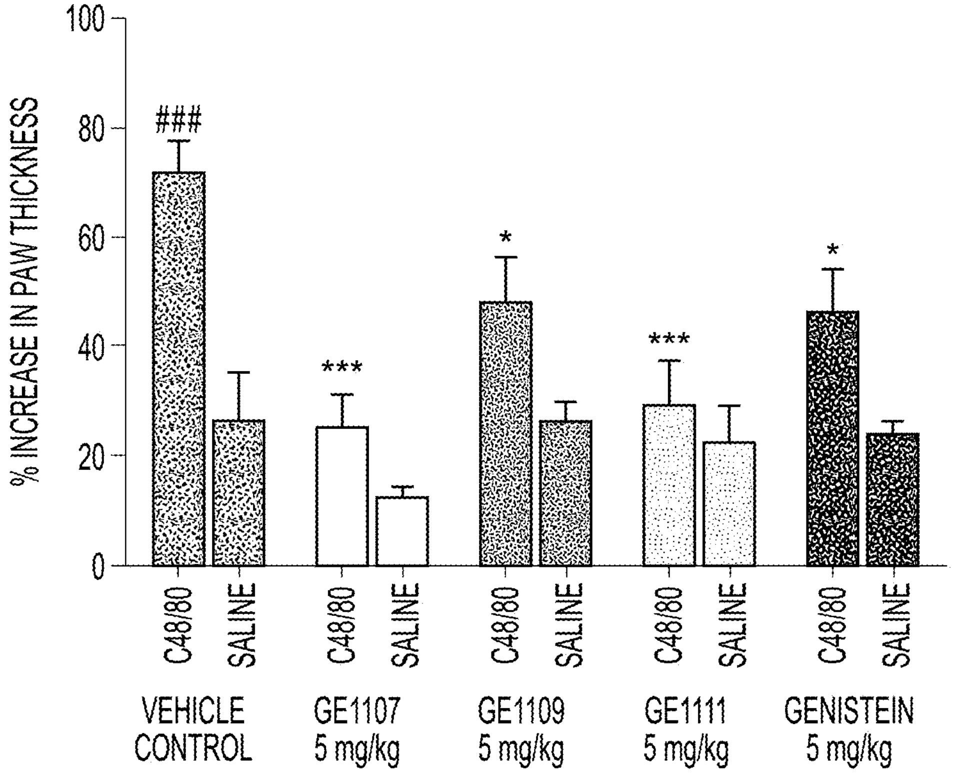
FIGS. 10A-10B are bar graphs showing the in vivo effect of the small compound antagonists (GE0117, GE1109 and GE1111) and genistein on Evans blue paw extravasation in pseudo allergic/local anaphylaxis mice model.
Figure 10B:
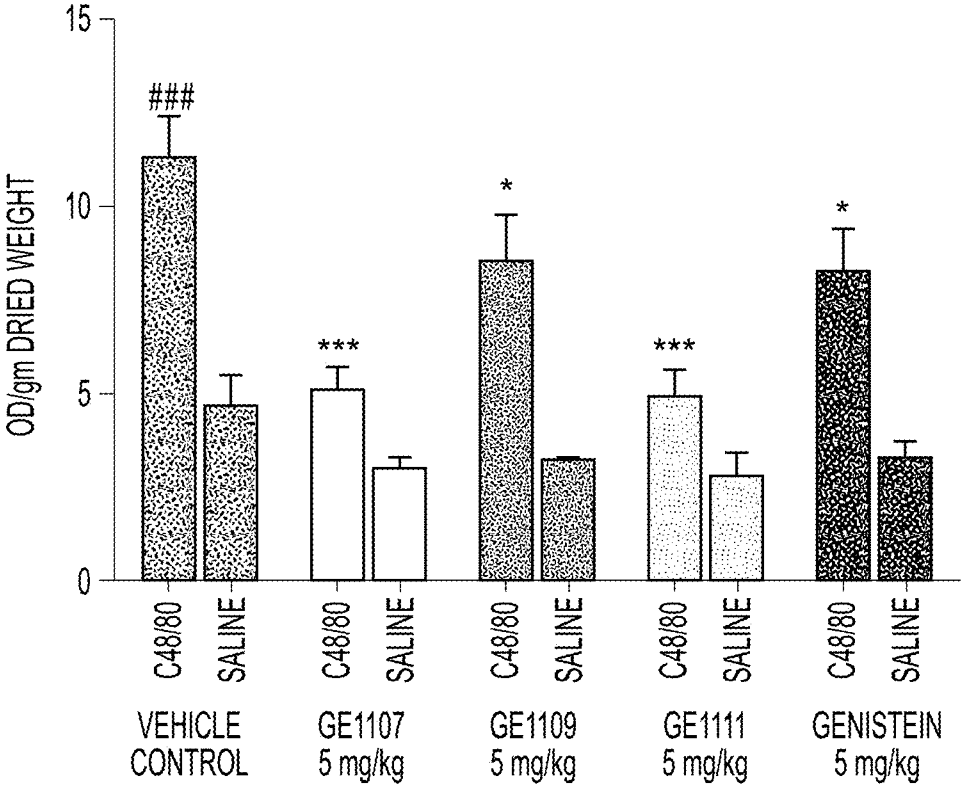
Figure 11:
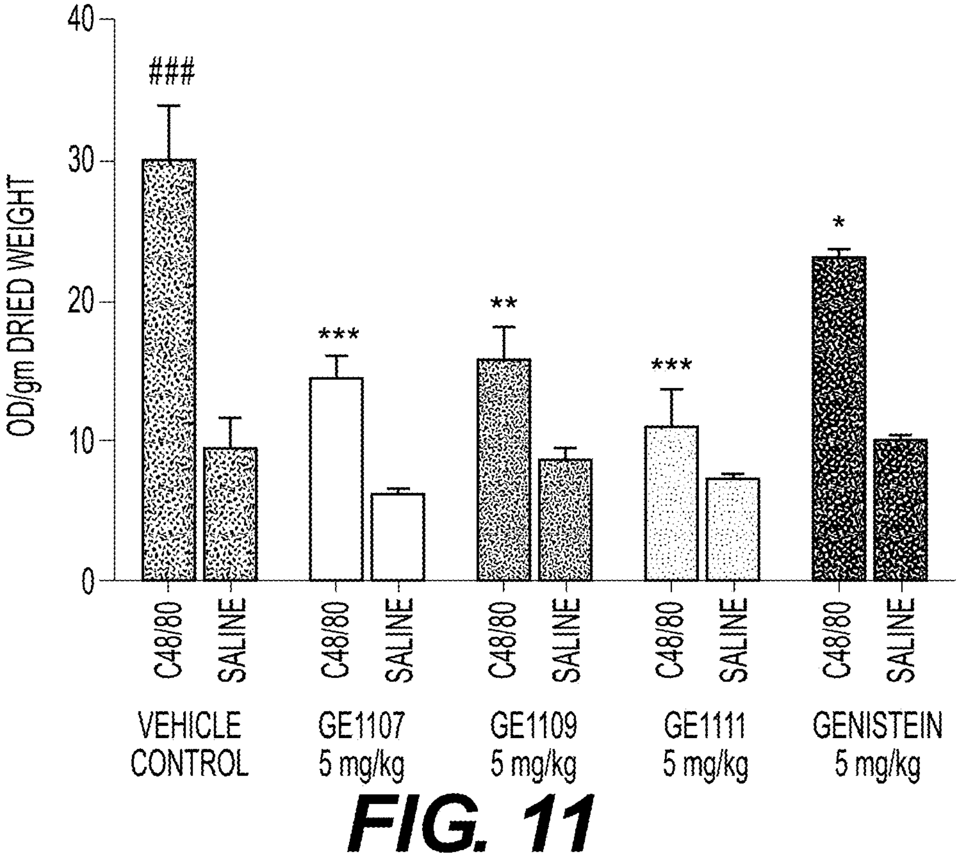
FIG. 11 is a bar graph showing the quantification of Evans blue leakage into the ear after 15 min of 30 μg/ml C48/80 injection using a pseudo allergic/local anaphylaxis mice model. The data are presented as the mean±SEM from 6-8 mice/group, $^{###}$p<0.001 as compared to saline and *P<0.05, P<0.001, *P<0.0001 as compared to C48/80.

Evaluation of the Effect of Potent Small Compound Antagonists on In-Vivo Local Anaphylaxis/Pseudo Allergic Mice Model MRGPRB2 is the mouse orthologous receptor to the human MRGPRX2 and demonstrates a similar agonistic response to C48/80 as its human counterpart. From the in-vitro experiments, the potency of the small compound antagonists was demonstrated. Next, an in-vivo mouse model of C48/80 induced local pseudo allergic reactions was tested. This model is a widely used animal model to evaluate the activity of drugs (agonist/antagonist) against MRGPRB2/MRGPRX2 induced pseudo allergic response. Evans blue dye was injected intravenously to visualize the vascular permeability and to quantify the extravasation/edema. Vehicle control or antagonist treated mice (5 mg/kg body weight, intraperitoneally) were injected with saline or C48/80 in the respective ears and paws. The paw thickness and Evans blue extravasation (an indicator of MCs degranulation) have been assessed. Genistein was used as a positive control. Significant increases in paw thickness (FIG. 10A; paw images not shown) and Evans blue dye extravasation (indicative of vascular leakage) in the ears and paws of C48/80 treated mice ($^{\#\#\#}$p<0.001) (FIGS. 10B and 11; paw and ear images not shown) as compared to saline-treated mice has been observed. This response, however, is significantly reduced in the antagonist-treated mice groups. The small compound antagonist GE0117 and GE1111 have significantly (*P<0.001) attenuated the increased paw thickness and increased Evan blue dye extravasation compared to C48/80 mice (FIGS. 10A and 10**B). GE1109 and genistein have also shown a significant (*P<0.05) antagonizing activity compared to C48/80 mice. Among all, GE0117 and GE1111 have shown a potent antagonistic activity as compared to genistein. The C48/80 induced pseudo allergic mice model represents the immediate phase of MCs response (degranulation) because of its short duration and acute nature. The accumulation of vascular fluids in the paw tissue is because of MCs mediators release, which causes vasodilation and vascular leakage. Thus, the observed decrease in paw edema following antagonist treatment is likely through inhibition of MCs activation. The in-vivo results are consistent with the in-vitro findings that show the therapeutic potential of the small compounds against local anaphylaxis reactions.

Figure 12A:
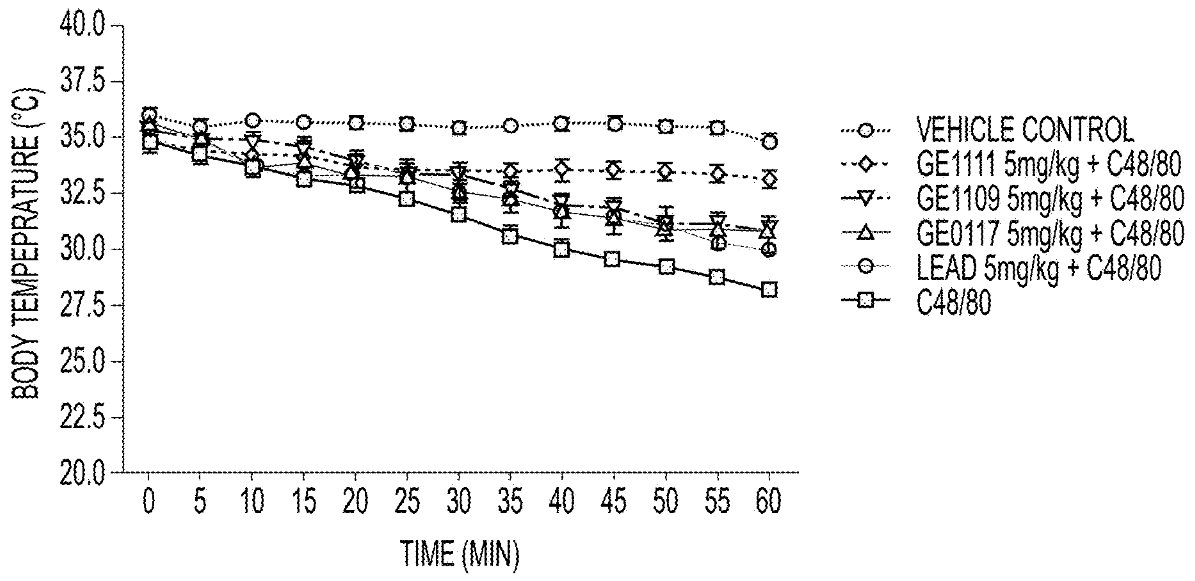
FIGS. 12A-12B are graphs showing the in vivo effect of the small compound antagonists (GE0117, GE1109, and GE1111) and genistein on C48/80 induced systemic anaphylaxis.
Figure 12B:
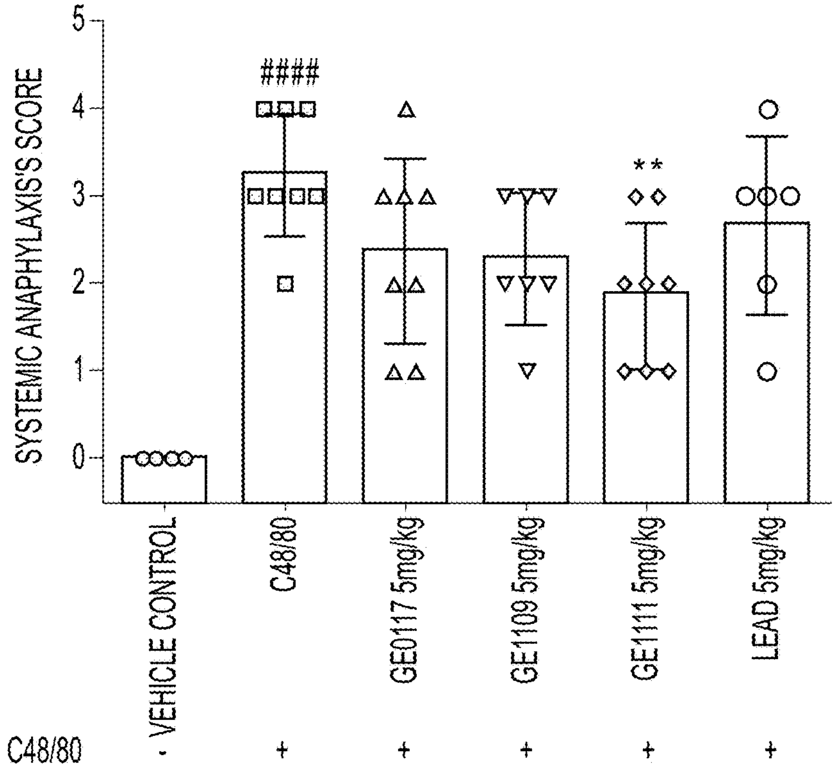

Evaluation of the Effect of Potent Small Compound Antagonists on In-Vivo Systemic Anaphylaxis Mice Model Anaphylactic shock is a sudden onset, life-threatening systemic allergic reaction manifested by hypothermia, scratching, edema, respiratory distress, etc. that can occur within minutes after contact with an allergen. The mice's body temperature and anaphylaxis symptoms were monitored for 1 hour or until death. After 30 minutes of vehicle and antagonist/genistein treatment (5 mg/kg body weight, intraperitoneally), mice were injected with C48/80 (8 mg/kg body weight, intraperitoneally). The genistein was used as a positive control. In the systemic anaphylaxis animal model, the endpoint is mortality because of its sudden fatal nature, which may cause death. However, no mortality has been observed in any experimental group after 1 h of C48/80 injection. A significant decrease in the body temperature after 10 minutes ($^{\#\#}$p<0.01) of C48/80 injection in the C48/80 control group has been observed compared to saline-treated mice. The maximum body temperature drops in C48/80 treated group was at 20 minutes ($^{\#\#\#\#}$p<0.0001) while there is no change in body temperature in the saline-treated group. The small compound antagonist GE1109 (*p<0.05) and GE1111 (**p<0.01) reversed the C48/80 induced body temperature changes at 30 minutes. At 35 minutes, all the antagonist treated groups, GE0117 (*p<0.05), GE1109 (p<0.01), GE1111 (**p<0.0001), and genistein (*p<0.05) significantly reversed the body temperature change in C48/80 treated group (FIG. 12A). Further, the C48/80 treated mice show severe anaphylaxis symptoms (wheezing, labored respiration, and cyanosis around the mouth and no activity after prodding) than saline-treated mice (FIG. 12B). The GE1111 (p<0.01) treated group rehabilitated the compound 48/80 induced hypothermia and severity of anaphylaxis symptoms. The other antagonist-treated groups showed fewer anaphylaxis symptoms but are not significantly different from the C48/80 treated mice (FIG. 12**B).

Figure 13:
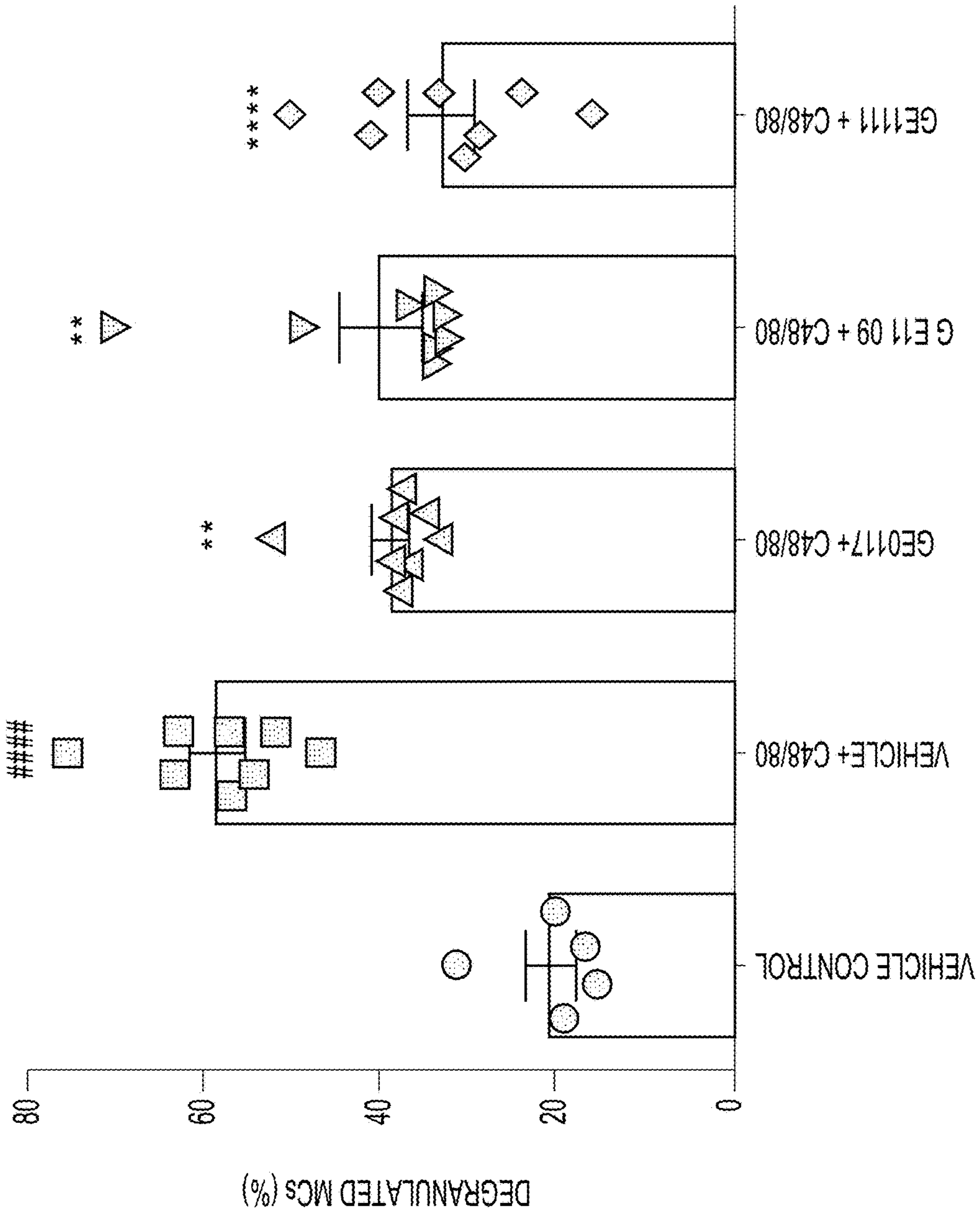
FIG. 13 is a bar graph showing the quantitative evaluation of degranulated MCs in different experimental groups from 20× magnified tissue sections. The paraffin-embedded skin sections from a different group of mice were stained with H&E to evaluate tissue morphology and inflammation and Toluidine blue to detect in vivo MCs degranulation. Data represent the percentage of degranulated MCs (mean±SEM) from 6-8 mice/group. $^{####}$p<0.0001 as compared to vehicle, P<0.01, **P<0.0001 as compared to vehicle+C48/80.
Figure 14:
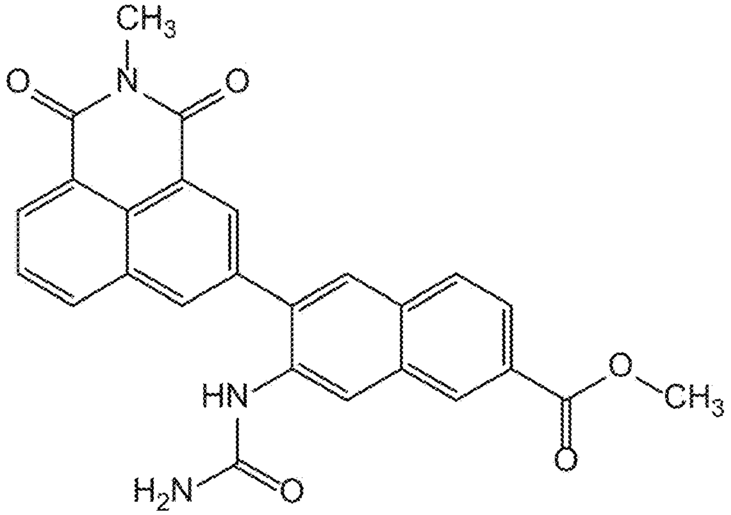
FIG. 14 shows the chemical structures of compounds GE0117, GE0118, and GE0119.
Figure 14:
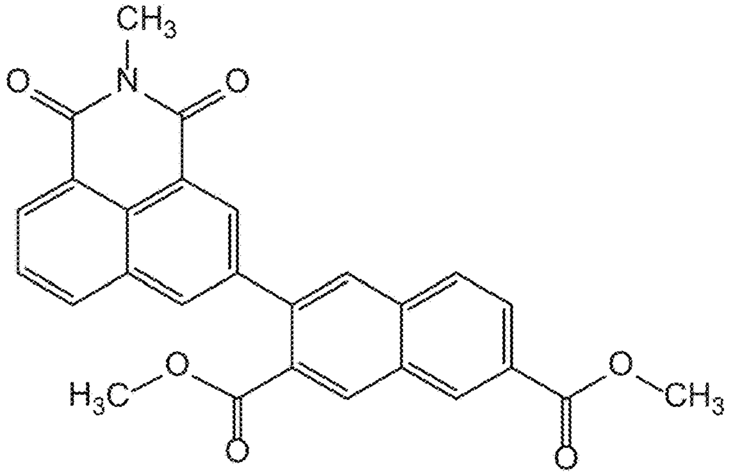
Figure 14:
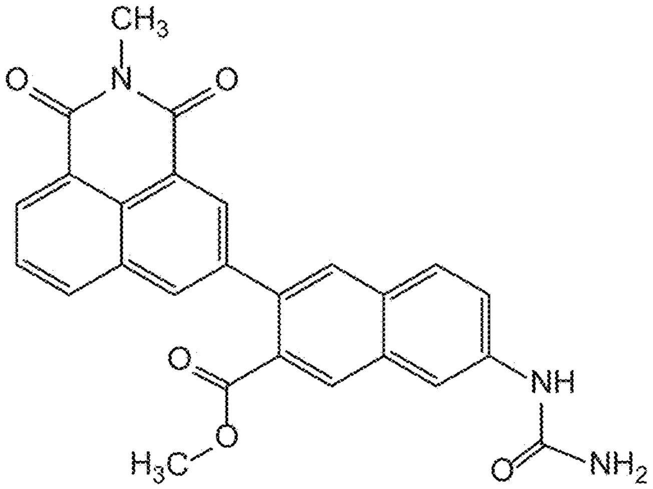
Figure 15:
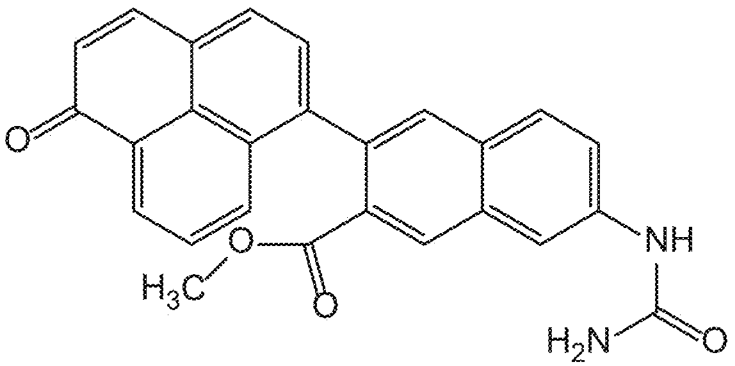
FIG. 15 shows the chemical structures of compounds GE1109, GE1110, and GE1111.
Figure 15:
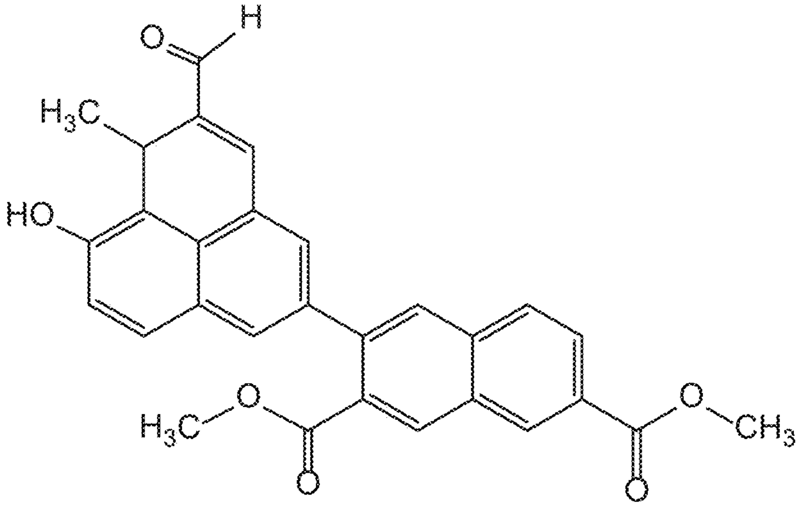
Figure 15:
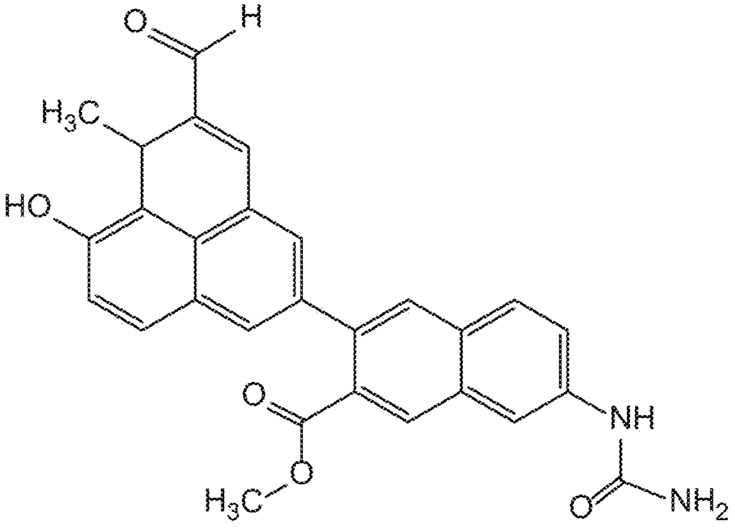

Evaluation of the Effect of Potent Small Compound Antagonist on Histological Changes and In-Vivo MCs Degranulation To evaluate the effect of small compound antagonists on C48/80 induced histological changes and in-vivo MCs degranulation, H&E, and Toluidine blue staining of the ear tissue were performed, respectively. In the H&E ear staining of vehicle+C48/80 experimental group, more inflammation (thickness) and cellular infiltration than vehicle-treated experimental group mice have been shown. The extent of inflammation and infiltration was reduced in the antagonist treated experimental mice as compared to C48/80 treated group (images not shown). To evaluate the in-vivo antagonistic effect, C48/80 induced MCs degranulation in ear tissue has been investigated. The numbers of degranulated and non-degranulated MCs in the 20× magnified ear sections of mice from each experimental group have been measured. Degranulated MCs are distinct from non-degranulated cells by reduced toluidine blue staining intensity and dispersed visible cytoplasmic granules. While there was no significant difference in the total numbers of MCs between the vehicle and the antagonist treated experimental group of mice (data not shown), the percentage of degranulated MCs was significantly higher in the C48/80 treated group ($^{\#\#\#\#}$p<0.0001). Treatment with GE1107 (p<0.01), GE1109 (p<0.01) and GE1111 (**p<0.0001) reduces the MCs degranulation as compared to the C48/80 treated group (FIG. 13**; images not shown). These histological results demonstrate the potential of small compound antagonists in inhibiting MC-induced inflammation associated with pseudo-allergic reactions in vivo.

In summary, small compound antagonists for the treatment of non-IgE MRGPRX2 mediated pseudo allergic reactions following computational and experimental pharmacology approaches have been identified. The results show that the small compound antagonists, in particular GE0117, GE1109 and GE1111 are potent drug candidates with inhibitory activities against MRGPRX2 mediated MCs degranulation, calcium influx, inflammatory cytokines, vascular edema, inflammation and systemic anaphylaxis reactions. Given that MCs-MRGPRX2 activation plays a role in the etiology of pseudo-allergic reactions to several FDA-approved drugs, endogenous and exogenous peptides, and chronic inflammation associated with asthma, the small compound antagonist developed herein can be used as a treatment option for these conditions.

REFERENCES

Solensky and Khan, *Annals of allergy, asthma & immunology,* 2010. 105(4): p. 259-273.
Porebski, G., et al., *Frontiers in immunology,* 2018. 9: p. 3027.
Yuan, F., et al., *Biomedicine & Pharmacotherapy,* 2021. 137: p. 111323.
Navinés-Ferrer, A., et al., *Scientific reports,* 2018. 8(1): p. 1-11.
Gell, P., *Clinical aspects of immunology,* 1963: p. 317-337.
Rajan, T., *TRENDS in Immunology,* 2003. 24(7): p. 376-379.
Tončić, et al., *Acta dermatovenerologica Croatica,* 2009. 17(1): p. 0-0.
He, S.-h., et al., *Acta Pharmacologica Sinica,* 2013. 34(10): p. 1270-1283.
Krystel-Whittemore, M., et al., *Frontiers in immunology,* 2016. 6: p. 620.
Atanaskovic-Markovic, M., et al., *Pediatric Allergy and Immunology,* 2019. 30(3): p. 269-276.
Ben-Shoshan and Clarke, *Allergy,* 2011. 66(1): p. 1-14.
Kumar, M., et al., *Molecules,* 2020. 25(5): p. 1028.
Ding, Y., et al., *International immunopharmacology,* 2019. 66: p. 185-197.
Callahan, B. N., et al., *Frontiers in Immunology,* 2020. 11: p. 703.
Bulfone-Paus, S., et al., *Trends in immunology,* 2017. 38(9): p. 657-667.
Subramanian, H., et al., *Journal of Allergy and Clinical Immunology,* 2016. 138(3): p. 700-710.
Motakis, E., et al., *Blood,* 2014. 123(17): p. e58-e67.
McNeil, B. D., et al., *Nature,* 2015. 519(7542): p. 237-241.
Dong, X., et al., *Cell,* 2001. 106(5): p. 619-632.
Demoly, P., et al., *Allergy,* 1999. 54(5): p. 500-506.
Ogasawara, H., et al., *Journal of leukocyte biology,* 2019. 106(5): p. 1069-1077.
Kühn, H., et al., *Journal of Allergy and Clinical Immunology,* 2020.
Babina, M., *Itch,* 2020. 5(2): p. e32.
Berman, H. M., et al., *Nucleic Acids Res,* 2000. 28: p. 235-242.
Lansu, K., et al., *Nature chemical biology,* 2017. 13(5): p. 529-536.
Reddy, V. B., et al., *Journal of Allergy and Clinical Immunology,* 2017. 140(6): p. 1726-1728.
Trott, O. and A. J. Olson, *Journal of computational chemistry,* 2010. 31(2): p. 455-461.
Read, G. W., et al., *Journal of medicinal chemistry,* 1973. 16(11): p. 1292-1295.
Aridor, M., et al., *The Journal of cell biology,* 1990. 111(3): p. 909-917.
Bueb, J.-L., et al., *Mol Pharmacol,* 1990. 38(6): p. 816-822.
Mousli, M., et al., *Immunology letters,* 1990. 25(4): p. 355-357.
Sunseri, and Koes, *Nucleic acids research,* 2016. 44(W1): p. W442-W448.
Hughes, J. P., et al., *British journal of pharmacology,* 2011. 162(6): p. 1239-1249.
Lipinski, C. A., et al., *Advanced drug delivery reviews,* 1997. 23(1-3): p. 3-25.
Kroeze, W. K., et al., *Nature structural & molecular biology,* 2015. 22(5): p. 362-369.
Subramanian, H., et al., *Journal of Biological Chemistry,* 2011. 286(52): p. 44739-44749.
Occhiuto, C. J., et al., *Frontiers in immunology,* 2020. 10: p. 3143.
Ferguson, S. S., *Pharmacological reviews,* 2001. 53(1): p. 1-24.
Arima, M. and T. Fukuda, *The Korean journal of internal medicine,* 2011. 26(1): p. 8.
Castellani, M., et al., 2009, *SAGE Publications Sage UK,* London, England.
Jimenez-Rodriguez, T. W., et al., *Journal of asthma and allergy,* 2018. 11: p. 121.
Yoon, T. J., et al., *International immunopharmacology,* 2013. 15(4): p. 666-670.
Che, T., et al., *Cell,* 2018. 172(1-2): p. 55-67. e15.
Singh, K., et al., *Plos one,* 2016. 11(3): p. e0149359.
Webb, B. and A. Sali, *Current protocols in bioinformatics,* 2016. 54(1): p. 5.6. 1-5.6. 37.
Prisant, M., et al., *Proteins,* 2003. 50: p. 437-450.
Hanwell, M. D., et al., *Journal of cheminformatics,* 2012. 4(1): p. 17.
Dallakyan, S. and A. J. Olson, *Chemical biology,* 2015, Springer. p. 243-250.
Ding, Y., et al., *Computational biology and chemistry,* 2016. 64: p. 403-413.
Mashiach, E., et al., *Nucleic acids research,* 2008. 36(suppl_2): p. W229-W232.
Schrodinger, L., *Version,* 2010. 1(5): p. 0.
Release, S., *Maestro-Desmond Interoperability Tools,* Schrödinger, New York, NY, 2017.
Biovia, D. S., *Discovery studio modeling environment,* 2017, Release.
Daina, A., et al., *Scientific reports,* 2017. 7(1): p. 1-13.
Lipinski, C. A., *Journal of pharmacological and toxicological methods,* 2000. 44(1): p. 235-249.
Rådinger, M., et al., *Current protocols in immunology,* 2010. 90(1): p. 7.37. 1-7.37. 12.
Kroeze, W. K., et al., *Nature structural & molecular biology,* 2015. 22(5): p. 362.
Slater, T., et al., *Biochimica et biophysica acta,* 1963. 77: p. 383-393.
Alley, M. C., et al., *Cancer research,* 1988. 48(3): p. 589-601.
Shin, T., et al., *Journal of ethnopharmacology,* 2001. 74(2): p. 133-140.
Li, X.-M., et al., *Journal of Allergy and Clinical Immunology,* 2000. 106(1): p. 150-158.

We claim:

1. A compound having the structure of

Formula Ia

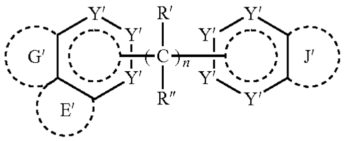

(a) wherein n is 0 or 1;
(b) wherein R' and R" are independently a hydrogen or an unsubstituted alkyl;
(c) wherein Formula II

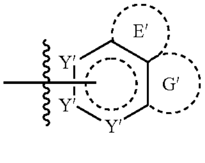

has the structure of

Formula IVa

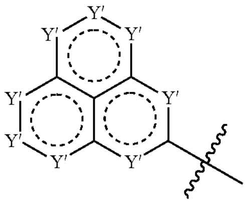

or

Formula IVb

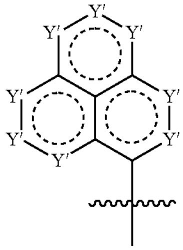

(d) wherein

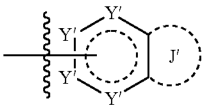

has the structure of

Formula VIII

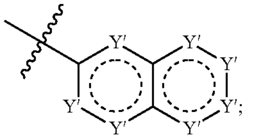

(e) wherein each occurrence of Y' is independently $CR_1$, O, S, or $NR_2$, $R_1$ and $R_2$ are independently a hydrogen, an unsubstituted alkyl, a carbonyl, an alkoxy, an amido, an amino, an oxo, a thiol, or a hydroxyl, with the proviso that when G' and E' are substituted aryl, the substituent is not an alkoxy.

2. The compound of claim 1, wherein n is 0.

3. The compound of claim 1, wherein

Formula II

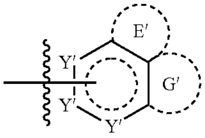

has the structure of

Formula Va

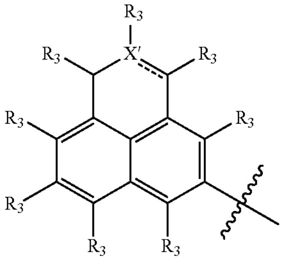

or

Formula Vb

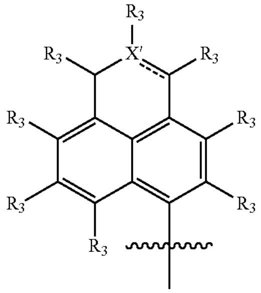

(a) wherein X' is C, N, O, or S;

(b) wherein each occurrence of $R_3$ is independently a hydrogen, an unsubstituted alkyl, a carbonyl, an alkoxy, an amido, an amino, an oxo, a thiol, or a hydroxyl.

4. The compound of claim 3, (a) wherein X' is C or N; and (b) wherein each occurrence of $R_3$ is independently a hydrogen, an unsubstituted alkyl, a carbonyl, an amido, an oxo, or a hydroxyl.

5. The compound of claim 3, (a) wherein X' is C or N;

(b) wherein each occurrence of $R_3$ is independently a hydrogen, an unsubstituted $C_1$-$C_6$ alkyl, a formyl group, an oxo, or a hydroxyl.

6. The compounds of claim 1, wherein

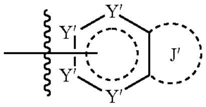

has the structure of

Formula IX

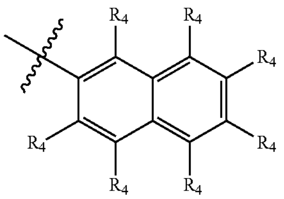

wherein each occurrence of $R_4$ can be independently a hydrogen, an unsubstituted alkyl, a carbonyl, an alkoxy, an amido, an amino, an oxo, a thiol, or a hydroxyl.

7. The compound of claim 6, wherein each occurrence of $R_4$ is independently a hydrogen,

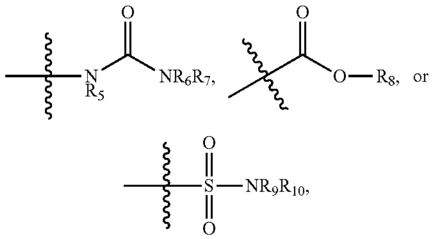

and $R_5$-$R_{10}$ are independently a hydrogen or an unsubstituted alkyl.

8. The compound of claim 6, wherein each occurrence of $R_4$ is independently a hydrogen,

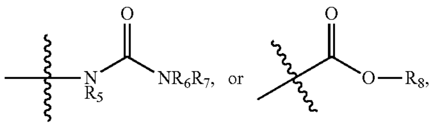

and $R_5$-$R_8$ are independently hydrogen or an unsubstituted $C_1$-$C_4$ alkyl.

9. A compound selected from the group consisting of

GE0117

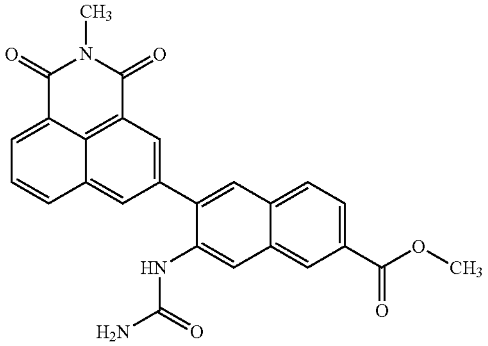

GE0118

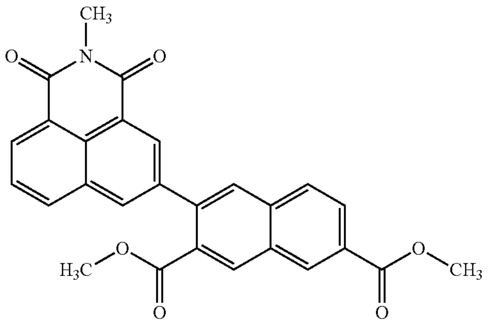

-continued

GE0119

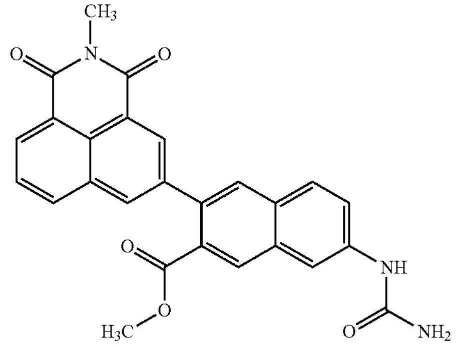

GE1109

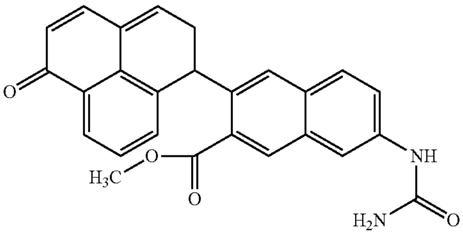

GE1110

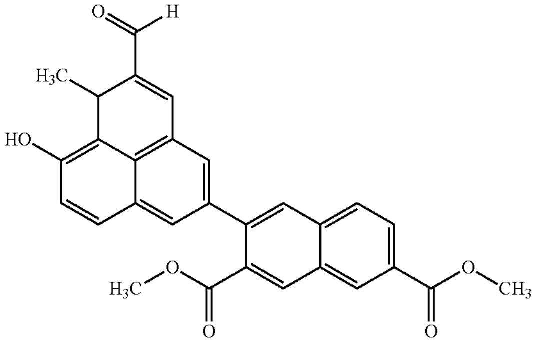

and

GE1111

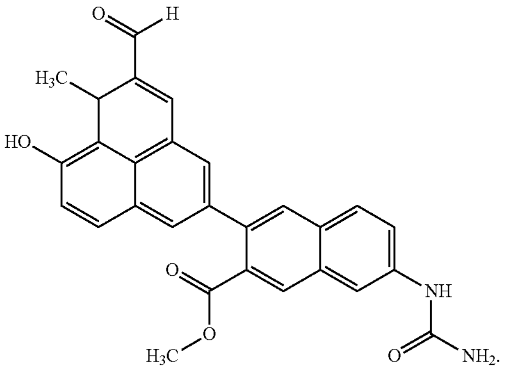

10. A pharmaceutical formulation comprising one or more compounds of claim 1; and a pharmaceutically acceptable excipient, wherein the one or more compounds are in an effective amount to prevent or treat a pseudo allergic reaction, a pseudo allergic disease, or a pseudo inflammatory disease, or treat or ameliorate one or more symptoms associated with a pseudo allergic reaction, a pseudo allergic disease, or a pseudo inflammatory disease in a subject.

11. The pharmaceutical formulation of claim 10 further comprising a second active agent, optionally more than one second active agent.

12. The pharmaceutical formulation of claim 10, wherein the second active agent is an antiallergic agent or an anti-inflammatory agent, or a combination thereof.

13. A method for making the compound of claim 1 comprising (i) mixing a reactant mixture and a catalyst to form a reaction mixture, wherein the reactant mixture comprises a first reactant, a second reactant, and a solvent; and (ii) heating the reaction mixture at a suitable temperature for a period of time sufficient to form a product containing the compound of claim 1, wherein step (i) is performed prior to or simultaneously with step (ii).

14. The method of claim 13, wherein the first reactant has the structure of Formula XIII

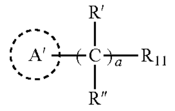

(a) wherein a is an integer from 0 to 6, from 0 to 5, from 0 to 4, from 0 to 3, from 0 to 2, or 0 or 1;

(b) wherein R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;

(c) wherein A' is a substituted or unsubstituted polyaryl or a substituted or unsubstituted polyheteroaryl;

(d) wherein $R_{11}$ is a halogen or has the structure of

Formula XIV

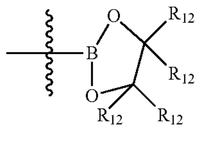

wherein each occurrence of $R_{12}$ is independently a hydrogen or a substituted or unsubstituted alkyl; and (e) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

15. The method of claim 13, wherein the second reactant has the structure of Formula XIX

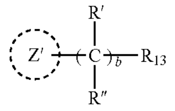

(a) wherein b is an integer from 0 to 6, from 0 to 5, from 0 to 4, from 0 to 3, from 0 to 2, or 0 or 1;

(b) wherein R' and R" are independently a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, an amido, an amino, an oxo, a phosphonium, a phosphanyl, a phosphonyl, a silyl, a sulfinyl, a sulfonyl, a thiol, a hydroxyl, or a halogen;

(c) wherein Z' is a substituted or unsubstituted polyaryl or a substituted or unsubstituted polyheteroaryl;

(d) wherein $R_{13}$ is trifluoromethanesulfonate ("OTf") or has the structure of Formula XIV; and (e) wherein the substituents are independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a substituted or unsubstituted carbonyl, a substituted or unsubstituted alkoxy, a halogen, a hydroxyl, a phenoxy, an aroxy, an alkylthio, a phenylthio, an arylthio, a cyano, an isocyano, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol.

16. The method of claim 13, wherein the solvent is water, dioxane, dimethoxyethane, 2-methyl tetrahydrofuran, cyclopentyl methyl ether, tetrahydrofuran, tert-butyl methyl ether, or dichloromethane, or a combination thereof.

17. The method of claim 13, wherein the catalyst is $PdCl_2$(dppf), $PdCl_2$(dppf)DCM Complex, Tetrakis, $PdCl_2(PPh_3)_2$, XPhos Pd G3, or $Pd(OAc)_2/PPh_3$, or a combination thereof.

18. The method of claim 13, wherein in step (ii), the reaction mixture is heated at a temperature in a range from 50° C. to 150° C., from 60° C. to 150° C., from 70° C. to 150° C., from 80° C. to 150° C., from 50° C. to 140° C., from 50° C. to 120° C., from 70° C. to 120° C., from 80° C. to 120° C., such as about 100° C., for a time period of at least 1 hour, at least 2 hours, at least 3 hours, at least 4 hours, at least 5 hours, at least 6 hours, at least 8 hours, at least 10 hours, up to 20 hours, up to 18 hours, up to 16 hours, in a range from 1 hour to 18 hours, from 2 hours to 16 hours, or from 2 hours to 15 hours.

19. The method of claim 13 further comprising mixing the first reactant, the second reactant, and the solvent to form the reactant mixture prior to step (i), purging the reactant mixture with an inert gas prior to step (ii), stirring the reaction mixture during step (ii), and/or purifying the product containing the compound.

20. A method for treating mast cells ("MCs") in a subject in need thereof comprising, (i) administering to the subject an effective amount of a compound selected from the compounds in claim 9, wherein step (i) occurs one or more times, and wherein the effective amount of the compound is effective to inhibit MCs degranulation, inhibit MRGPRX2 activation, reduce calcium cation ("$Ca^{2+}$") flux in the MCs, and/or reduce release of inflammatory chemokine and/or cytokine.

21. The method of claim 20, wherein step (i) occurs more than one time.

22. A compound having the structure of

Formula XIa

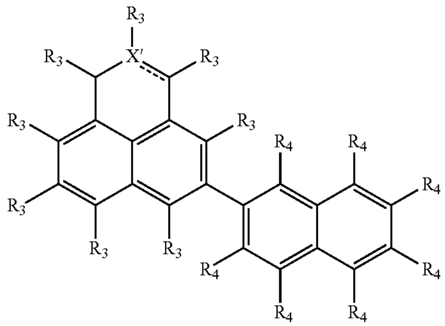

-continued

Formula XIb

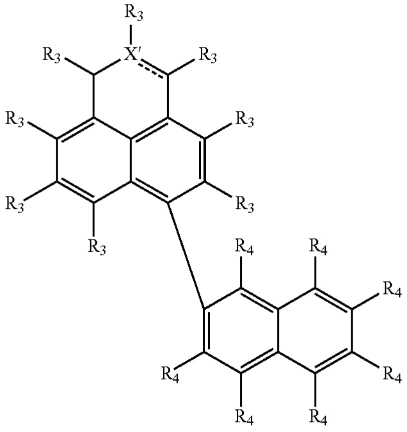

wherein:

(a) X' is C, N, O, or S; and (b) each occurrence of $R_3$ and $R_4$ are independently a hydrogen, an unsubstituted alkyl, a carbonyl, an alkoxy, an amido, an amino, an oxo, a thiol, or a hydroxyl.

23. The compound of claim 22, wherein:

(a) X' is C or N; and (b) each occurrence of $R_3$ is independently a hydrogen, an unsubstituted $C_1$-$C_6$ alkyl, a formyl group, an oxo, or a hydroxyl.

24. The compound of claim 22, wherein each occurrence of $R_4$ is independently a hydrogen,

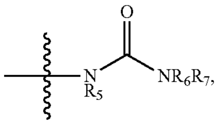 or 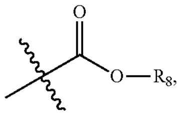

and $R_5$-$R_8$ are independently hydrogen or an unsubstituted $C_1$-$C_4$ alkyl.

* * * * *